US012009075B2

(12) United States Patent
Kaput et al.

(10) Patent No.: US 12,009,075 B2
(45) Date of Patent: Jun. 11, 2024

(54) PERSONALIZED HEALTH SYSTEM, METHOD AND DEVICE HAVING A LIFESTYLE FUNCTION

(71) Applicant: VYDIANT, INC, Folsom, CA (US)

(72) Inventors: James Kaput, Madison, WI (US); Corrado Priami, Follonica (IT); Melissa Morine, Avonport (CA); Terry Carlone, Sacramento, CA (US); John Green, Burke, VA (US)

(73) Assignee: Vydiant, Inc., Folsom, CA (US)

( * ) Notice: Subject to any disclaimer, the term of this patent is extended or adjusted under 35 U.S.C. 154(b) by 0 days.

(21) Appl. No.: 17/705,160

(22) Filed: Mar. 25, 2022

(65) Prior Publication Data

US 2022/0310264 A1    Sep. 29, 2022

Related U.S. Application Data

(60) Provisional application No. 63/166,416, filed on Mar. 26, 2021, provisional application No. 63/166,427, filed on Mar. 26, 2021.

(51) Int. Cl.
*G16H 50/30*    (2018.01)
*A61B 5/00*    (2006.01)
(Continued)

(52) U.S. Cl.
CPC ............. *G16H 10/60* (2018.01); *A61B 5/742* (2013.01); *A61B 5/7465* (2013.01); *A61B 5/7475* (2013.01); *G06F 3/04847* (2013.01); *G06F 9/453* (2018.02); *G06N 5/04* (2013.01); *G16H 10/20* (2018.01); *G16H 15/00* (2018.01); *G16H 20/17* (2018.01); *G16H 20/30* (2018.01); *G16H 20/60* (2018.01); *G16H 20/70* (2018.01);
(Continued)

(58) Field of Classification Search
CPC ........................... G16H 50/30; G06F 3/04847
See application file for complete search history.

(56) References Cited

U.S. PATENT DOCUMENTS 6,163,781 A    12/2000  Wess, Jr.
9,483,606 B1 *    11/2016  Dean ...................... H04L 67/55
(Continued)

FOREIGN PATENT DOCUMENTS

CN        107103177 A  *  8/2017  ......... G06F 19/3431
WO    WO-2012090226 A2  *  7/2012  ......... G06F 19/3431
(Continued)

OTHER PUBLICATIONS

Reis et al., Development of a Health Lifestyle Assessment Toolkit for the General Public, Jun. 27, 2019, Frontiers in Medicine, 6:134 (Year: 2019).*
(Continued)

*Primary Examiner* — Karen A Hranek
(74) *Attorney, Agent, or Firm* — Haverstock & Owens, A Law Corporation

(57) ABSTRACT

A personal health system, method and device that maintains a health knowledge base, inputs user characteristics, generates health scores based on the user characteristics and provides recommendations based on the user characteristics, health scores and knowledge base, wherein the recommendations are indicated by the knowledge base to be likely to improve the user's health.

30 Claims, 29 Drawing Sheets

(51) Int. Cl.
  *G06F 3/04847* (2022.01)
  *G06F 9/451* (2018.01)
  *G06N 5/04* (2023.01)
  *G16H 10/20* (2018.01)
  *G16H 10/60* (2018.01)
  *G16H 15/00* (2018.01)
  *G16H 20/17* (2018.01)
  *G16H 20/30* (2018.01)
  *G16H 20/60* (2018.01)
  *G16H 20/70* (2018.01)
  *G16H 40/67* (2018.01)
  *G16H 70/40* (2018.01)
  *G16H 70/60* (2018.01)

(52) U.S. Cl.
  CPC ............. *G16H 40/67* (2018.01); *G16H 50/30* (2018.01); *G16H 70/40* (2018.01); *G16H 70/60* (2018.01)

(56) References Cited

U.S. PATENT DOCUMENTS

| | | | |
|---|---|---|---|
| 9,727,885 B1 | 8/2017 | Benovate | |
| 10,860,621 B1* | 12/2020 | Ross | G16H 10/60 |
| 2003/0074142 A1 | 4/2003 | Steeg | |
| 2008/0046916 A1 | 2/2008 | Shivaji-Rao | |
| 2008/0228699 A1 | 9/2008 | Kenedy et al. | |
| 2012/0072233 A1* | 3/2012 | Hanlon | G16H 20/60 705/2 |
| 2012/0089909 A1 | 4/2012 | Block | |
| 2012/0203707 A1* | 8/2012 | Hungerford | G06Q 30/0279 705/329 |
| 2012/0221350 A1 | 8/2012 | Kenedy | |
| 2012/0290327 A1 | 11/2012 | Hanlon | |
| 2012/0313776 A1 | 12/2012 | Utter, II | |
| 2013/0030260 A1* | 1/2013 | Hale | G16H 50/30 600/301 |
| 2013/0035949 A1* | 2/2013 | Saltzman | G06Q 10/06 434/262 |
| 2013/0138239 A1 | 5/2013 | Chen | |
| 2013/0216982 A1 | 8/2013 | Bennett | |
| 2014/0067730 A1 | 3/2014 | Kozloski | |
| 2014/0074510 A1 | 3/2014 | Mcclung et al. | |
| 2014/0076318 A1 | 3/2014 | Flower | |
| 2014/0114680 A1 | 4/2014 | Mills | |
| 2014/0156308 A1 | 6/2014 | Ohnemus | |
| 2015/0025809 A1 | 1/2015 | Herron | |
| 2015/0164409 A1 | 6/2015 | Benson | |
| 2015/0194071 A1 | 7/2015 | Bennett | |
| 2015/0220697 A1* | 8/2015 | Hunt | G16H 20/60 705/2 |
| 2015/0235562 A1* | 8/2015 | Klein | G09B 5/02 434/127 |
| 2015/0269321 A1 | 9/2015 | Soon-Shiong | |
| 2016/0151603 A1 | 6/2016 | Shouldice | |
| 2016/0217266 A1 | 7/2016 | Damani et al. | |
| 2016/0270717 A1 | 9/2016 | Lung et al. | |
| 2016/0275253 A1 | 9/2016 | Shimura | |
| 2017/0147775 A1* | 5/2017 | Ohnemus | G16H 50/30 |
| 2017/0249445 A1 | 8/2017 | Devries | |
| 2017/0262604 A1 | 9/2017 | Francois | |
| 2017/0277841 A1 | 9/2017 | Shanker | |
| 2017/0291067 A1 | 10/2017 | Jang | |
| 2017/0293722 A1 | 10/2017 | Valverde, Jr. | |
| 2017/0300655 A1* | 10/2017 | Lane | G16H 10/60 |
| 2017/0323078 A1 | 11/2017 | Michon et al. | |
| 2018/0082317 A1* | 3/2018 | Reier | G16H 70/20 |
| 2018/0110960 A1 | 4/2018 | Youngblood | |
| 2018/0192136 A1 | 7/2018 | Grabowski | |
| 2018/0233064 A1 | 8/2018 | Dunn | |
| 2018/0233223 A1 | 8/2018 | Solari | |
| 2018/0268821 A1 | 9/2018 | Levanon | |
| 2018/0277248 A1* | 9/2018 | Nazem | G16H 50/30 |
| 2018/0344215 A1 | 12/2018 | Ohnemus | |
| 2019/0008577 A1 | 1/2019 | Lazarus | |
| 2019/0026364 A1* | 1/2019 | Sankovsky | G06Q 40/08 |
| 2019/0026837 A1* | 1/2019 | Takasaki | G06Q 10/063 |
| 2019/0065692 A1* | 2/2019 | Connelly | G16H 50/30 |
| 2019/0099582 A1 | 4/2019 | Crow | |
| 2019/0371452 A1 | 12/2019 | Mainardi | |
| 2020/0118685 A1* | 4/2020 | Lee | A61B 5/318 |
| 2020/0143947 A1 | 5/2020 | Choi | |
| 2020/0163824 A1 | 5/2020 | Kim | |
| 2020/0205728 A1 | 7/2020 | Molina | |
| 2020/0321133 A1* | 10/2020 | Gonzales, Jr. | G16H 40/20 |
| 2021/0012900 A1* | 1/2021 | Smith | G16H 50/30 |
| 2021/0182918 A1* | 6/2021 | Trairattanapa | G06Q 30/0269 |
| 2021/0287803 A1* | 9/2021 | Radrich | A61B 5/7275 |
| 2021/0365951 A1* | 11/2021 | Benkreira | G06Q 20/18 |
| 2022/0028503 A1* | 1/2022 | Bull | G16H 20/70 |
| 2022/0030382 A1 | 1/2022 | Klassen | |
| 2022/0139570 A1* | 5/2022 | Hettig | G06Q 10/10 705/2 |
| 2023/0343459 A1* | 10/2023 | Prozorovscaia | G16H 20/70 |

FOREIGN PATENT DOCUMENTS

| | | | |
|---|---|---|---|
| WO | 2014069896 | 5/2014 | |
| WO | 2019246032 A1 | 12/2019 | |
| WO | WO-2021130144 A1 * | 7/2021 | G16H 20/70 |

OTHER PUBLICATIONS

International Search Report and Written Opinion, dated Jul. 25, 2022, PCT/US2022/022046, Applicant: Vydiant, Inc., 12 pages.
International Search Report and Written Opinion, dated Aug. 3, 2022, PCT/US2022/022045, Applicant: Vydiant, Inc., 26 pages.
Lu, "These are the occupations with the highest COVID-19 risk", Visual Capitalist articles on World Economic Forum, Feb. 20, .2020.n Retrieved on Jun. 30, 2022. Retrieved from <URL:https://www.weforum.org/agenda/2020/04/occupations-highest-covid19-risk/>entire document.
Bakker et al., "Mental health smartphone apps: review and evidence-based recommendations for future developments". JMIR mental health 3.1(2016): e4984.Jan. 3, 2016(Jan. 3, 2016). Retrieved on Jul. 17, 2022 (Jul. 17, 2022) from <https://mental.jmir.org/2016/1/e/7/>entire document.
"Methods for Measuring and Monitoring Medication Regimen Adherence in Clinical Trials and Clinical Practice" Clinical Therapeutics, vol. 21, No. 6, 1999, Kevin C. Farmer, PhD., pp. 1074-1090.
"Individual and Community-Level Risk for COVID-19 mortality in the United States", Jin Jin et al., Nature Medicine, vol. 27, Feb. 2021, pp. 264-269 plus letters.
"Mining Biomedical Text: Transfer Learning to the Rescue", Dimitris Vamvourellis et al., Institute for Applied Computational Science, Dec. 29, 2020, 9 pages.
A knowledge graph of clinical trials (CTKG), Ziqi Chen et al., www.nature.com/scientificreports, 12:4724 (2022), 14 pages.
"A systematic comprehensive longitudinal evaluation of dietary factors associated with acute myocardial infarction and fatal coronary heart disease", Soodabeh Milanlouei et al., www.nature.com/naturecommunications, 11:6074 (2020), 14 pages.
"Creating a Dietary Recommendations Knowledge Graph with Timbr", Timbr.Ai, Jul. 19, 2021, 16 pages.
"Applications of knowledge graphs for food science and industry", Weiqing Min et al., Patterns 3, CellPress Open Access, May 13, 2022, 21 pages.
"Personalized Food Recommendation as Constrained Question Answering over a Large-scale Food Knowledge Graph", Yu Chen et al., Association for Computing Machinery, Jan. 5, 2021, 9 pages.
"Personalized Food Recommendation as Constrained Question Answering over a Large-scale Food Knowledge Graph", Yu Chen et al., WSDM '21: Proceedings of the 14th ACM International Conference on Web Search and Data Mining, Mar. 8, 2021, pp. 544-552.

(56) References Cited

OTHER PUBLICATIONS

"Global burden of 369 diseases and injuries in 204 countries and territories, 1990-2019: a systematic analysis for the Global Burden of Disease Study 2019", www.thelancet.com, vol. 396, Oct. 17, 2020, pp. 1204-1222.
"HiPub: translating PubMed and PMC texts to networks for knowledge discovery", Kyubum Lee et al., Bioinformatics, 32(18), Aug. 2, 2016, pp. 2886-2888.
"Individualized Knowledge Graph A Viable Informatics Path to Precision Medicine", Peipei Ping et al., Circulation Research, Mar. 31, 2017, pp. 1078-1080.
"Consensus statement understanding health and malnutrition through a systems approach: the ENOUGH program for early life", Jim Kaput et al., Genes Nutr (2014) 9:378, Dec. 22, 2013, 9 pages.
"Knowledge Graphs and Knowledge Networks: The Story in Brief", Amit Sheth et al., IEEE Internet Computing, vol. 23, No. 4, pp. 67-84, Mar. 7, 2020.
"NETME: on-the-fly knowledge network construction from biomedical literature", Alessandro Muscolino et al., Applied Network Science (2022) 7:1, Jan. 6, 2022, 24 pages.
"HINT: Hierarchical interaction network for clinical-trial-outcome predictions", Tianfan Fu et al., Patterns 3, 100445, Apr. 8, 2022, 13 pages.
"Causal relationship extraction from biomedical text using deep neural models: A comprehensive survey", Abbas Akkasi et al., Journal of Biomedical Informatics 119 (2021) 103820, 12 pages.
"NutriChem 2.0: exploring the effect of plant-based foods on human health and drug efficacy", Yueqiong Ni et al., Database, 2017, pp. 1-6.
"NutriChem: a systems chemical biology resource to explore the medicinal value of plant-based foods", Kasper Jensen et al., Nucleic Acids Research, 2015, vol. 43, Database issue, Aug. 8, 2014, pp. D940-D945.
"Analysis of Knowledge Graph Model of Exercise Physiology Based on Computer Information Technology", Jinglian Chi, ICASIT 2021: 2021 International Conference on Aviation Safety and Information Technology, Dec. 2021, pp. 533-537.
"Visual Analysis of College Sports Performance Based on Multimodal Knowledge Graph Optimization Neural Network", Nan Zheng et al., Computational Intelligence and Neuroscience, vol. 2022, Article ID 5398932, Jul. 1, 2022, 12 pages.
"Building A PubMed knowledge graph", Jian Xu et al., Scientific Data, (2020) 7:205, Jun. 26, 2020, 15 pages.
"Discovering biomedical semantic relations in PubMed queries for information retrieval and database curation", Chung- Chi Huang et al., Database, 2016, doi: 10.1093/database/baw025, Feb. 14, 2016, pp. 1-15.
"Deep Reasoning with Knowledge Graph for Social Relationship Understanding", Zhouxia Wang et al., Jul. 2, 2018, 8 pages.
"Building and Using Personal Knowledge Graph to Improve Suicidal Ideation Detection on Social Media", Lei Cao et al., IEEE Transactions on Multimedia, vol. 24, Dec. 25, 2020, 3 pages.
Escribano, J. et al., "Effect of Protein Intake and Weight Gain Velocity on Body Fat Mass at 6months of Age:The EU Childhood Obesity Programme.", International Journal of Obesity, 36(4), 548-553. (Year:2012).
Heinz, Adrienne J., The Effects of Alcohol, Caffeine and Expectancies on Personal Agency, Impulsivity and Risk Taking: University of Illinois at Chicago, ProQuest Dissertations Publishing, 2012.3551879 (Year2012).
Yi, Weiying, Enabling Personalized Air Pollution and Health Monitoring Using Low-Cost Sensors ands Artificial Intelligence; The Chinese University of Hong Kong (Hing Kong), ProQuest Dissertations Publishing. 2021.29186266. (Year 2021).
The International Preliminary Report dated Oct. 5, 2023 from the International Patent Application No. PCT/US2022/022045.
The International Preliminary Report dated Oct. 5, 2023 from the International Patent Application No. PCT/US2022/022046 .

\* cited by examiner

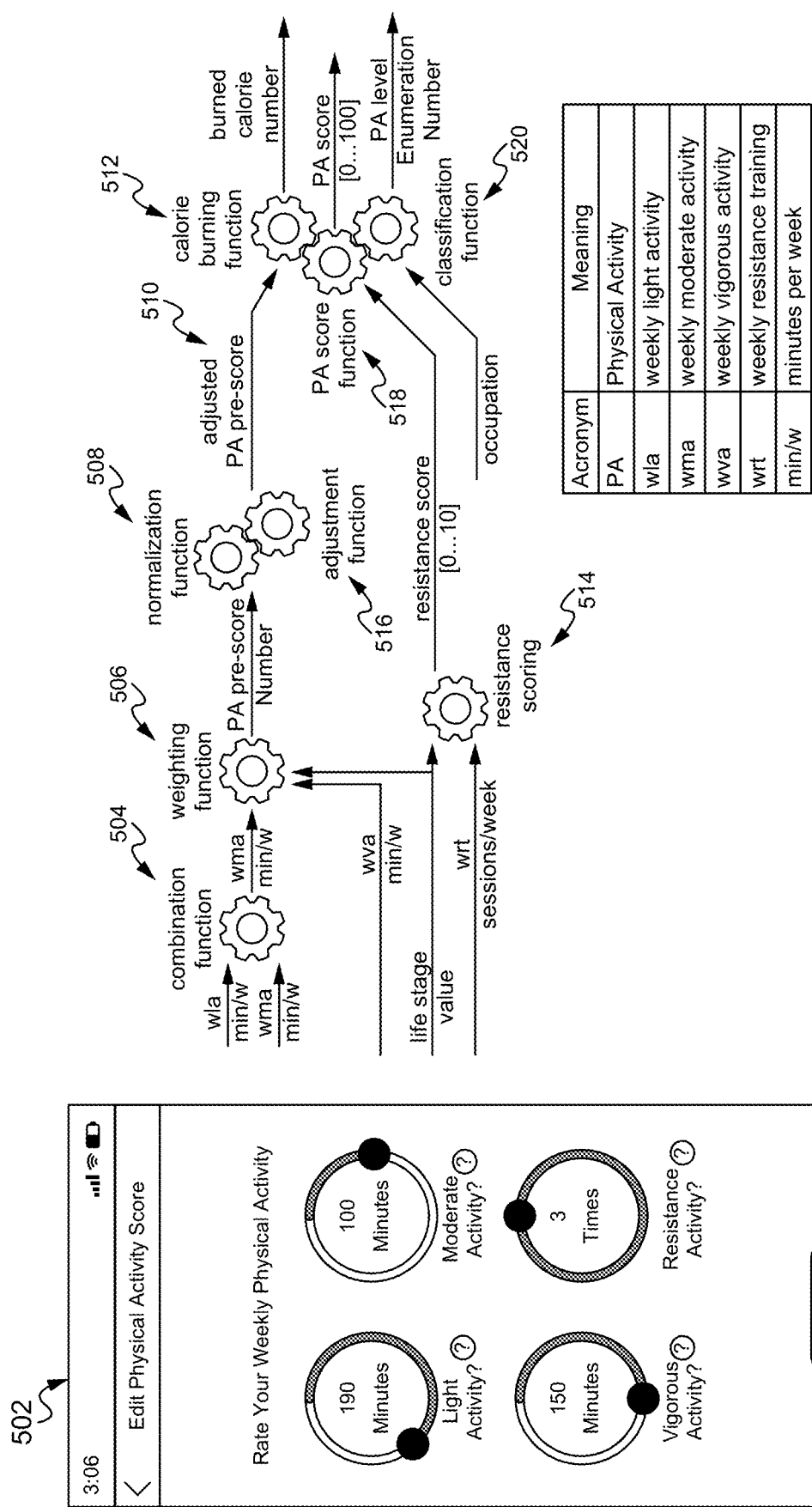

PERSONALIZED HEALTH SYSTEM, METHOD AND DEVICE HAVING A LIFESTYLE FUNCTION

RELATED APPLICATIONS

This patent application claims priority under 35 U.S.C. 119(e) of the U.S. Provisional Patent Application No. 63/166,416, filed Mar. 26, 2021, entitled "COMPREHENSIVE PATENT APPLICATION," and, U.S. Provisional Patent Application No. 63/166,427, filed Mar. 26, 2021, entitled "METHODS, DEVICES, AND SYSTEMS FOR PROTECTION AGAINST INFECTIOUS DISEASES," both of which are hereby incorporated by reference.

FIELD OF THE INVENTION

The present invention relates to the field of personal health. Specifically, the present invention relates to systems, methods, and devices for determining the impact of multiple independent and interrelated factors on human health.

BACKGROUND OF THE INVENTION

Health and disease research over the past one hundred years was largely based on reductionist experimental approaches which tested a single variable while holding all other variables constant. This methodology served science and society well, dramatically improving health and longevity. In spite of these advances, multifactorial diseases like obesity, diabetes, and other chronic diseases have become near-epidemics across the world, indicating that reductionistic strategies provide incomplete solutions. The critical concept overlooked from health research and applications is that health results from interactions of multiple in-the-body molecules and processes and many external factors that include nutrition/diet, physical activity/exercise, social activity, and environment while disease results from dysfunctions of one or more interacting processes among these scales. The interaction of the internal and external processes produces emergent (unexpected) properties of the separate macro and micro systems. However, applying these concepts experimentally or directly to the real world has not happened—economic and other disincentives and challenges have deterred integration of knowledge across these different sectors. In addition, it is only recently that advances in artificial intelligence and machine learning, and increases in "big data" computing capacity, have made it possible to harness the large volumes of data involved in digesting and analyzing immensely complex matrices of information interconnected across multiple scales and multiple morbidities.

SUMMARY OF THE INVENTION

A personal health system, method and device that maintains a health knowledge base, inputs user characteristics, generates health scores based on the user characteristics and provides recommendations based on the user characteristics, health scores and knowledge base, wherein the recommendations are indicated by the knowledge base to be likely to improve the user's health scores.

A first aspect is directed to a personal health system for promoting healthy choices to one or more users. The personal health system comprises at least one computing device including a processor and a non-transitory computer-readable medium coupled with the processor and storing a personal health platform having a user interface, wherein when executed by the processor the personal health platform is operable to provide a user input module that guides a user to input personal characteristics of the user, the personal characteristics including physical activity characteristics, social activity characteristics, sleep characteristics, nutrition characteristics and stress characteristics, generate a physical activity score based on the physical activity characteristics, a social activity score based on the social activity characteristics, a sleep score based on the sleep characteristics, a nutrition score based on the nutrition characteristics and a stress score based on the stress characteristics and determine a lifestyle score based on a combination of the physical activity score, the social activity score, the sleep score, the stress score and the nutrition score.

In some embodiments, the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity. In some embodiments, the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs. In some embodiments, the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value. In some embodiments, the sleep characteristics comprise an average nightly sleep duration and a daytime tiredness value, wherein the daytime tiredness value indicates how tired the user feels during daytime as evaluated by the user.

In some embodiments, the stress characteristics comprise an occupation of the user, a method of transport to the occupation, and a work commute distance of the user. In some embodiments, the social activity characteristics comprise an amount of time spent participating in sports, an amount of time participating in religious services, an amount of time spent with friends, an amount of time spent with family, and an amount of time spent volunteering. In some embodiments, determining the lifestyle score includes multiplying the physical activity score, the social activity score, the sleep score, the stress score and the nutrition score by separate weighting percentages, wherein the separate weighting percentages add up to 100 percent. In some embodiments, the personal health platform is operable to assign an identified condition to the user based on at least one of the physical activity score, the social activity score, the sleep score, the nutrition score and the stress score. In some embodiments, the system further comprises a health knowledge base coupled with the device, stored on a non-transitory computer-readable medium and including a plurality of tuples that each include a tuple condition a user is able to have, a factor that affects the condition, and relationship that defines how the factor affects the condition. In some embodiments, the personal health platform is operable to determine a set of the tuples whose tuple condition matches the identified condition assigned to the user, and generate a recommendation for the user based on at least one of the set, wherein the recommendation identifies the factors of the at least one of the set and whether to increase or decrease each of the factors.

A second aspect is directed to a non-transitory computer-readable medium storing a personal health platform for promoting healthy choices to one or more users, wherein when executed by a processor the personal health platform is operable to provide a user input module that guides a user to input personal characteristics of the user, the personal characteristics including physical activity characteristics, social activity characteristics, sleep characteristics, nutrition characteristics and stress characteristics, generate a physical activity score based on the physical activity characteristics, a social activity score based on the social activity characteristics, a sleep score based on the sleep characteristics, a nutrition score based on the nutrition characteristics and a stress score based on the stress characteristics and determine a lifestyle score based on a combination of the physical activity score, the social activity score, the sleep score, the stress score and the nutrition score.

In some embodiments, the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity. In some embodiments, the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs. In some embodiments, the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value. In some embodiments, the sleep characteristics comprise an average nightly sleep duration and a daytime tiredness value, wherein the daytime tiredness value indicates how tired the user feels during daytime as evaluated by the user.

In some embodiments, the stress characteristics comprise an occupation of the user, a method of transport to the occupation, and a work commute distance of the user. In some embodiments, the social activity characteristics comprise an amount of time spent participating in sports, an amount of time participating in religious services, an amount of time spent with friends, an amount of time spent with family, and an amount of time spent volunteering. In some embodiments, determining the lifestyle score includes multiplying the physical activity score, the social activity score, the sleep score, the stress score and the nutrition score by separate weighting percentages, wherein the separate weighting percentages add up to 100 percent. In some embodiments, the personal health platform is operable to assign an identified condition to the user based on at least one of the physical activity score, the social activity score, the sleep score, the nutrition score and the stress score. In some embodiments, the medium further comprises a health knowledge base stored on the non-transitory computer-readable medium and including a plurality of tuples that each include a tuple condition a user is able to have, a factor that affects the condition, and relationship that defines how the factor affects the condition. In some embodiments, the personal health platform is operable to determine a set of the tuples whose tuple condition matches the identified condition assigned to the user, and generate a recommendation for the user based on at least one of the set, wherein the recommendation identifies the factors of the at least one of the set and whether to increase or decrease each of the factors.

A third aspect is directed to a method of implementing a personal health system for promoting healthy choices to one or more users. The method comprises, with at least one computing device, providing a user input module that guides a user to input personal characteristics of the user, the personal characteristics including physical activity characteristics, social activity characteristics, sleep characteristics, nutrition characteristics and stress characteristics, generating a physical activity score based on the physical activity characteristics, a social activity score based on the social activity characteristics, a sleep score based on the sleep characteristics, a nutrition score based on the nutrition characteristics and a stress score based on the stress characteristics and determining a lifestyle score based on a combination of the physical activity score, the social activity score, the sleep score, the stress score and the nutrition score.

In some embodiments, the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity. In some embodiments, the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs. In some embodiments, the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value.

In some embodiments, the sleep characteristics comprise an average nightly sleep duration and a daytime tiredness value, wherein the daytime tiredness value indicates how tired the user feels during daytime as evaluated by the user. In some embodiments, the stress characteristics comprise an occupation of the user, a method of transport to the occupation, and a work commute distance of the user. In some embodiments, the social activity characteristics comprise an amount of time spent participating in sports, an amount of time participating in religious services, an amount of time spent with friends, an amount of time spent with family, and an amount of time spent volunteering. In some embodiments, determining the lifestyle score includes multiplying the physical activity score, the social activity score, the sleep score, the stress score and the nutrition score by separate weighting percentages, wherein the separate weighting percentages add up to 100 percent. In some embodiments, the method further comprises assigning an identified condition to the user based on at least one of the physical activity score, the social activity score, the sleep score, the nutrition score and the stress score. In some embodiments, the personal health platform is coupled with a health knowledge base coupled with the device, stored on a non-transitory computer-readable medium and including a plurality of tuples that each include a tuple condition a user is able to have, a factor that affects the condition, and relationship that defines how the factor affects the condition. In some embodiments, the method further comprises determining a set of the tuples whose tuple condition matches the identified condition assigned to the user, and generating a recommendation for the user based on at least one of the set, wherein the recommendation identifies the factors of the at least one of the set and whether to increase or decrease each of the factors.

BRIEF DESCRIPTION OF THE DRAWINGS

FIGS. 4A-4F illustrate a set of screenshots of a user interface of the personal characteristics module enabling personal data entry according to some embodiments.

FIG. 5A illustrates a screenshot of a user interface of the physical activity module enabling physical activity data entry according to some embodiments.

FIG. 5B illustrates a flow diagram showing an input, scoring and recommendation process of the physical activity module according to some embodiments.

DETAILED DESCRIPTION OF THE INVENTION

Figure 1:
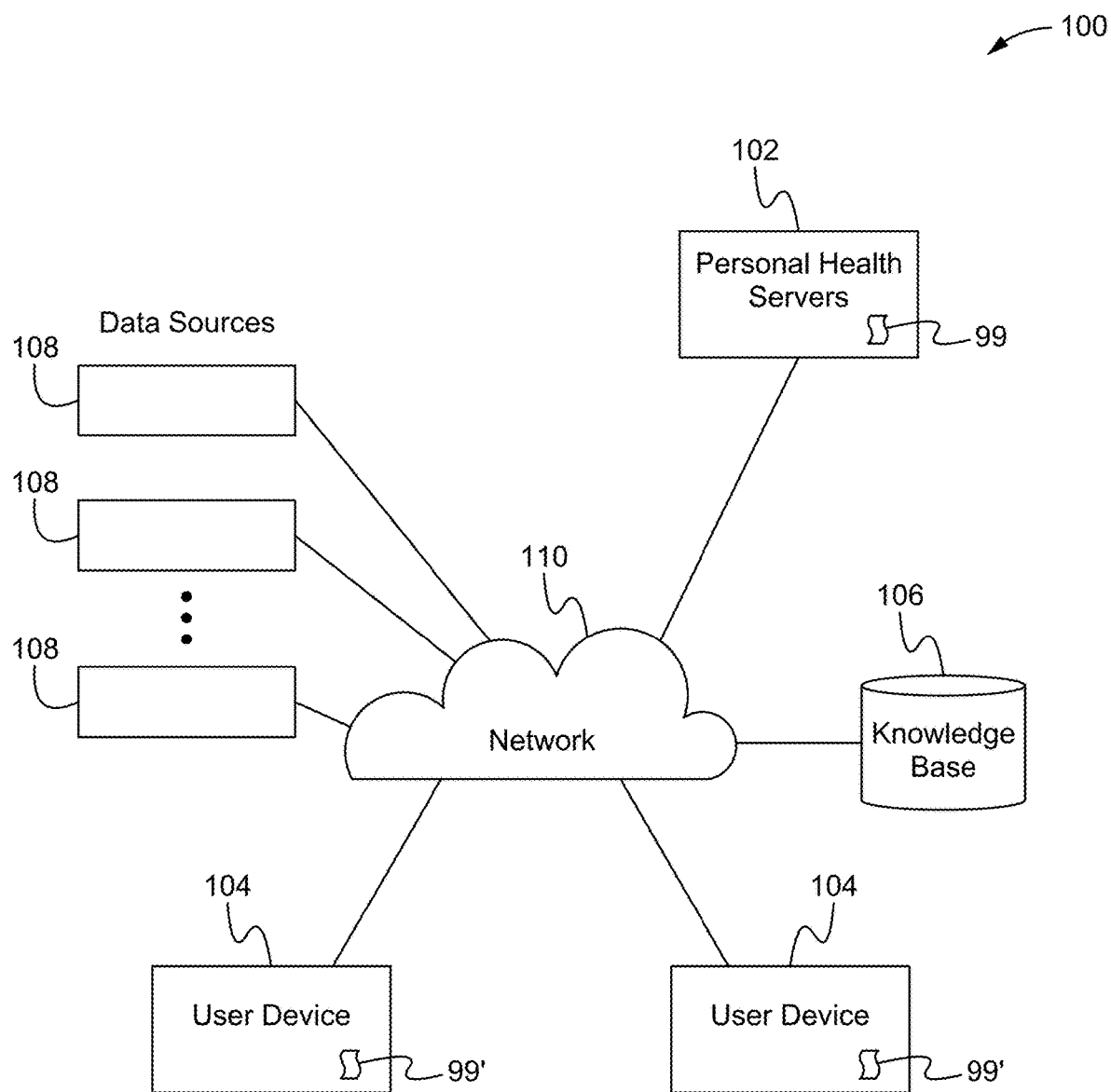
FIG. 1 illustrates a personal health system according to some embodiments.

Embodiments described herein are directed to a holistic health scoring and recommendation system comprising a deployable suite of software tools (e.g. "healthware") and databases that integrate four streams of data: (i) real-world personal data transferred from an individual (with consents) to a database (either actively transferred by entry manually or via an app or other device, or passively transferred from monitoring devices, store receipts, loyalty memberships, or similar sources), (ii) publicly or non-publicly-available environmental and social determinants of health data linked to each individual's residence or location, (iii) publicly or non-publicly-available semantic relationships among all the scales of factors discussed above and automatically extracted from unstructured, qualified sources like scientific reports and papers, clinical trials, patents, which are curated by domain experts and (iv) a system that provides personalized recommendations to the individual based on a platform knowledge base built from items (i), (ii) and (iii). As used herein, "publicly available" means any source of data other than data related to a specific individual acquired from the individual himself or herself and/or personal data from other sources (such as electronic health records, store loyalty programs, and others) which the individual allows to be transferred to the his/her account in the knowledge base.

To enhance the quality and adherence of recommendations to specific individual or group of users, in some embodiments the system is equipped with one or more scoring modules. The scoring modules that are exposed to the user of the system have a dual purpose. First, they are intended as an immediate, visual and easy to interpret index of the health status of the user that implicitly suggests what the user needs to change to improve his or her health. Second, it is used as a driver for selecting and prioritizing the recommendations that are adapted to the user by the system. As a result, the system provides the benefit of analyzing real-world user data in the context of a person's specific environment that ultimately lead to the discovery of previously undetected associations between factors and yielding better understanding of health and disease processes. To develop the right recommendations at the right time and for the right place, embodiments of the system are able to implement a ranking module of the causal relations between environment/lifestyle factors and health that are extracted from the public sources. The ranking system is intended to disambiguate contradictory health recommendations by relying on the quantity of each directional relationship between a factor and a condition, the quality of the source obtained from scientifically accepted indexes of impact factor and the type of study. The ranking system is also used to prioritize the recommendations according to specific disease outcomes. Thus, the system also provides the benefit of providing guidance for improving the health status and the quality of life of the users of the system, thereby reducing the burden on the national healthcare system.

FIG. 1 illustrates a personal health system 100 according to some embodiments. As shown in FIG. 1, the system 100 comprises one or more personal health servers 102, one or more user devices 104, a knowledge base or database 106, and one or more data sources 108 (e.g. websites, database, servers and/or other network accessible locations), all coupled together over one or more networks 110. Alternatively, the data sources 108 are able to be omitted. The networks 110 are able to be one or a combination of wired or wireless networks as are well known in the art. Although as shown in FIG. 1 one personal health server 102 is coupled with two user devices 104, one knowledge base 106 and a plurality of data sources 108, it is understood that the system 100 is able to comprise more or fewer servers 102, user devices 104, knowledge bases 106 and/or data sources 108 coupled together via the network 110.

The one or more personal health servers 102 are able to store, maintain, execute and/or operate a personal health platform 99 for providing the personal health recommendation and other features described below. In some embodiments, the entirety of the personal health platform 99 is able to be provided by the personal health servers 102. For example, the personal health platform 99 features are able to be provided in the form of one or more websites operated by the personal health servers 102. Alternatively or in addition, the personal health platform 99 is able to be in the form of a plugin that operates on top of the existing programming of one or a plurality of third party servers and/or websites (e.g. to provide added functionality to a third party website operated by the third party server). Alternatively or in addition, in some embodiments a user is able to download some or all of the personal health platform 99 from the personal health servers 102 onto one of the user devices 104, wherein the personal health platform 99 is in the form of a program, operating system, agent and/or application 99' that is able to execute locally on the user device 104 and provides some or all of the platform features described herein. In such embodiments, after being downloaded to the user device 104, the application 99' is able to use the local memory on the user device 104 to store and utilize data necessary for operation of the application 99' in an application database on the user device 104.

Alternatively, some or all of the data for operating the application 99' is able to be stored in a server database/memory on the personal health servers 102 such that the application 99' must connect to the personal health servers 102 over the networks 108 in order to utilize the data on the server database/memory necessary for some or all of the features described herein. For example, the locally executing application 99' on the user device 104 is able to remotely communicate with the personal health servers 102 over the network 110 to perform any features of the application 99', transmit data to and/or access data from the server database on the servers 102. In some embodiments, the same data are stored on both the server database and the application database such that either local or remote data access is possible for operation of the application 99'. In such embodiments, the databases are able to be periodically synchronized over the network 110.

In any case, the downloaded application 99', plugin and/or platform 99 on the personal health servers 102 together are able to provide all of the features of the personal health platform 99 by communicating via the network 108. In other words, together and/or individually the features of the personal health platform 99 described herein are able to be provided by one or more plugins, one or more websites/applications operated by the servers 102, a local application 99' on the user devices 104 or a combination thereof. Alternatively, the application and/or plugin is able to provide all of the features of the personal health platform 99 without the servers 102. Additionally, it should be noted that, for the sake of brevity, the following discussion relates to the functions and operation of the personal health platform 99 in the form of a website, application, user interface, program and/or database operating on the personal health server 102, however it is understood that the discussion is able to also relate to the function and operation of platform 99' in the form of the application/plugin, the application/plugin user interface and/or the application/plugin database such that the platform 99' performs some or all of the functions with the platform 99 performing the remainder.

The data sources 108 are able to be entities that provide and/or store data that are useful for creating the knowledge base 106. For example, data sources 108 are able to comprise servers, blockchains, databases, websites, applications, computing devices and/or other network accessible locations storing or maintaining desired data such as published literature (available publicly or via subscription), patents (domestic and/or foreign), clinical trials (reports on clinical trials), gray literature, government reports, and other types of health related information. The user devices 104 are able to be any electronic device capable of accessing network accessible locations such as the personal health server 102 and/or the knowledge base 106. For example, the user devices 104 are able to be one or more of smart phones, laptop computers, desktop computers, tablets, smart watches or other networked devices. The knowledge base 106 is able to be a collection of stored structured or unstructured data (within a memory) representing facts about the world and ways of reasoning about those facts to deduce new facts or highlight inconsistencies. For example, the knowledge base is able to include not only tables with numbers and strings, but also pointers to other objects that in turn have additional pointers. In some embodiments, the knowledge base 106 is able to be stored on an external memory separate from the servers 102 and/or user devices 104. Alternatively or in addition, some or all of the knowledge base 106 is able to be stored within a memory 204 of the servers 102 and/or user devices 104.

Figure 13:
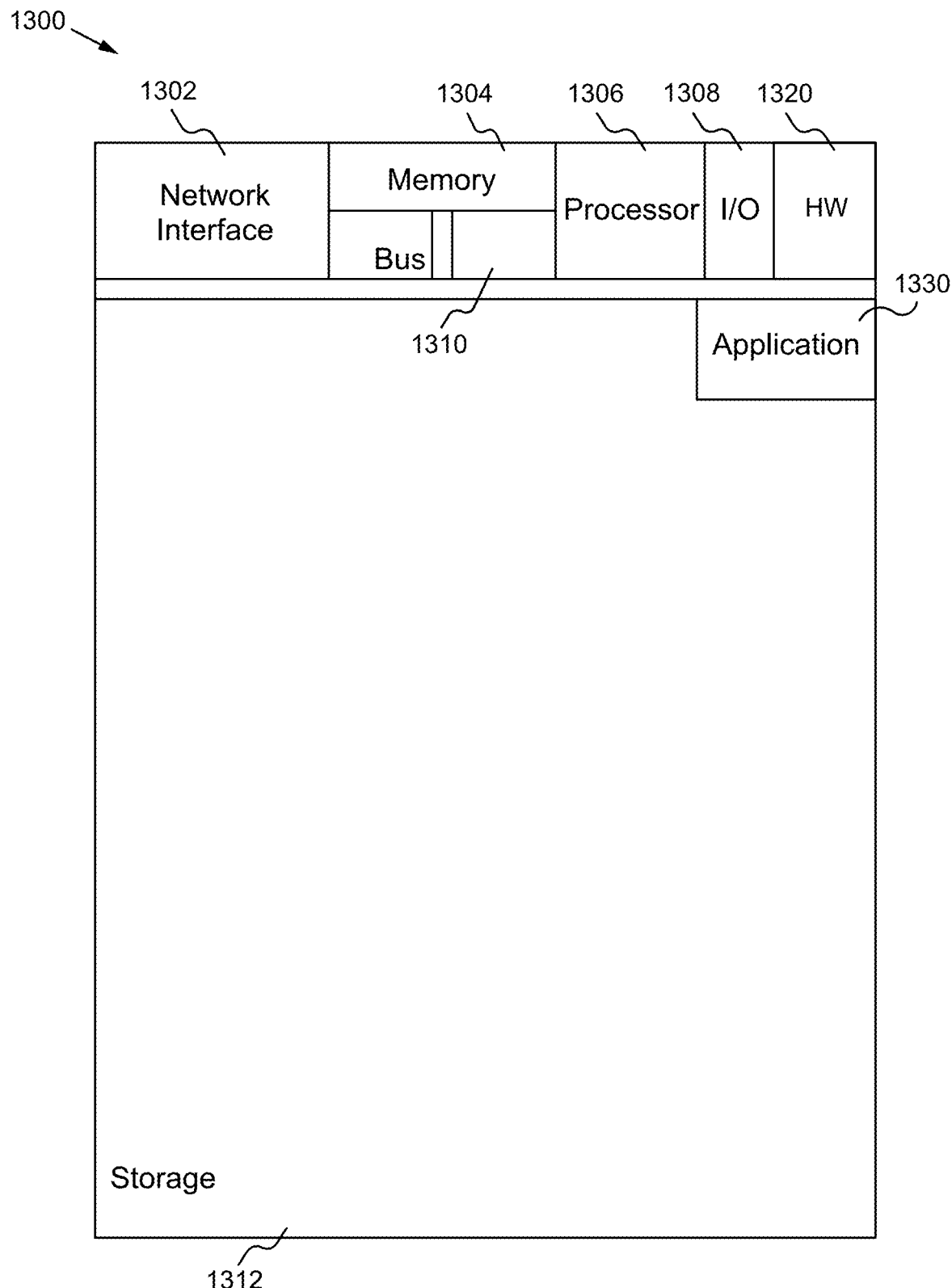
FIG. 13 illustrates a block diagram of an exemplary computing device according to some embodiments.

FIG. 13 illustrates a block diagram of an exemplary computing device 1300 according to some embodiments. The computing device 1300 is able to be one or more of the servers 102, user devices 104 and/or the data sources 108. In general, a hardware structure suitable for implementing the computing device 1300 includes a network interface 202, a memory 1304, a processor 1306, I/O device(s) 1308, a bus 1310 and/or a storage device 1312. Alternatively, one or more of the illustrated components are able to be removed or substituted for other components well known in the art. The choice of processor is not critical as long as a suitable processor with sufficient speed is chosen. The memory 1304 is able to be any conventional computer memory known in the art. The storage device 1312 is able to include a hard drive, solid state storage, network-attached storage, cloud storage, RAM, SRAM, CDROM, CDRW, DVD, DVDRW, flash memory card or any other storage device. The computing device 1300 is able to include one or more network interfaces 1302. An example of a network interface includes a network card connected to an Ethernet or other type of LAN. The I/O device(s) 1308 are able to include one or more of the following devices capable of inputting or conveying data such as a keyboard, mouse, monitor, display, printer, scanner, modem, touchscreen, button interface, speech recognition interface, and other devices.

The personal health platform 99 software, application or module(s) 1330 used to operate the personal health platform (e.g. application, plugin and/or website) are able to be stored in the storage device 1312 and/or memory 1304 and processed as applications are typically processed. More or less components shown in FIG. 13 are able to be included in the computing device 1300. In some embodiments, platform hardware 1320 is included. Although the computing device 1300 in FIG. 13 includes software 1330 and hardware 1320 for the personal health platform 99, the features of the personal health platform 99 are able to be implemented on the computing device 1300 in hardware, firmware, software or any combination thereof. Examples of suitable computing devices include a personal computer, a laptop computer, a computer workstation, a server, a datacenter, a mainframe computer, a handheld computer, a personal digital assistant, a cellular/mobile telephone, a smart appliance, a gaming console, a digital camera, a digital camcorder, a camera phone, an iPod®, a video player, a DVD writer/player, a Blu-ray® writer/player, a television, a virtual reality system, a home entertainment system or any other suitable computing device including any network-connected terminal with a screen connected to remote computing, I/O processing and data storage resources.

The Personal Health Platform

The personal health platform 99 develops and maintains a health knowledge base 106, inputs, measures and deduces individual health data, and provides a holistic health scoring and recommendations based on the user input (directly, measured or transferred from one or more third party data stores with the individual's consent), the knowledge base 106 and publicly or non-publicly-available environmental and social determinants of health data linked to each individual (e.g. from data sources 108). Specifically, users are able to use the health platform 99 to receive health related scores catered to their behavior and health as well as health recommendations for improving their health. The platform 99 is subsequently able to improve the recommendations and/or scores by identifying new health relationships based on results from identified changes in the user's behavior and applying those new health relationships in determining subsequent recommendations and/or scores.

The personal health platform 99 (as implemented by the application, plugin and/or website) is able to comprise multiple enabling capabilities, organized and referred to herein as modules. These modules are able to be implemented as discrete functional objects within a personal health platform, are able to be combined with other modules, or are able to be omitted. In some embodiments, the functions of one or more of the modules are accessible to users via a graphical user interface that is a part of the platform/modules and enables a user to input data to, receive data from and/or otherwise interact with the platform/modules.

In some embodiments, the personal health platform 99 comprises one or more of a login and registration module, a relation extraction module, a knowledge base navigation module, a personal characteristics module, a physical activity module, a social activity module, a nutrition module, a sleep module, a pathogen risk module, a digital vaccine module, a goals module, a mental health module, a lifestyle module and/or a recommendation module, wherein the platform user interface is configured to enable users to utilize the modules. Alternatively, more or less modules are able to be used and/or one or more of the modules and their functions are able to be combined into single modules or divided into multiple modules.

Login and Registration Module

The login and registration module enables a user to create an account on the platform 99 by inputting identification/contact information (e.g. username, password information, an email, passcodes, alternate contact methods, biometrics, two-factor authentication using text, voice or email and/or a security token) via the graphical user interface that is then associated with the account such that the identification/contact information is able to be used to identify the user when logging onto the platform. The identification/contact information associated with the account is able to be stored in an account database (e.g. on the servers) or another network accessible location. In some embodiments, the user account/profile data and/or any of the other data described herein is able to be encrypted and/or protected with one or more other security measures. Alternatively, the login information is able to be omitted and a user is able to use the platform without creating a user profile or logging in. After an account is created, the user is able to access the account and any data associated with the account by entering the identification/contact information in order to identify themselves to platform 99.

Relation Extraction Module

The relation extraction module generates, updates and/or manages the knowledge base 106. Specifically, the relation extraction module is able to build the knowledge base 106 by determining semantic relationships (e.g. increases, decreases, disrupts, treats, causes, complicates, co-occurs with, consists of, contains, is a derivative of, diagnoses, etc.) between health factors (e.g. personal characteristics, environment, activities, foods, food components, lifestyle, dietary supplements, or other factors described herein) and a plurality of personal health outcomes/conditions (e.g. hypertension, diabetes, triglyceride levels, obese and/or other conditions described herein or known in the art). Indeed, the conditions are able to also include those indicated by the scores described herein. For example, a low score (e.g. sleep, physical activity, social activity, nutrition, pathogen, stress) within a predetermined range (e.g. within lowest 25%) is able to correspond to a particular condition such as, but not limited to, poor sleep/insomnia, sedentary, antisocial, poor nutrition, high stress/hypertension and high risk for pathogen infection.

Figure 2:
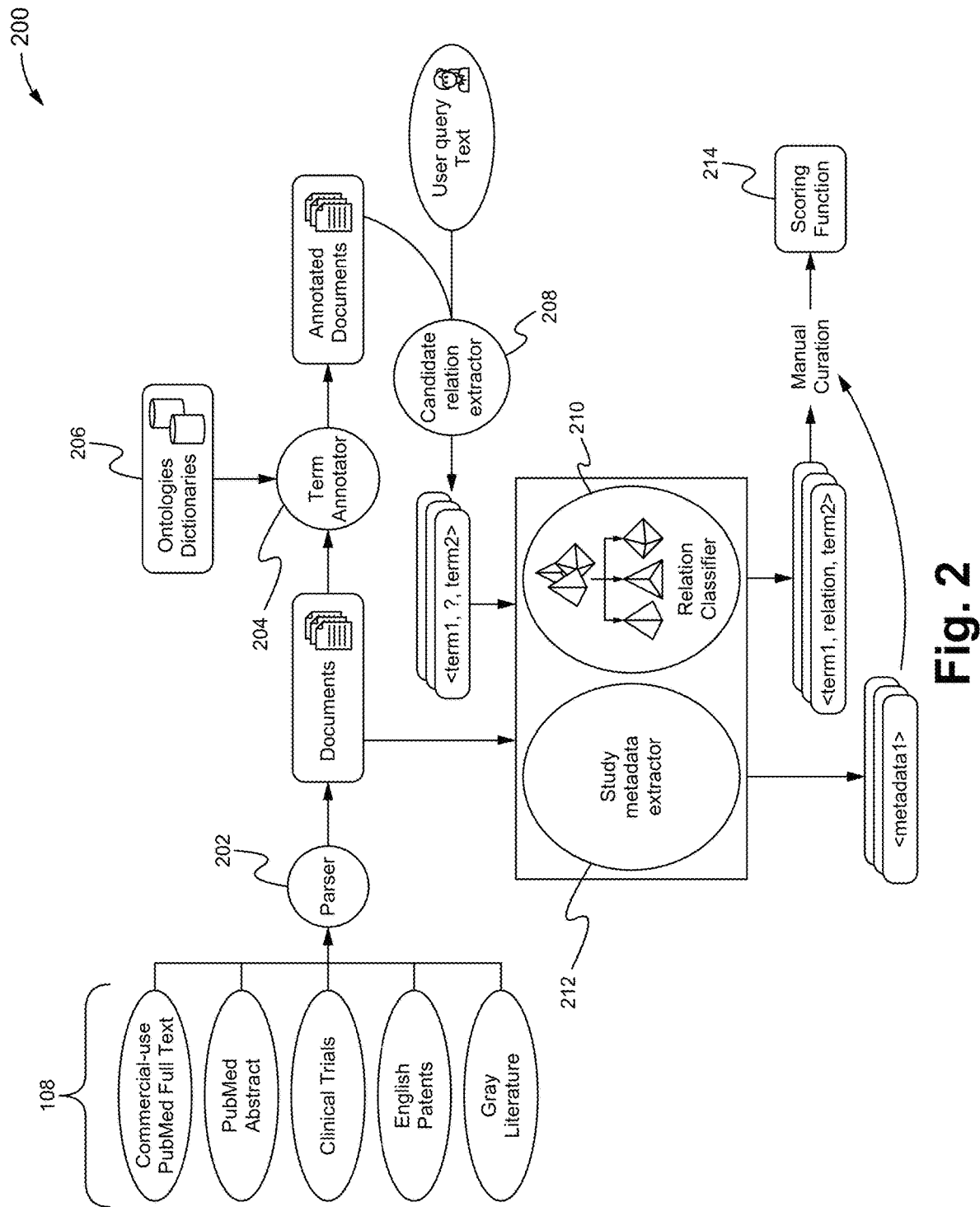
FIG. 2 illustrates a flow chart of the operation of the relation extraction module according to some embodiments.

FIG. 2 illustrates a flow chart 200 of the operation of the relation extraction module according to some embodiments. As shown in FIG. 2, the module accesses medical data from a plurality of network accessible data sources 108. For example, the sources are able to include publications in the National Library of Medicine (e.g. PubMed and similar sources), census data, patents, government reports, scientific reports and papers, gray literature, clinical trials and/or other information sources. In some embodiments, the extraction module downloads a set of health and disease information from the sources 108. Alternatively, one or more of the sources 108 are able to upload the set of health and disease information to the servers 102 operating the platform 99. After receiving the information, the module uses a parser 202 to parse the received set of information into a plurality of documents, and for each of the documents, uses a term annotator 204 to identify and annotate terms identifying health conditions and/or the factors that may affect those conditions within the documents. Specifically, the extraction module is able to comprise a plurality of ontologies/dictionaries 206 that each includes a set of health conditions and health factors such that the annotator is able to search for and identify those conditions and factors within the documents for annotation. The ontology dictionaries 206 are able to be stored in an internal database of the platform 99, accessed by the module from entities separate from the platform 99 (e.g. external websites, databases, ontology tools/programs), or both.

Furthermore, the annotation module uses available ontologies to train a model using an optimized algorithm that annotates terms in literature, government, and other sources not explicitly contained in the existing ontologies, thereby substantially expanding the recall (e.g. the sum of identified factors/conditions and synonyms thereof for these concepts) of the annotator. The conditions are able to be any condition of a person and the factors are able to be anything that affects one or more of those conditions. For example, a condition is able to be hypertension, taking medication A, good health, diabetes, trouble sleeping, have disease A, living in an area with a high walkability index, and/or combinations thereof. In some embodiments, the conditions are able to be a combined condition of both the condition itself and the current medication/treatment, wherein the combined condition is treated as a single condition that is distinguished from the condition itself with no treatment or different treatment. For example, in some embodiments a condition of Parkinson's disease, a combined condition of Parkinson's disease treated with medication A, and a combined condition of Parkinson's disease treated with medication B and C would each be considered distinct conditions for the purpose of the knowledge base 106 and the tuples described herein.

For example, the set of ontology dictionaries 206 is able to comprise but are not limited to: Foundational Model of Anatomy (human anatomy); UBERON anatomy (cross-species anatomy); Cellosaurus cell types (cell lines); Gene Ontology (molecular function, cellular component, biological process); Entrez genes (cross-species genes); Human Phenotype Ontology (phenotypic features in human disease); International Classification of Diseases, ninth revision, Clinical Modification/International Classification of Diseases, tenth revision, (clinical diagnoses); Medical subject headings (chemicals, general biomedical concepts); National Center for Biotechnology Information Taxonomy (species); National Cancer Institute Thesaurus (activity, supplements, general biomedical concepts); Food and Drug Administration drugs (medications and over-the-counter drugs); Online Mendelian Inheritance in Man 7523 (human inherited diseases); RXNORM (pharmacologic substances); LOINC (health measurements, observations, procedures); Langual/FoodOn (foods); SNOMED clinical terms (environment, social factors, clinical diagnoses); and United States Department of Agriculture (whole foods, nutrients). Additionally, in some embodiments codes used by Medical subject headings (MESH) and/or the International Classification of Diseases (ICD-10) are able to be included by mapping each of the codes to one or more terms using the term mapping available through various sources, including but not limited to, the Unified Medical Language system metathesaurus. As a further example, the module is able to include internally stored and developed ontology dictionaries 206 specific, but not limited to (i) built and virtual infrastructure, (ii) dietary patterns, (iii) natural-fitness environment, (iv) social determinants, (v) types of physical activity, (vi) mental health, (vii) stress, (viii) health behaviors, and (ix) social engagement such that the term annotator is able to identify conditions and factors in those additional fields.

After a document has been annotated, a candidate relation extractor 208 of the module is able to select statements containing pairs of a condition and a potential causal factor and submit those pairs to a relation classifier 210 for determining the semantic meaning of the relationship between the pair. In some embodiments, each statement is a sentence. Alternatively, one or more of the statements are able to be a sentence, a paragraph, a page, a chapter, a section or other division of the document. All statements containing both a condition and potential causal factor (e.g. nutrient, food, activity, environment, social determinant, behavior/engagement) are able to be presented to the classifier 210. In some embodiments, no pre-filtering of the pairs is performed before they are presented to the classifier 210.

Alternatively, one or more of the pairs are able to be filtered out before the remaining pairs are presented to the classifier 210. In some embodiments, a pair is able to be selected based on a user text query received by the platform 99 from a user via a query function provided by the platform graphical user interface. Specifically, the query is able to identify one or more factors and/or one or more conditions and the relation extractor 208 is able to identify a document including the condition and/or the factor. If both were supplied in the query and found in the document, the extractor 208 sends the pair and the related text from the document to the relation classifier 210. If only one of a factor and a condition were supplied in the query and/or found in the document, the extractor 208 identifies a pair for the factor/condition within the document in the same manner as described above and then submits that pair to the classifier 210. Alternatively, the user text query function is able to be omitted.

In any case, the classifier 210 is then able to determine the relationship between the terms of each pair using a transformers-based language model that has been pre-trained on biomedical texts. Thus, for each of the pairs, the relation classifier 210 determines a relationship between the pair thereby forming a condition, relation, factor tuple. In some embodiments, any duplicate tuples derived from the same document are discarded.

Concurrently, each of the documents are able to be submitted to a metadata extractor 212 that applies a classifier to each token (e.g. term, sub-term or group of terms) in the text of the document to identify whether the token pertains to one of several metadata classes: a population (e.g. age, sex, etc.) or type of study group (e.g. demographics of the study group); a set of interventions used (e.g. treatments; actions used in the document study); the comparator groups (e.g., disease versus control, group receiving a dietary supplement versus the group with no supplement, physical activity group versus control) and/or one or more outcomes (e.g. results of the study described in the document). Similar to the relation extractor, the metadata extractor 212 is able to be a transformers-based language model, which is then fine-tuned on internal training data. The extractor 212 then determines, for each token in a statement of the document, whether the statement belongs to one of the defined metadata classes. The set of parsed clinical study metadata is able to be associated and/or stored with each of the tuples of the document to provide context to the relationships defined by the tuples. Alternatively, the extractor 212 is able to determine the metadata of each statement individually and this statement specific metadata is able to only be associated and/or stored with the tuples derived from that statement (not other tuples derived from other parts of the document. In some embodiments, the tuples and their associated metadata are then able to be queued until they are verified by a domain specific expert who is able to curate the tuples/metadata to correct any errors. Alternatively, the manual curation is able to be omitted. In any case, in some embodiments during the recommendation processes described below, the tuples are able to be filtered (e.g. based on their metadata) to only include those that are associated with demographics, interventions and/or outcomes that match the user. This ensures that the recommendation is not based on tuples that apply to metadata that does not match the user.

Finally, each of the tuples and their associated metadata are submitted to a tuple scoring function 214 that, for each tuple, determines a document score of the document from which the tuple was determined. For example, in some embodiments the score for a document is able to be equal to a journal rank value multiplied by a weighting factor of the study type described in the document. Specifically, in some embodiments the journal rank value is able to be based on a journal ranking system (e.g. Scimago journal ranking). Alternatively, other journal ranking methods are able to be used or the journal rank is able to be omitted and the weighting factor is able to be the document score. In some embodiments, the weighting factor of the study type is able to be the values shown in Table 1 below.

TABLE 3

Weighting Factor for Scientific Studies

| Source | Factor |
|---|---|
| Adaptive Clinical Trial | 7.5 |
| Case Reports | 2 |
| Classical Article | 3.5 |
| Clinical Conference | 3.5 |
| Clinical Study | 6 |
| Clinical Trial | 8 |
| Clinical Trial, Phase I | 4 |
| Clinical Trial, Phase II | 6.5 |
| Clinical Trial, Phase III | 10 |
| Clinical Trial, Phase IV | 9 |
| Comparative Study | 8.5 |
| Congresses | 7.5 |
| Consensus Development Conference | 9 |
| Consensus Development Conference, NIH | 10 |
| Controlled Clinical Trial | 9.5 |
| Dataset | 5 |
| Duplicate Publication | 1 |
| Editorial | 5 |
| English Abstract | 5.5 |
| Equivalence Trial | 10 |
| Evaluation Studies | 7 |
| Expression of Concern | 6 |
| Government Publications | 7.5 |
| Guideline | 8 |
| Journal Article | 6.5 |
| Letter | 5.5 |
| Mendelian Randomization | 5 |
| Meta-Analysis | 10 |
| Multicenter Study | 8.5 |
| Observational Study | 5 |
| Practice Guideline | 8.5 |
| Pragmatic Clinical Trial | 9.5 |
| Publication Components | 3.5 |
| Publication Formats | 3.5 |
| Publication Type Category | 7.5 |
| Randomized Controlled Trial | 10 |
| Review | 7.5 |
| Scientific Integrity Review | 6 |
| Study Characteristics | 10 |
| Technical Report | 7.5 |
| Twin Study | 10 |
| Validation Studies | 10 |

Alternatively, other study type weighting values are able to be used, such as date of publication or study sample size, where available. In any case, the determined document score is then assigned by the scoring function 214 to each of the tuples derived from that document. In some embodiments, if duplicate tuples (e.g. having the same term pairs and relation) are found in multiple different documents, the scoring function 214 is able to average the document score of each of the documents including the tuple and assign that average value to the tuple. Subsequently, the relation extraction module is able to store the tuples along with their score (and/or clinical study metadata) in the knowledge base 106. If any of the tuples are duplicates of a tuple already found within the knowledge base 106, the score of the duplicate tuple is able to be averaged with the document scores of the documents used to determine the score of the pre-existing tuple within the knowledge base 106 in order to adjust the existing tuple score based on the duplicate tuple. This relation extraction process is able to be continually and dynamically performed by the extraction module in order to perpetually update and/or expand the knowledge base 106.

Knowledge Base Navigation Module

The knowledge base navigation module provides a user interface that enables users to extract or otherwise use data of the knowledge base 106. Specifically, the navigation module includes a network feature, a score feature and an article feature that enable users to view (in network, chart, virtual reality and/or other forms) and filter the tuples for desired factors, conditions and/or relationships as well as review the underlying text from the document supporting the relationship. In particular, a user is able to select a specific condition or conditions and the navigation module presents all of the factors that affect the specific condition(s) (or a selected subset of the factors that fall under one or more factor types selected by the user). Similarly, a user is able to select a specific factor (or factors or type of factor) and be presented with each of the conditions affected by the specific factor(s) (or set of factors within the selected factor type).

Further, each of the presented sets of factors and/or conditions are able to be further filtered by the type of factor (e.g. activity, environment, food, food component, lifestyle, dietary supplements, and/or other factor types) the type of condition (e.g. rare, common, serious, harmless, genetic, permanent, temporary, or other condition types), the type of relationship (e.g. increases, decreases, disrupts, treats, causes, co-occurs with, complicates, consists of, contains, is a derivative of, diagnosis and/or other types of relationships) and/or the strength of the relationship (e.g. the number of documents from which the relationship of the tuple was derived, or the average of document scores, as described above). In some embodiments, the navigation module enables multiple conditions to be selected such that only factors that affect all of the selected conditions are presented. Similarly, the module enables multiple factors to be selected such that only conditions that are affected by all of the factors are presented.

Figure 3A:
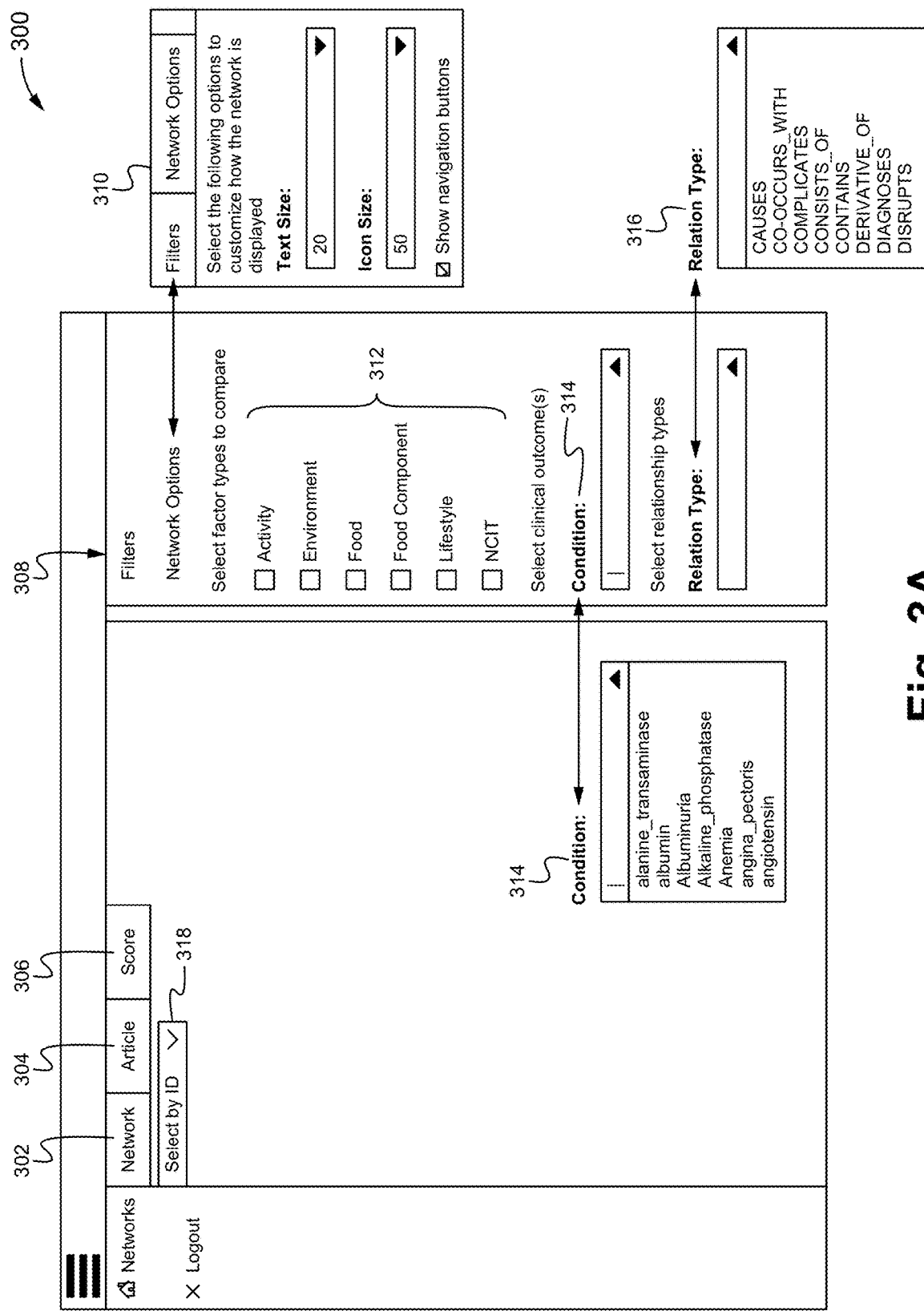
FIG. 3A illustrates a screenshot of the graphical user interface implemented by the navigation module during a selection process according to some embodiments.

FIG. 3A illustrates a screenshot of the graphical user interface 300 implemented by the navigation module during a selection process according to some embodiments. As shown in FIG. 3A, the navigation module includes a network tab 302, an article tab 304, a score tab 306, a filters tab 308 and a network options tab 310. The network tab 302 presents users with a network visualization of selected factors, conditions, relationships and/or types thereof (see FIGS. 3B and 3C) in order to provide a macro perspective of the selections. The article tab 304 presents users with a list of the documents and/or the supporting text for selected factors, conditions, relationships and/or types thereof (see FIG. 3D) in order to enable a user to inspect the source material that forms the basis of the relationships. In some embodiments, the score tab 306 presents users with a bar chart visualization of selected factors, conditions, relationships and/or types thereof (see FIG. 3E) such that it is easy to compare the relative strengths of each relationship. Alternatively, the platform 99 is able to utilize other graph and visualization methods to represent these data. The network options tab 310 enables a user to adjust the text and/or icon size of the network as shown in FIGS. 3B and 3C.

Upon selection of the filters tab 308, a user is able to select which conditions, factors and/or relationships to display (e.g. as a network, chart or the supporting text thereof). Specifically, the filters tab 308 enables one or more factors and/or conditions (e.g. fructose, hypertension, urban, etc.) to be selected from a drop-down list of factors/conditions 318, one or more types of factors (e.g. activities, environment, food, food component, lifestyle, NCIT supplement, and others) to be selected from a set of factor types 312, one or more conditions to be selected from a drop-down list of conditions 314, and one or more relationships to be selected from a drop-down list of relationships 316. In some embodiments, the factor types shown in the filter tab 308 are main topics which include a plurality of subtopics. For example, the lifestyle factor type is able to include, but not be limited to, diet type (e.g. vegan, vegetarian, gluten-free, etc.), smoking status (e.g. never-smoker, smoker, occasional smoker), social media use, and other related terms. In such embodiments, the filters tab 308 is able to enable users to select a subset of the subtopics in the selected factor type in order to further filter which of the factors/factor types are selected. Alternatively, the set of factor types 312 are able to be replaced or supplemented with a factor or factor type drop-down menu that lists all of the individual factors or factor types and enables the selection of one or more of them. In some embodiments, when multiple conditions and/or factors are selected, the navigations module is able to present the network/graph/supporting text of each of the selected conditions and/or factors separately. Additionally, in some embodiments the module enables sets of conditions and/or factors to be selected together such that only factors/conditions that affect or are affected by all of the selected sets are presented.

Figure 3B:
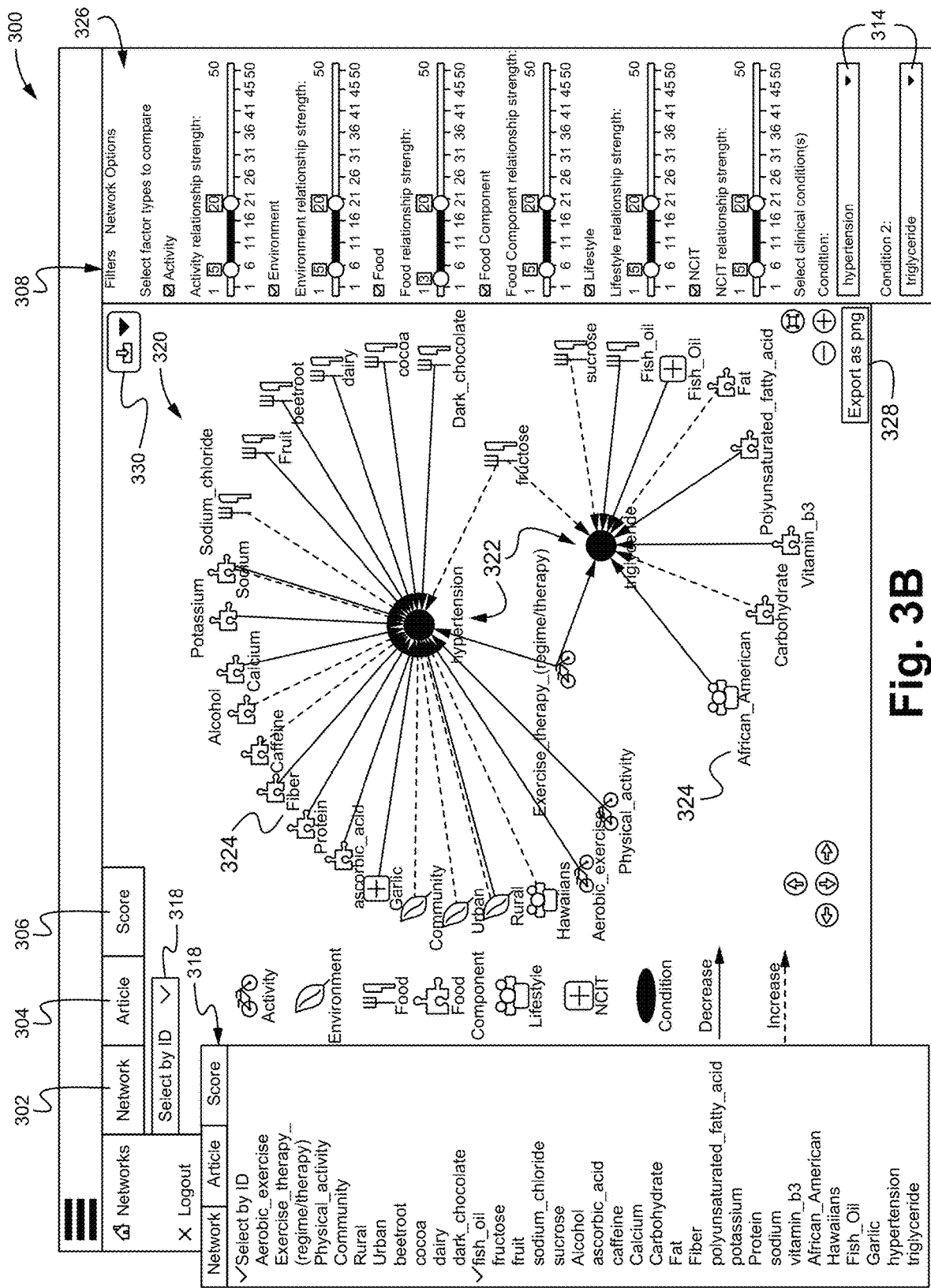
FIG. 3B illustrates a screenshot of the graphical user interface implemented by the navigation module showing a network view of two selected conditions and each of the factor types according to some embodiments.
Figure 3C:
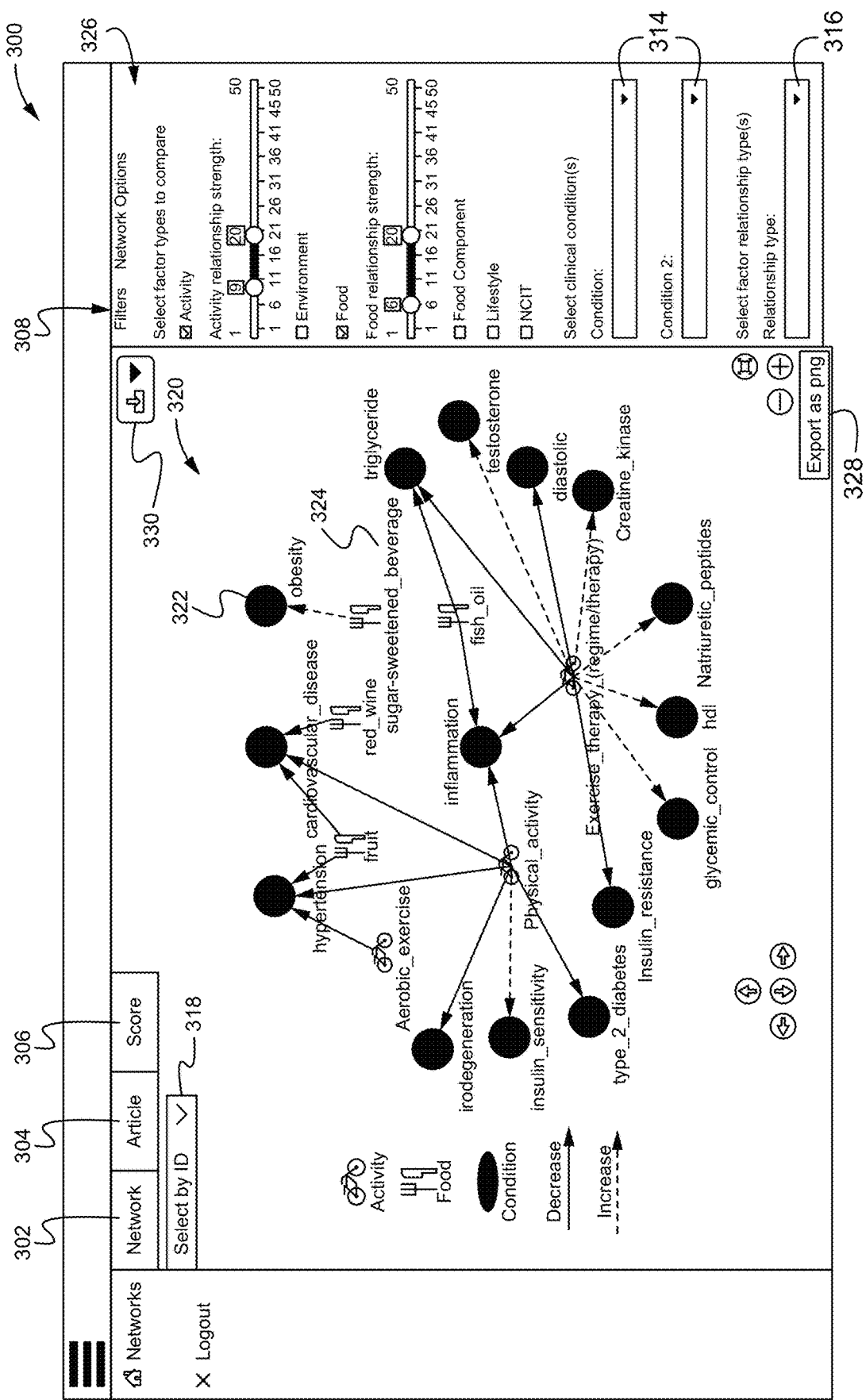
FIG. 3C illustrates a screenshot of the graphical user interface implemented by the navigation module showing a network view of two selected types of factors according to some embodiments.

FIG. 3B illustrates a screenshot of the graphical user interface 300 implemented by the navigation module showing a network view of two selected conditions and each of the factor types according to some embodiments. As shown in FIG. 3B, the navigation module is able to generate a network web 320 with each of the selected conditions 322 (e.g. hypertension and triglyceride) connected with each of the factors 324 (of the selected factor types) that affect those conditions 322. Similarly, FIG. 3C illustrates a screenshot of the graphical user interface 300 implemented by the navigation module showing a network view of two selected types of factors according to some embodiments. As shown in FIG. 3C, the navigation module is able to generate a network web 320 with each of the factors 324 that are a part of the selected types of factors (e.g. activity and food) connected with each of the conditions 322 that are affected by those factors 324. In either case, each of the connecting lines are able to include a visual indicator that indicates whether the factor 324 increases or decreases the condition 322 and each of the factors 324 are able to be labeled by their factor type (e.g. activity, environmental, food, food component, lifestyle, NCIT supplement, or other type). In some embodiments, the navigation module is further able to include a relationship strength feature 326 that displays the range of strengths of the relationships between the displayed factors 324 and conditions 322 and enables a user to adjust what ranges are displayed. For example, a user is able to specify upper and/or lower strength thresholds and the module adjusts which tuples are displayed in the network to only include those whose strength falls within the specified range.

In such embodiments, relationship strength is able to be defined as the quantity of documents from which the relationship/condition/factor tuple is derived. Alternatively, the relationship strength is able to be based on the quality of the underlying scientific documents, type of study, quantity of documents or combination thereof. Additionally as shown in FIG. 3B, after conditions, factors and/or relationships have been selected and displayed, the drop-down list of factors/conditions 318 is able to show only those factors/conditions that are being displayed. As a result, a user is able to select one or more of that set of factors/conditions to highlight (with the remaining unselected items removed, grayed out or otherwise lowlighted). Further, in some embodiments, the navigation module includes an export feature 328 and a download feature 330. The export feature 328 enables a user to export the currently presented network, chart or supporting text (e.g. as a portable network graphics format file) and the download feature 330 enables a user to download the currently presented network, chart or supporting text (e.g. as a JavaScript Object Notation file). Alternatively, the download feature 330 is able to be omitted. The positions of the icons of the network are able to be moveable for spacing or highlighting purposes. Further, a downloaded file is able to be submitted to the platform 99 which will reload it into the navigation module maintaining the last positions/displayed information of the network, chart or supporting text.

Figure 3D:
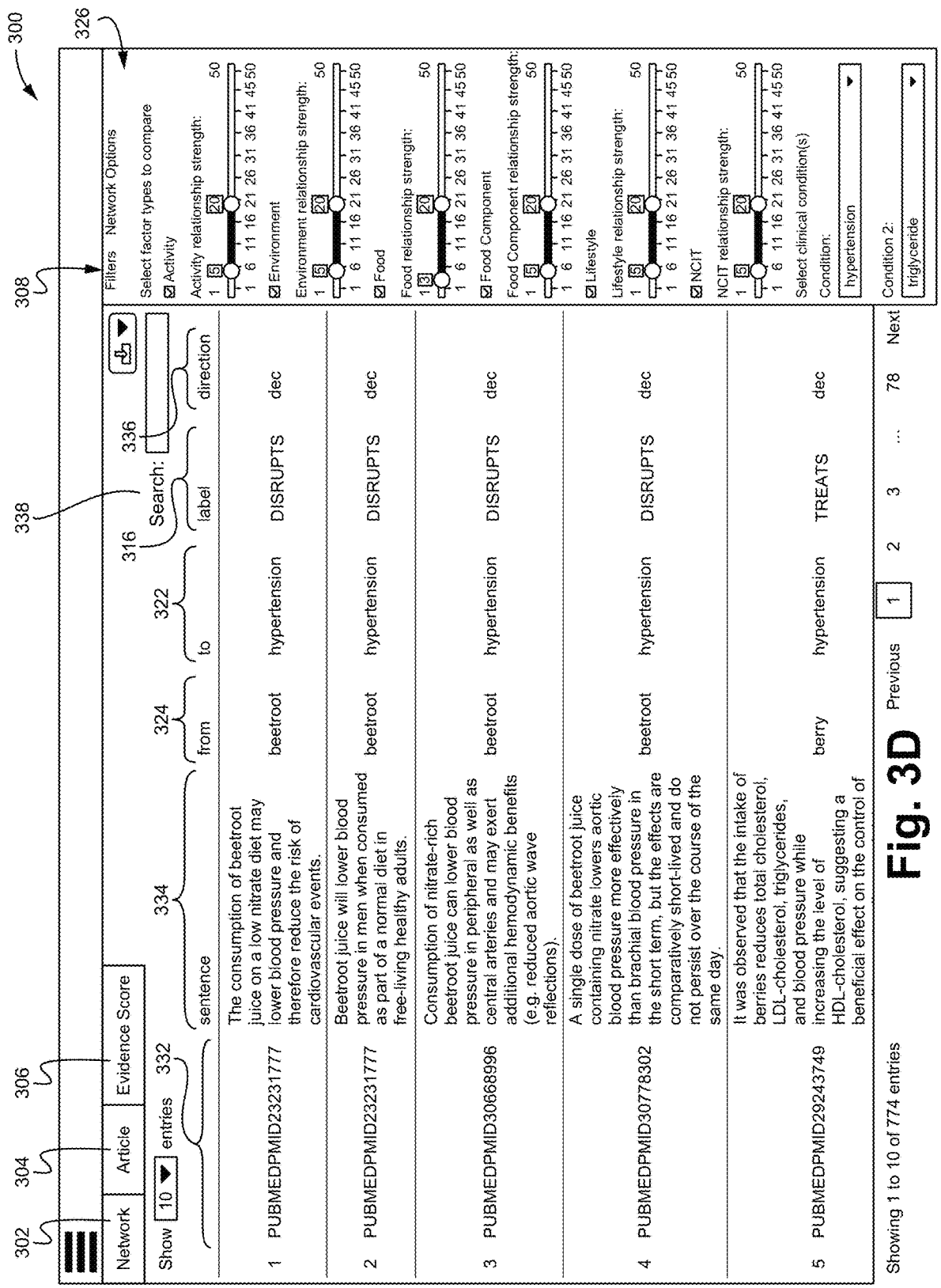
FIG. 3D illustrates a screenshot of the graphical user interface implemented by the navigation module after selection of the article tab according to some embodiments.

FIG. 3D illustrates a screenshot of the graphical user interface 300 implemented by the navigation module after selection of the article tab 304 according to some embodiments. As shown in FIG. 3D, after selection of a condition (e.g. hypertension) and/or each of the factor types, for each of the factors 324 within those factor types, the navigation module presents users with at least one document identifier 332, excerpt 334, the factor 324, the condition 322, the relationship 316 and/or the directionality of the effect 336 (e.g. increases or decreases). Specifically, for each entry, the excerpt 334 is able to be some or all of the portion of the text of the document 332 from which the relationship 316 between the condition 322 and the factor 324 was derived (e.g. the text including the factor 324, the condition 322 and/or the relationship 326). In some embodiments, the document identifier 332 is able to be a link, uniform resource locator and/or hyperlink to the entirety of the document containing the excerpt 334. Thus, the article tab 304 provides the benefit of enabling users to examine the support for any of the indicated tuples/relationships.

As also shown in FIG. 3D, when there are multiple documents supporting a tuple/relationship, the article tab 304 is able to include separate entries for each of the documents (e.g. entries 1-4 for the tuple of beetroot, hypertension, disrupts). Further, similar to FIG. 3B, the relationship strength feature 326 is able to be adjusted to narrow or increase the number of tuples/relationships shown by only including entries of those that have a strength that fits within the specified strength range for each factor type. In some embodiments, the article tab 304 is able to further include a text box search feature 338 that enables a user to narrow the list of results to those that include the searched for text (and/or a Boolean combination thereof).

Figure 3E:
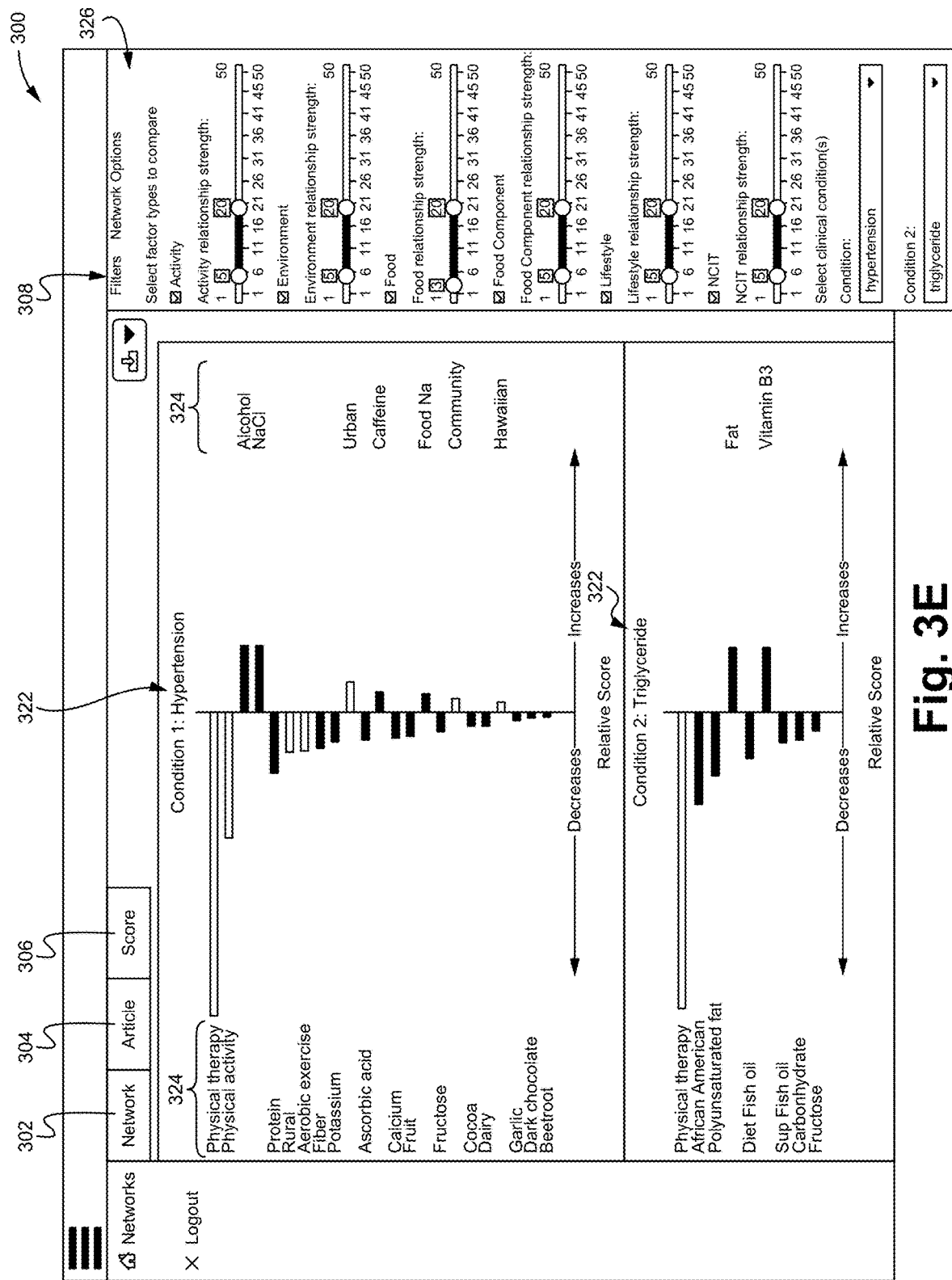
FIG. 3E illustrates a screenshot of the graphical user interface implemented by the navigation module after selection of the score tab according to some embodiments.

FIG. 3E illustrates a screenshot of the graphical user interface 300 implemented by the navigation module after selection of the score tab 306 according to some embodiments. As shown in FIG. 3E, with the same factor, factor type, condition and/or relationship selections as in FIG. 3D, under the score tab 306 the navigation module is able to display the selected tuples in a bar chart format (rather than a network format). Specifically, in this format the navigation module is able to illustrate a confidence with which each factor 324 has been shown to be positively or negatively associated with or affect each condition 322 by adjusting the size of the corresponding bar. Thus, for example, for a factor 324 that is associated with condition 322 as evidenced by a large number of documents (and/or high quality of document(s)), the size of the bar will be large compared to other factors that have less scientific evidence (in terms of quantity and quality of documents) supporting a causal relationship with the condition. As a result, the score tab 306 provides a visualization that makes it easy to compare the relative importance of each of the factors on the selected conditions.

Personal Characteristics Module

The personal characteristics module provides a user interface that prompts users with and enables the users to submit responses to personal characteristic questions such that users are to submit their personal characteristics to the platform 99 (see FIGS. 4A-4F). The characteristics module is then able to derive additional characteristics about the user based on the submitted responses including environmental parameters based on a location of the user. As a result, based on the characteristics data, the module is able to create an expanded user profile for the user as well as present health recommendations (see FIG. 4G) to the user (e.g. caloric needs, maximum alcohol intake, maximum caffeine intake). The stored personal characteristics values for each user described herein are able to be dynamically updated by the module based on newly submitted data by the user and/or data measured/input from one or more coupled devices (e.g. smart phone, smart watches). All of the characteristic data described herein is able to be stored in the user profile associated with the user by the module herein. In some embodiments, locations such as zip codes, global positioning coordinates or other location data (e.g. of the user's current residence) are used to link environmental data (e.g. public or private domain) as additional characteristic data to the characteristic data of the user, not only providing further characterization of the user, but also enabling more specific personalization of recommendations. In particular, by expanding the user submitted data with this derived location-based data, the platform 99 provides an improvement over prior art by creating a fuller picture of the user and thus enabling more customized and accurate health recommendations as described below.

In some embodiments, the graphical user interface of the module is able to prompt the user to submit characteristics such as, but not limited to: age, sex, height, weight, activity level, allergies, current conditions (vaccination statuses, current and past diseases, illnesses, disabilities and/or other physical or mental conditions, dates of onset and resolution), habits (smoking, drinking frequency/quantity, current and historical), food patterns (e.g. preferences: vegetarian, vegan, gluten free, dairy free, low carbohydrate, or other preferences), genetic background, current and/or prior prescriptions or non-prescription medications, sleep habits, social activity, peripheral device measured characteristics (e.g. heart rate, steps a day, active minutes, respiratory rate, or other sensed characteristics), occupation (past and/or present), work commute distance/method, stress habits (e.g. superior stress coper to unable to handle stress), risk of disease based on user-entered characteristics, and home zip code (or other residence location data).

Subsequently, based on the submitted characteristic data such as the zip code and/or genetic background (e.g. ancestry, race), the module is able to determine additional characteristics such as, but not limited to: air quality, blue/green space, food access, healthcare access, neighborhood, socio-economic status, transportation options, walkability, weather (current or historical), incident of pathology infections (for males, females, within selected state, within selected county, within selected age group, for selected pathogen subtype(s) and/or combinations thereof). In particular, it is noted that weather in a user's location directly affects certain conditions such as risks to pathogen infection. For example, high humidity increases transmission of respiratory pathogens, direct sunlight inactivates ribonucleic acid (RNA) viruses on surfaces and also indirectly affects pathogen transmission by changing social practices (such as, for example, cold weather increases indoor activities increasing respiratory pathogen transmission). Additionally, based on the submitted data, the characteristic module is able to calculate other characteristics (e.g. body mass index (BMI), body fat percentage, lean body mass (LBM), basal metabolic rate (BMR)) that are then added to the characteristic data for the user. In some embodiments, input and analysis of the user's genetic risk scores based on DNA sequence or genotyping data are able to provide additional information on a user's susceptibility to health conditions, response to diet or exercise, vaccine responsiveness, pathogen infectivity, eating behaviors, and other expressions of their genetic inheritance. These risk scores are able to be incorporated into the individual's overall characteristics and used for adjusting the scoring modules and therefore subsequent recommendations.

In some embodiments, the additional characteristic data are obtained from public domain sources such as, but not limited to, the American Community Survey, the USDA Food Access Database, air.gov and/or other publicly accessible databases of factors that influence health and/or disease trajectories. Data from these sources is able to be described as or linked to conditions of health as indicated in the knowledge base 106 tuples. For example, air quality is known to affect conditions such as asthma and hypertension. Access to and use of blue/green space such as parks, public open space, rivers, lakes, and seashore have been shown to reduce stress. Food deserts (lack of nutritious foods) and food swamps (excess fast foods and stores with highly processed foods) are linked to obesity, diabetes, and other chronic diseases. Neighborhood data describes the built environment such as schools, shops, gyms, crime rates, average income, and/or other amenities. Public transportation option data and walkability data are linked with and encourage more physical activity. Low socioeconomic status is associated with poor health outcomes and early death. Thus, by including one or more of these characteristics and additional characteristics into a user's profile the platform 99 provides the advantage of a more comprehensive characterization of the person allowing more targeted health recommendations.

After the characteristic data have been input, the set of personal characteristic data (including the submitted and additional characteristic data) is then able to be associated with a user profile (and/or unique user identifier), updated upon receiving updates to the submitted values from the user (prompted or unprovoked) and stored on the platform 99. As a result, the data are able to be referenced when making recommendations to the user. In particular, the characteristics module is able to use the characteristic data of each user to determine likely (future or current) conditions of the user and/or factors that are likely related to current conditions of the user. For example, if a user's characteristic data includes one or more factors that all have a relationship to one or more conditions (according to the tuples of the knowledge base 106), the module is able to determine and/or warn the user about the one or more conditions (and/or recommend changes to avoid the conditions). Similarly, if the characteristic data of a user includes a condition that they currently have (and/or taking medication for), the characteristics module is able to determine the factors that affect that condition according to the tuples of the knowledge base 106 and recommend ways to help improve the condition. Indeed, such recommendations are able to emphasize recommendations about factors that the characteristic data indicates that the user is currently engaging with so as to be personalized to that user. Further, the recommendations are able to include comparing the characteristic data of the user to the metadata associated with the tuples (e.g. if the user is within the demographics with which the tuple is associated).

Additionally, characteristic data are able to be used to exclude the user from receiving certain recommendations despite their data corresponding to the factor and/or conditions of the tuple(s). For example, the module identifies allergies indicated within the user's characteristic data, and refrains from recommending foods to which the user is allergic or activities in seasons of the year or environmental areas to which the user is allergic despite the tuples indicating that consumption of such food or participating is such activities would be beneficial to a condition of the user.

FIGS. 4A-4F illustrate a set of screenshots 402-432 of a user interface of the personal characteristics module enabling personal data entry according to some embodiments. It is understood that one or more of the types of data entered and/or the screenshots are able to be omitted, the order is able to be changed, and the platform 99 is able to operate even if a user fails to submit some of the personal data. As shown in FIGS. 4A-4F, after selecting to start at a home page 402, the user interface provides pages that enable the users to enter their birthdate 404, sex 406, height 408 and weight 410. Based on these data, the module displays their BMI 412 (i.e. BMI=weight (kg)/height (m)$^2$) along with an indication of whether their BMI indicates they may need to gain weight, lose weight, or have an acceptable weight for their size.

The user interface then continues with a health conditions page 414 that enables the users to specify if they have any health conditions (e.g. healthy, have disease A, and/or other health conditions), and if so, identify those conditions. In some embodiments, a number of conditions are listed automatically for the user to select. Alternatively or in addition, a text box is provided and a dynamic list of possible health conditions are presented to the user based on the terms they enter into the text box. For example, the module is able to perform a match or partial match search of the conditions (and/or factors) found in the knowledge base 106 for the terms entered into the text box, and then display the matching or partially matching conditions (and/or factors) to the user for selection. In some embodiments, the selectable conditions include a maternity status (e.g. pregnant, not pregnant, lactating, and/or not lactating). Alternatively, the module is able to include an additional maternity status page that enables the users to specify their current maternity status in order to ensure such a status is added to the characteristic data of their profile.

Similar to the health conditions page 414, a dietary preferences page 416 enables users to specify if they have any dietary preferences by selecting from a default list and/or searching the conditions (and/or factors) using a provided text box and then selecting from the displayed results. Also similarly, an allergies page 418 enables users to specify if they have any allergies by selecting from a default list and/or searching the conditions (and/or factors) using a provided text box and then selecting from the displayed results. In some embodiments, the module further comprises a genetics submission page that enables a user to upload their genotyping, exome sequence, genome sequence and/or other genetic data. In such embodiments, the module is able to determine and present their genetic risk score (GRS) for one or more of the conditions. Further, the GRS is able to be used in determining the personalized recommendations provided to the user as described herein.

At page 420, the module enables the users to submit their ethnicity. Specifically, the module provides boxes for the users to submit the ethnicity of one or more of the user's grandparents (if known). In some embodiments, if genotyping data is submitted, the module is able to automatically determine the user's ethnicity or ancestry based on the genotyping data. In some embodiments, the user provides their self-described cultural ethnicity. At the vaccination status page 422, the personal characteristics module enables users to specify their vaccination status for one or more conditions (e.g. flu, Covid-19, chicken pox, measles, and other conditions for which there are available vaccinations) and dates thereof. Further, in some embodiments the page 422 enables the users to list disease prevention behavior that they follow (e.g. wearing a mask, washing hands, social distancing and other activities). This vaccination status data is able to be used to provide specific recommendations based on the user's immunization status and/or behavior. At the occupation page 424, the module enables users to specify their current and/or past occupations, distance from work, and/or primary method of transportation (e.g. walk, plane, boat, bike, bus, train, subway, trolley, automobile, or other type of transportation). Like the health conditions page 414, the occupation page enables users to specify if their occupation(s) by selecting from a default list and/or searching the conditions (and/or factors) using a provided text box and then selecting from the displayed results (wherein occupations are often a factor for one or more conditions).

A smoking habits page 426 enables the users to submit data about their smoking history, such as, if they have ever smoked, if so, what dates did they smoke or start smoking and/or how much they smoke each day. Again similar to the health conditions page 414, the prescriptions page 428 enables users to specify any medications they are currently taking by selecting from a default list and/or searching the conditions (and/or factors) using a provided text box and then selecting from the displayed results. Specifically, an individual's prescription medication provides additional information on the severity and type of conditions they have. This additional information allows for increased personalization of recommendations for reducing symptoms and in some cases, reliance on those medications. The location page 420 enables a user to submit data indicating where they live. This data is able to be a zip code, an address, a city/state, global positioning coordinates and/or other ways of indicating their home location. Finally, with the self-evaluation page 432, the personal characteristics module enables users to rate themselves on a scale (e.g. 1-5) as to how healthy their diet is, how healthy their activity/exercise level is and/or how healthy their social activity is (e.g. interaction with others). In some embodiments, the module further enables the users to specify how well they handle stress (e.g. 0-5; superior stress coper, above average stress coper, average stress coper, below average stress coper, poor stress coper, unable to cope with stress). Each of the sliders provided by the user interface to enter the data are able to include an associated button (e.g. question mark) that when selected defines the type of data to which the slider relates.

Figure 4A:
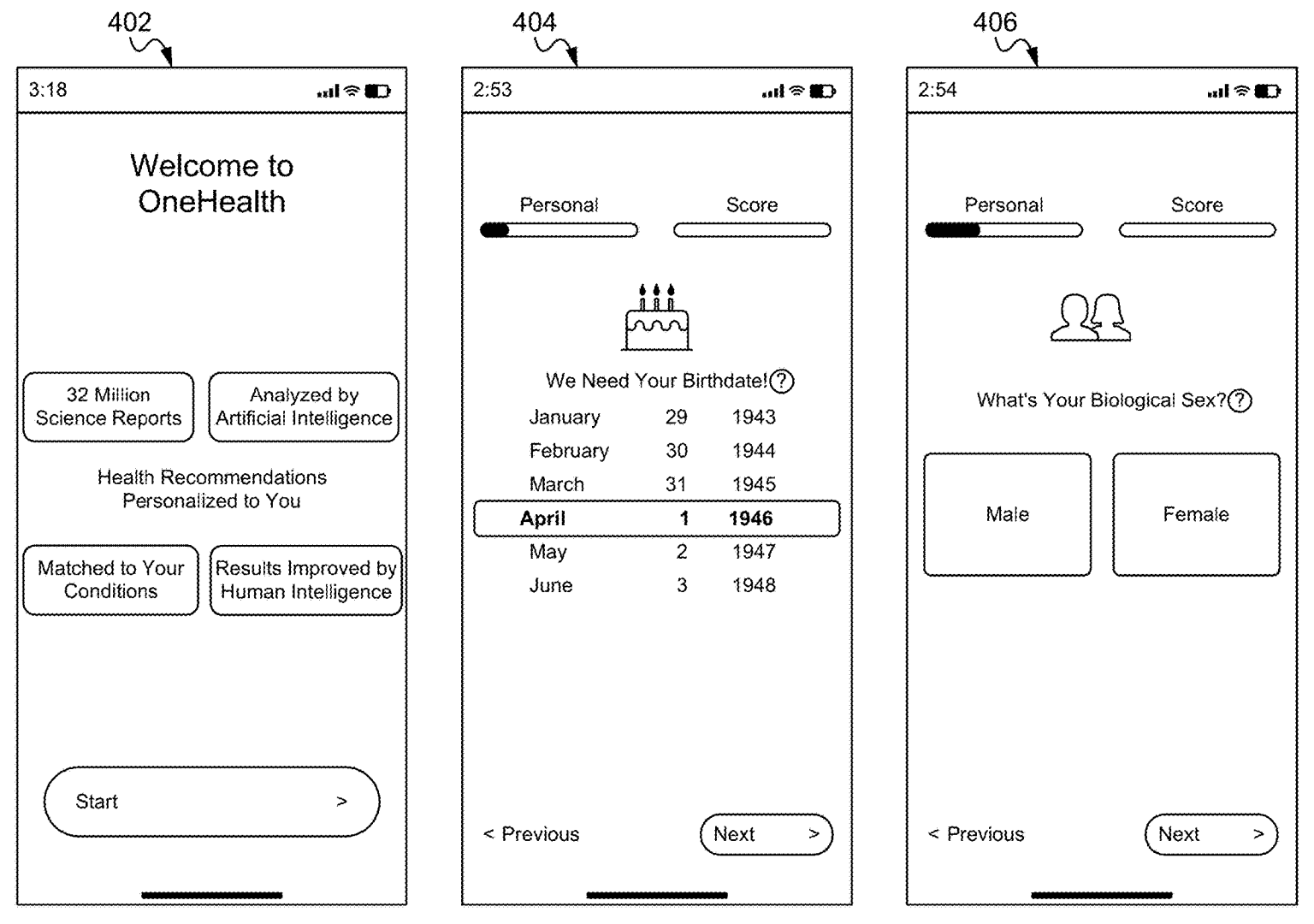
Figure 4B:
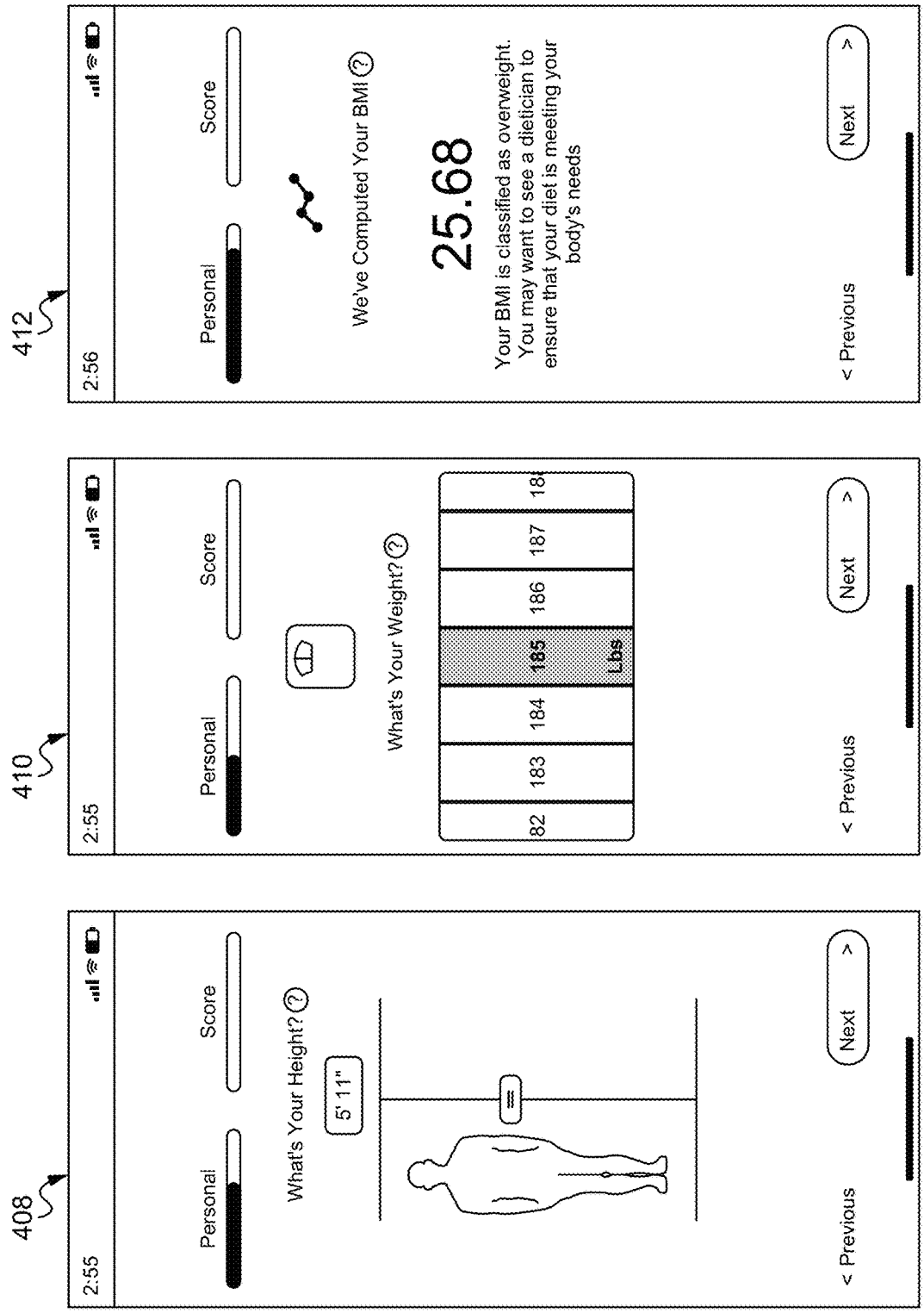
Figure 4C:
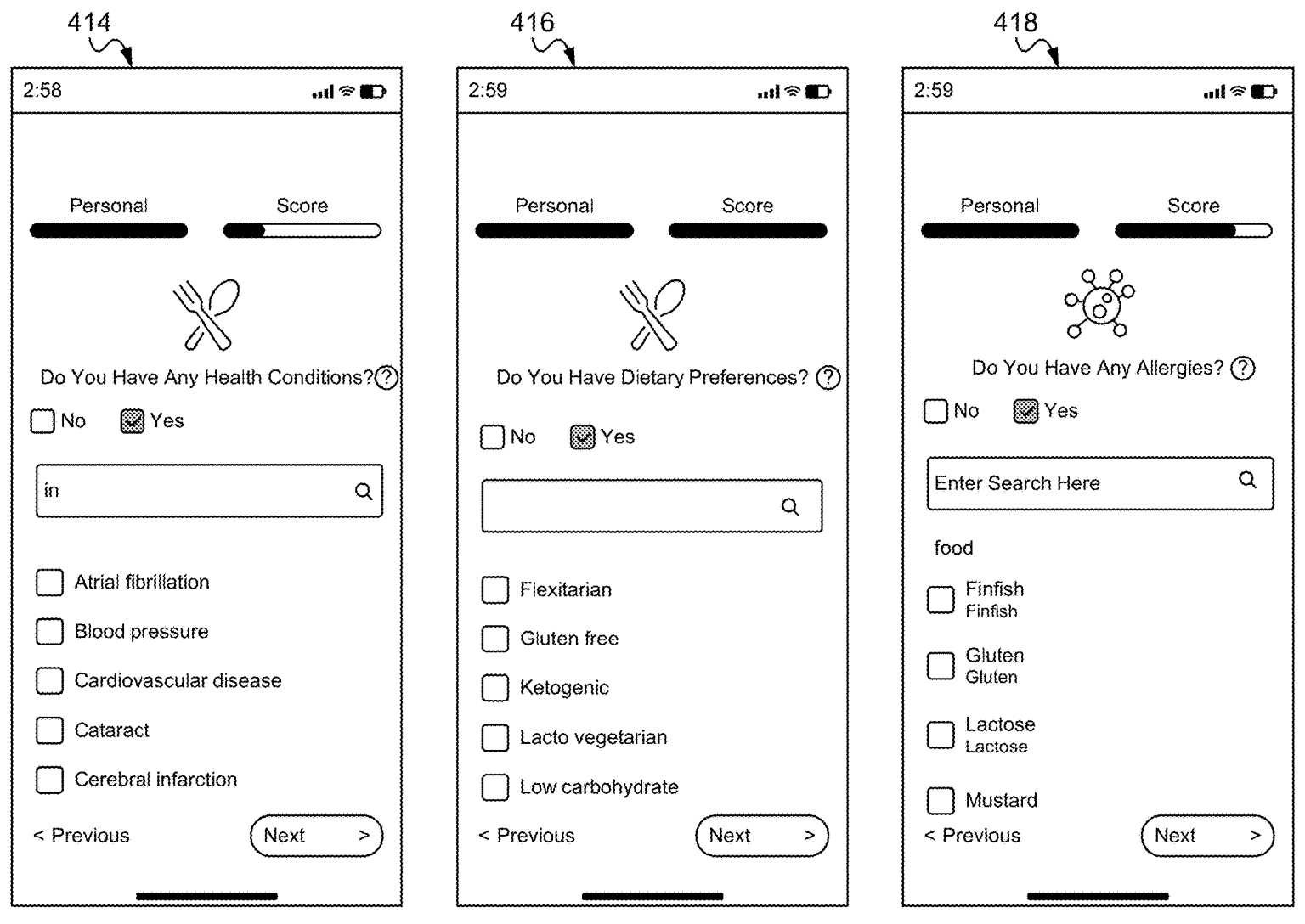
Figure 4D:
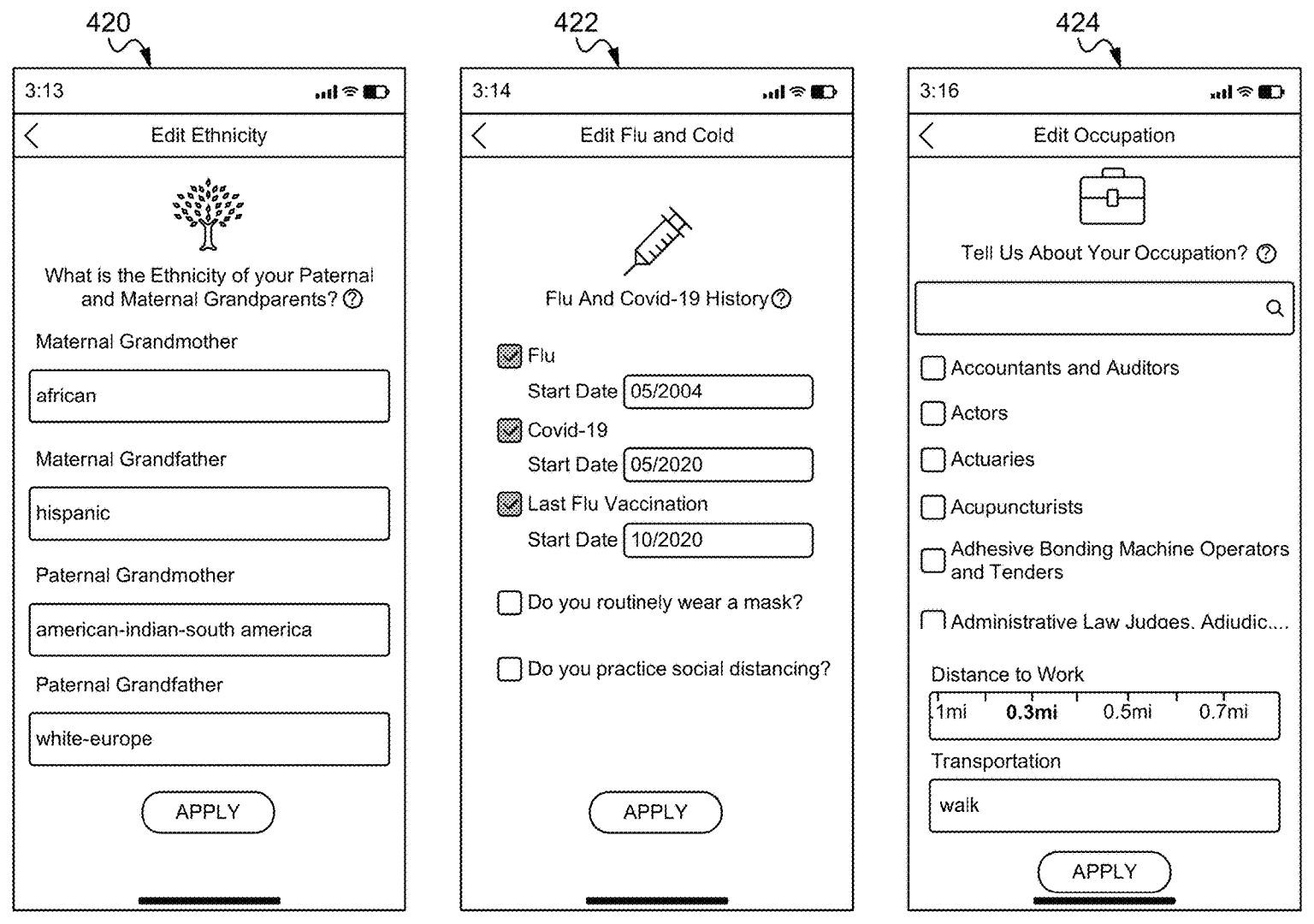
Figure 4E:
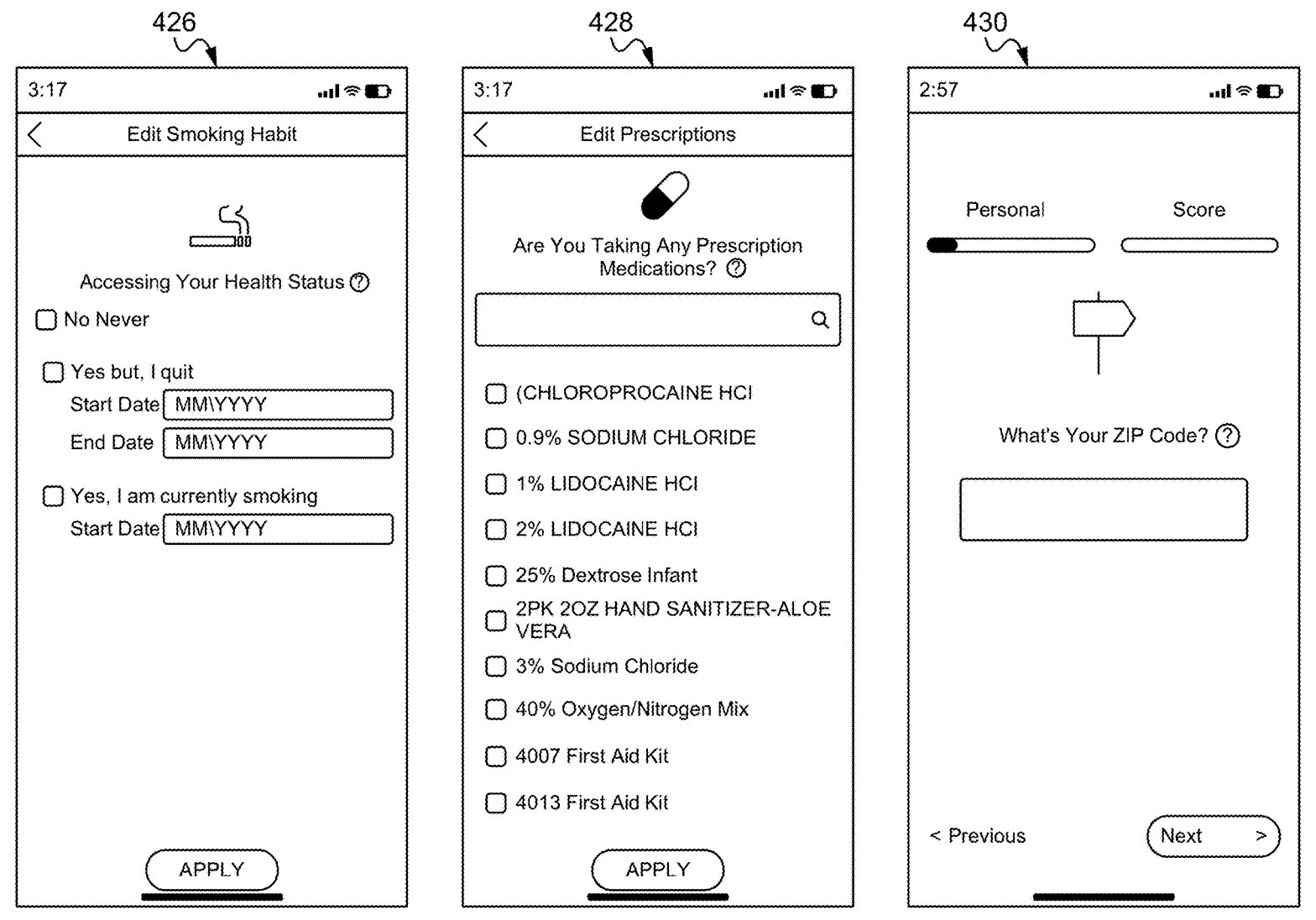
Figure 4G:
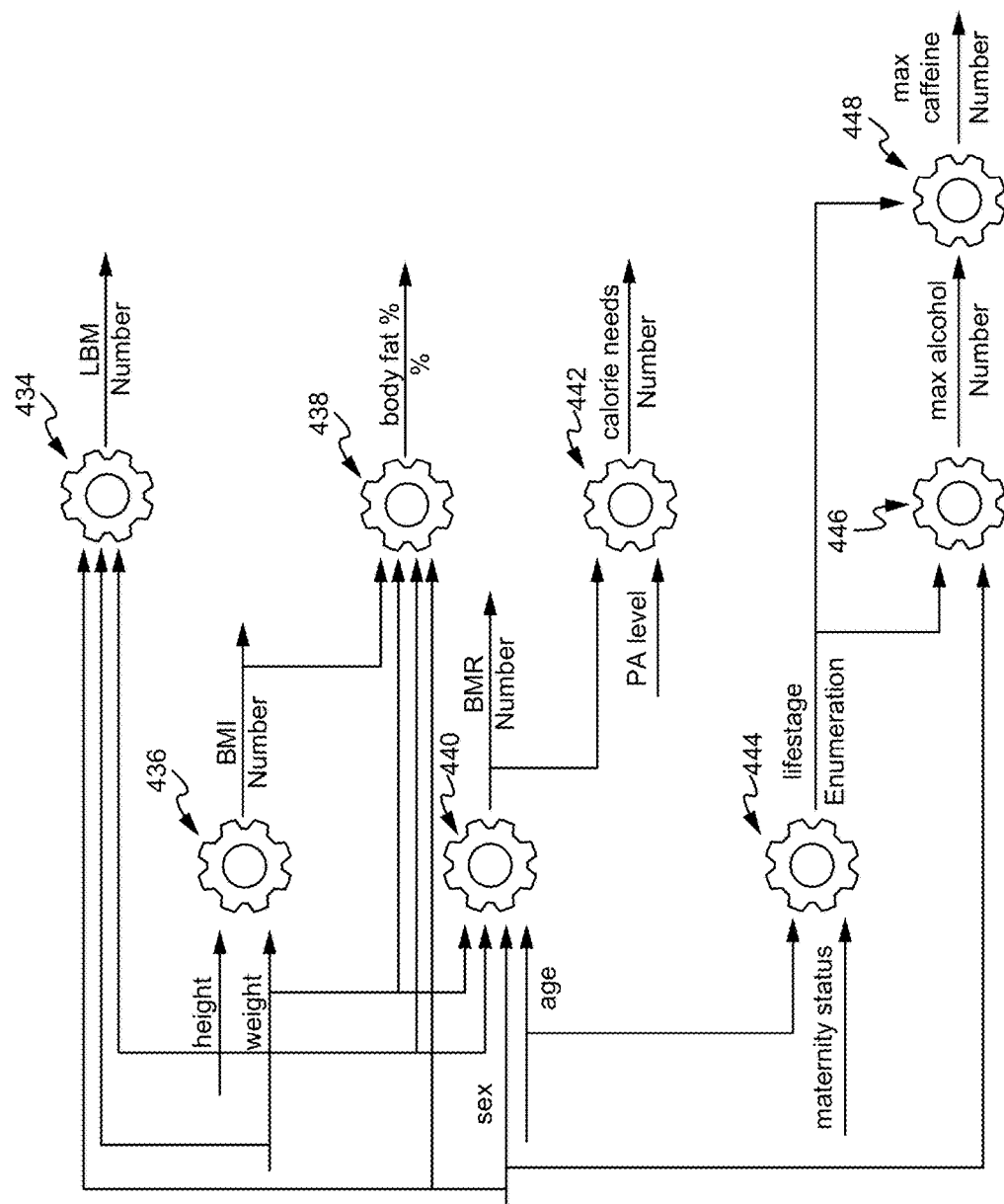
FIG. 4G illustrates a flow diagram showing an input and recommendation process of the personal characteristics module according to some embodiments.
Figure 4F:
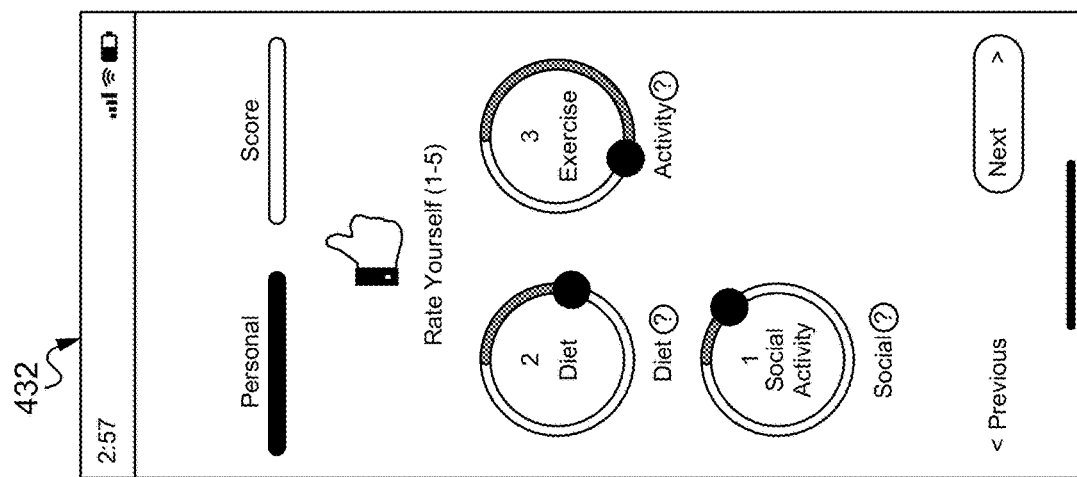

FIG. 4G illustrates a flow diagram showing an input and recommendation process of the personal characteristics module according to some embodiments. As shown in FIG. 4G, after inputting a user's personal characteristics and adding them to a user profile for the user (stored on the servers 102 and/or devices 104), the personal characteristics module is able to calculate derivable personal characteristics such as, but not limited to, BMI, lean body mass (LBM), body fat percentage, life stage status and/or basal metabolic rate (BMR) using functions 434-448 and output the characteristics to the user. These values are able to be presented to the user via the graphical user interface in order to provide them with their baseline values. Additionally, based on the input and derived personal characteristics data, the module is able to then output one or more recommendations personalized to the user, such as, a caloric needs value, a maximum alcohol consumption value and/or a maximum caffeine consumption value. Thus, the personal characteristics module provides the benefit of being able to generate a characteristics profile for each user and then use that profile to make personalized recommendations to the user about their health.

For example, in some embodiments the module is able to determine a calorie needs number or daily caloric intake needed to maintain weight (or the total daily energy expenditure (TDEE)) equal to: BMR*physical activity (PA) level value (e.g. 1.2-2.4), where PA level is determined by the physical activity module as described below. In some embodiments, the module is able to determine a maximum daily alcohol value (indicating maximum recommended number of alcoholic drinks per day) equal to: 2 drinks for adult males; 2 drinks for elderly males; 1 drink for adult females; 1 drink for elderly females and/or 0 drinks for all other life stage values. In some embodiments, the module is able to determine a maximum daily caffeine value (indicating maximum recommended number of caffeine drinks per day) equal to: 4 drinks for male or female adults; 4 drinks for male or female elderly; and/or 0 drinks for all other life stage values.

BMI is equal to weight in kilograms divided by height squared in meters. In some embodiments, LBM is able to be equal to: for men=0.407*weight [kg]+0.267*height [cm]-19.2; and for women=0.252*weight [kg]+0.473*height [cm]-48.3. In some embodiments, body fat percentage is able to be equal to: $-44.988+(0.503*age)+(10.689*gender)+(3.172*BMI)-(0.026*BMI^2)+(0.181*BMI*gender)-(0.02*BMI*age)-(0.005*BMI^2*gender)+(0.00021*BMI^2*age)$, where gender equals 0 if sex is male or equals 1 if sex is female. In some embodiments, BMR is able to be equal to: initial value=(10*weight+6.25*height-5*age), and if initial value >0 and sex is male BMR equals the initial value plus 5, or else if initial value is greater than 161 and sex is female, BMR equals the initial value minus 161. In some embodiments, the life stage status is able to be equal to: pregnant (for all females indicating the pregnant condition); lactating (for all females indicating the lactating condition); child (for ages 0-11 not pregnant or lactating); adolescent (for ages 12-17 not pregnant or lactating); adult (for ages 18-65 not pregnant or lactating); and elderly (for ages >65 not pregnant or lactating).

In some embodiments, as described above, analysis of the user's genetic risk scores based on input genetic data (e.g. DNA sequence or genotyping data) are able to provide additional information on a user's response to dietary components. These risk scores are able to be incorporated into the individual's overall characteristics and used for adjusting the scoring modules and therefore subsequent recommendations.

Physical Activity Module

The physical activity module provides a user interface that prompts users with and enables the users to submit responses to physical activity questions such that users are to submit their physical activity data to the platform 99 (see FIG. 5A). The physical activity module is then able to determine and present to the user an average physical activity (PA) score value, a PA level value and/or an average calories burned a day value for the user based on the submitted responses and the user's characteristic data (e.g. occupation, life stage status). These physical activity values are then able to be added to the user profile of the user and/or be dynamically updated by the module based on newly submitted data by the user and/or data measured/input from one or more coupled devices (e.g. smart phone, smart watches). As a result, the physical activity module provides the benefit of helping users move towards the right level of physical activity depending on their current life stage.

FIG. 5A illustrates a screenshot of a user interface of the physical activity module enabling physical activity data entry according to some embodiments. As shown in FIG. 5A, the user interface provides a physical activity page 502 that enables the users to submit their weekly physical activity. Specifically, the page 502 provides one or more sliders that enable the users to enter one or more of: the number of minutes of light activity per week; the number of minutes of moderate activity per week; the number of minutes of vigorous activity per week; and/or the number of resistance activity sessions (e.g. weight training) per week. Light activity is able to be defined as non-sedentary waking behavior that requires less than 3.0 metabolic equivalent of tasks (MET), where 1 MET is the rate of energy expenditure while sitting at rest. Examples include walking at a slow or leisurely pace (2 mph or less), cooking activities, or light household chores.

Moderate activity is able to be defined as 3.0 to less than 6.0 METs. Examples include walking briskly (2.5 to 4 miles per hour), playing doubles tennis, or raking the yard. Vigorous activity is able to be defined as 6.0 or more METs. Examples include jogging, running, carrying heavy groceries or other loads upstairs, shoveling snow, or participating in a strenuous fitness class. Resistance activity (or weight training) is able to be defined as activities that cause the body's muscles to work or hold against an applied force or weight. These activities often involve lifting relatively heavy objects, such as weights, multiple times to strengthen various muscle groups. These activities can also be done by using elastic bands or body weight for resistance (climbing a tree or doing push-ups, for example). As a result, the physical activity module provides the benefit of enabling a user's occupation, life stage and/or a plurality of different types of physical activity to be considered when determining a user's activity level and/or calories burned a week (and thus their allowable caloric intake per week as described above in relation to FIG. 4G). In some embodiments, each of the sliders are able to include an associated button (e.g. question mark) that when selected defines the type of physical activity to which the slider relates.

FIG. 5B illustrates a flow diagram showing an input, scoring and recommendation process of the physical activity module according to some embodiments. As shown in FIG. 5B, after inputting a user's weekly light and moderate activity via the input page 502, the module determines a combined light/moderate activity value with a combination function 504. Specifically, the combined light/moderate activity value is able to be equal to the reported moderate activity time, or if zero moderate activity time was reported, a combined light/moderate activity value that is equal to half of reported light activity time. The module is then able to use this combined light/moderate activity value along with the input life stage of the user and the reported weekly vigorous activity to determine a preliminary PA score for the user with a weighting function 506. For example, if the life stage value is children or adolescent, the preliminary PA score is able to equal [0.24*the combined light/moderate activity value+ 0.48*min/week of vigorous activity]; if the life stage value is adult, the preliminary PA score is able to equal [0.33*the combined light/moderate activity value+0.67*min/week of vigorous activity]; if the life stage value is elderly (e.g. 65 or older), the preliminary PA score is able to equal [0.67*the combined light/moderate activity value+1.33*min/week of vigorous activity]; if the life stage value is pregnant or lactating, the preliminary PA score is able to equal [0.67*the combined light/moderate activity value]. Alternatively, other weighting values and/or metrics are able to be used for the weighting function 506.

The physical activity module is then able to apply a normalization function 508 to the preliminary PA score. Specifically, the normalization function 508 caps the preliminary PA pre-score at 80 for adults, elderly, children and adolescents and at 90 for pregnant or lactating users. Thus, the weighting function 506 and the normalization function 508 work together to produce a normalized preliminary PA score having maximum of 80 for: adults who do at least 300 min/week of moderate activity or 150 min/week of vigorous activity and that mix moderate and vigorous activity; and elderly that do at least 150 min/week of moderate activity or 75 min/week of vigorous activity and that mix moderate and vigorous activity. Subsequently, an adjustment function 516 adjusts the normalized preliminary PA score to penalize users who do not perform both moderate and vigorous activity and reward users whose score was lowered by the normalization function 508. For example, the adjustment function 516 is able to determine an adjusted PA score by: subtracting 10 from the normalized preliminary PA score of adults, elderly, children and adolescents that have zero moderate or vigorous activity; adding 10 to the normalized preliminary PA score for adults, elderly, children and adolescents whose preliminary PA score was greater than 80; and/or adding 10 to the normalized preliminary PA score for pregnant or lactating users whose preliminary PA score was greater than 90.

Concurrently, the module is able to use a resistance function 514 to determine a resistance score for each user. For example, the resistance function 514 is able to assign 5 points per session per week (with a cap at 10 points) for adults and assign 10 points for elderly, children and adolescents if they perform at least one session per week. In some embodiments, no points are assigned to pregnant or lactating females who do resistance training. Finally, a PA score function 518 is able to sum the adjusted PA score with the resistance score to determine a PA score for the user that is presented to the user as a reflection of their current physical activity level. In some embodiments, the PA score ranges from 0 to 100 in order to enable a user to more easily understand the magnitude of the physical activity.

In some embodiments, the physical activity module is able to also include a classification function 520 that classifies the user into a PA level of vigorously active, moderately active, lightly active or sedentary. For example, an individual is classified as vigorously active if they do: at least 250 min/week of vigorous activity; or at least 300 min/week of moderate activity with at least 150 min/week of vigorous activity and at least 3 resistance sessions per week. An individual is classified as moderately active if they do: at least 300 min/week of moderate activity; at least 150 min/week of vigorous activity; or at least 150 min/week of moderate activity with at least 75 min/week of vigorous activity and 2 resistance sessions per week. An individual is classified as lightly active if they do: at least 150 min/week of light activity; at least 75 min/week of moderate activity; at least 37 min/week of vigorous activity; or at least 1 resistance session per week. If none of the above applies, the person is classified as sedentary. Additionally, in some embodiments the physical activity module stores a table that identifies one or more occupations as either a physical job or a professional athlete. In such embodiments, the classification function includes two additional classification categories of professional athlete and physical job holder. Further, the classification function 520 determines if the table indicates that the occupation submitted by the person to the personal characteristics module is a physical job or a professional athlete, and assigns the user to that category (e.g. physical job or professional athlete) if it does. In some embodiments, this occupation based classification overrides any other of the classifications that the user fits within such that, for example, a user that fits within the vigorously active classification but has a physical job, is classified in the physical job category instead of the vigorously active category.

Each of these classification categories are associated with a PA level value, which is used by the personal characteristics module to determine the recommended number of calories for the user (as described above in reference to FIG. 4G). In some embodiments, the category sedentary has a PA level value of 0.5-1.5 (e.g. 1.2), the category lightly active has a PA level value of 0.5-1.5 (e.g. 1.375), the category moderately active has a PA level value of 1.0-2.0 (e.g. 1.55), the category vigorously active has a PA level value of 1.0-2.0 (e.g. 1.725), the category physical job has a PA level value of 1.5-2.5 (e.g. 1.9), and the category professional athlete has a PA level value of 2.0-3.0 (e.g. 2.4). Alternatively, other PA values for one or more of the categories are able to be used.

In some embodiments, the physical activity module is able to also include a calorie burning function 512 that determines a burned calorie number indicating the number of calories the user burns on average in a week. Specifically, each of the types of activity (light, moderate, vigorous, resistance) input by the user using the interface 502 are associated with a metabolic equivalent of task (MET), wherein light activity has a MET of 2.0, moderate activity has a MET of 5.0, vigorous activity has a MET of 8.0 and resistance training has a MET of 5.0. Based on these MET values and the input weekly physical activity of the user, the calorie burning function is able to determine and present to the user their burned calorie number. For example, the burned calorie number is able be equal to [weight*((2.0*hours of light activity)+(5.0*hours of moderate activity)+(8.0*hours of vigorous activity)+(5.0*hours of resistance activity))]. In some embodiments, the calorie burning function 512 is able to determine and present both the burned calorie number per week, as well as the burned calorie number per day (i.e. the burned calorie number divided by 7). Additionally, as described above, the platform 99 is able to identify ranges of PA scores and/or the classifications to be associated with one or more conditions (e.g. overactive, sedentary), such that having a PA score in the range indicates the associated condition. For example a PA score in a low range (e.g. 0-10) would indicate an associated condition of poor health or sedentary that is able to be used by the recommendation module as a condition of the user based on their PA score.

In some embodiments, as described above, analysis of the user's genetic risk scores based on input genetic data (e.g. DNA sequence or genotyping data) are able to provide additional information on a user's response to specific types of exercise (e.g., resistance training versus aerobic activities or types of aerobic activities). These risk scores are able to be incorporated into the individual's overall characteristics and used for adjusting the scoring modules and therefore subsequent recommendations.

Thus, the physical activity module provides the benefit of enabling users to quantify their physical activity and determine if more or less physical activity is advisable.

Social Activity Module

Figure 6A:
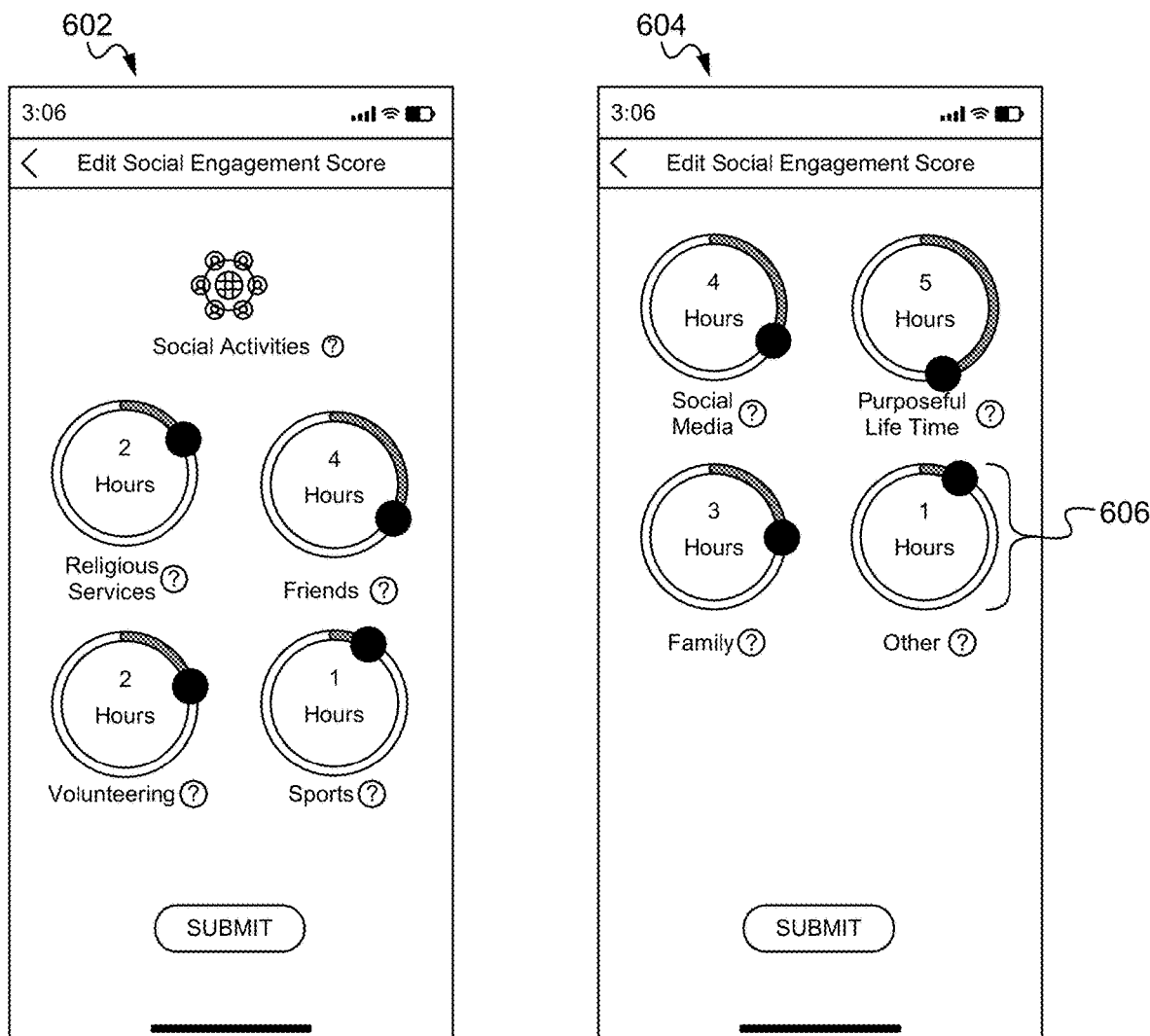
FIG. 6A illustrates a screenshot of a user interface of the social activity module enabling social activity data entry according to some embodiments.

The social activity module provides a user interface that prompts users with and enables the users to submit responses to social activity questions such that users are to submit their social activity data to the platform 99 (see FIG. 6A). The social activity module is then able to determine and present to the user a social activity (SA) score value for the user based on the submitted responses and the user's characteristic data (e.g. age). This social activity data and/or score is then able to be added to the user profile of the user and/or be dynamically updated by the module based on newly submitted data by the user and/or data measured/input from one or more coupled devices (e.g. smart phone, smart watches). As a result, the social activity module provides the benefit of helping users move towards the right level of social activity depending on their age.

FIG. 6A illustrates a screenshot of a user interface of the social activity module enabling social activity data entry according to some embodiments. As shown in FIG. 6A, the user interface provides one or more social activity pages 602 and 604 that enable the users to submit their weekly social activity. Specifically, the social activity pages 602, 604 provide sliders that enable users to submit their weekly hours of one or more of: attending religious services; socializing with friends; playing sports; volunteering; spent on social media; purposeful life time; cultural time; family time; and/or other social activity time of the user's choice (e.g., book, activity, or hobby clubs). In some embodiments, purposeful life time is defined as time spent on activity(ies) that a person is committed to that is beyond their personal interest; social media time is defined as time spent using a social media application, program or device; and/or cultural time is defined as time spent attending cultural events (e.g. museums, theater or other similar events). In some embodiments, the interface further provides one or more "other" sliders that, when selected, opens a text box where the user is able to submit text describing a type of social time, confirm their submitted text, and then move the slider to specify the number of hours spent doing the specified activity during the week. Further, in some embodiments each of the sliders are able to include an associated button (e.g. question mark) that when selected defines the type of social activity to which the slider relates.

Figure 6B:
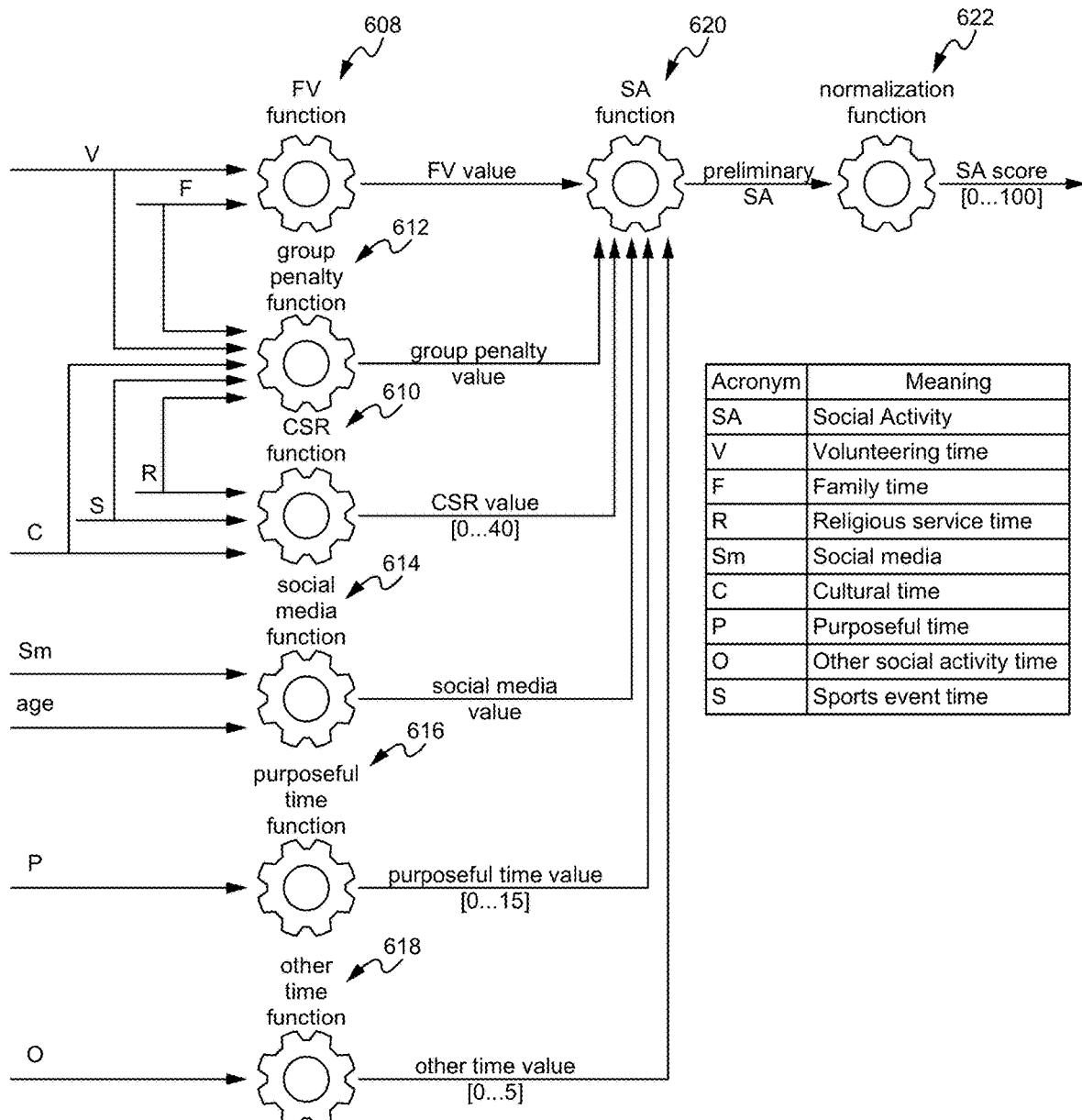
FIG. 6B illustrates a flow diagram showing an input, scoring and recommendation process of the social activity module according to some embodiments.

FIG. 6B illustrates a flow diagram showing an input, scoring and recommendation process of the social activity module according to some embodiments. As shown in FIG. 6B, after inputting a user's weekly social activity via the input page(s) 602, 604, a family/volunteering function 608 of the module determines family/volunteering (FV) value that is equal to [3*(volunteering time+family time)], wherein if the FV value is greater than 40, the FV function sets the FV value to 40 and if either the volunteering time or the family time is 0, the FV function subtracts a penalty of 5 from the FV value. For example, if volunteering time was 0 and family time was 15 hours, the FV function would determine that 3*(0+15)=45, which it would set to 40 and then subtract 5 (because volunteering time=0) outputting a final FV value of 35 (i.e. 40-5). Alternatively, the penalty is able to be subtracted before the function 608 determines if the FV value is greater than 40 (and if so, sets it to 40).

Similarly, a cultural, religious and sports (CRS) function 610 determines a CRS value that is equal to 3*(religious service time+sport event time+cultural time). Subsequently, a group penalty function 612 sets a group penalty value equal to 10 if: both family time and volunteering time are 0; or the CRS value is 0. A social media function 614 determines a social media value equal to: (social media time−a predetermined number of healthy hours of social media week for a person of that age)*2.5. For example, the social media value is able to be equal to: (social media time−3.5 hours)*2.5 if the user is less than 65 years old; or (social media time−7)*2.5 if the user is 65 years old or older. Alternatively, other values for the predetermined number of healthy hours of social media week for a person of that age are able to be used. A purposeful time function 616 determines a purposeful time value equal to (3*purposeful time), wherein if the determined purposeful time value is greater than 15, the function sets the value to 15. Additionally, another time function 618 determines an other time value equal to 5 if the other time >0.

Finally, a social activity function 620 determines a preliminary SA score equal to [(FV value+CSR value+purposeful time value+other time value)−(group penalty value+social media value)]. If the preliminary SA score is negative, the normalization function 622 sets the preliminary SA score to 0 and outputs a SA score of 0. Otherwise, the normalization function 622 outputs an SA score equal to the (positive) preliminary SA score. As described above, this SA score is able to be presented to the user in order to enable them to quantify their social activity and determine if more or less social activity is advisable. Additionally, as described above, the platform 99 is able to identify ranges of SA scores to be associated with one or more conditions, such that having an SA score in the range indicates the associated condition. For example an SA score in a low range (e.g. 0-30) would indicate an associated condition of extreme introvert or potentially social phobia (e.g. agoraphobia) that is able to be used by the recommendation module as a condition of the user based on their SA score.

Nutrition Module

Figure 7A:
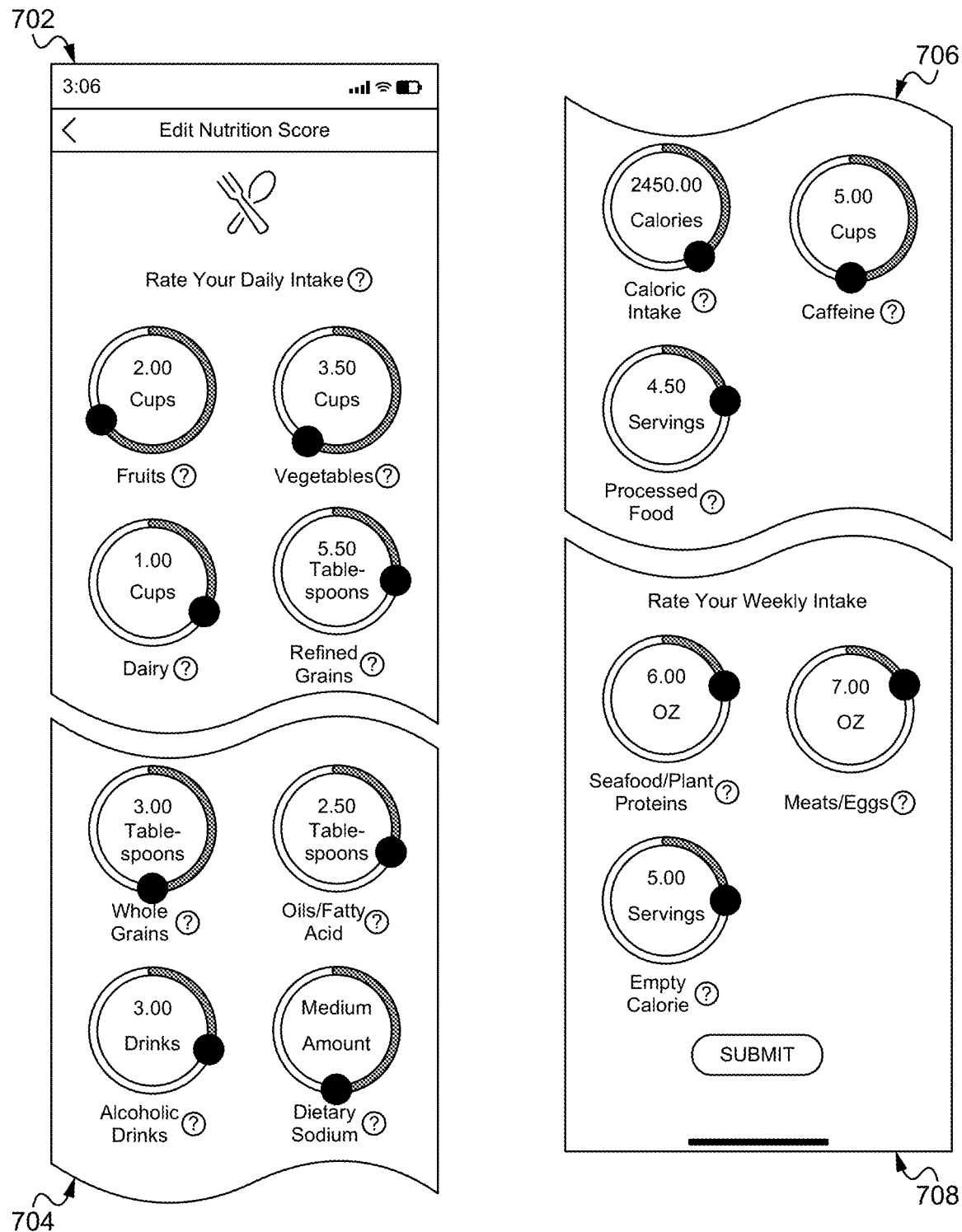
FIG. 7A illustrates a screenshot of a user interface of the nutrition module enabling nutrition data entry according to some embodiments.

The nutrition module provides a user interface that prompts users with and enables the users to submit responses to nutrition questions such that users are to submit their nutrition data to the platform 99 (see FIG. 7A). The nutrition module is then able to determine and present to the user a food score value for the user based on the submitted responses and the user's characteristic data (e.g. calorie needs as determined by the personal characteristics module). This nutrition data and/or score is then able to be added to the user profile of the user and/or be dynamically updated by the module based on newly submitted data by the user and/or data measured/input from one or more coupled devices (e.g. smart phone, smart watches). As a result, the nutrition module provides the benefit of helping users improve their eating habits and nutrition levels by using the right nutritional behavior for each food category depending on their life stage.

FIG. 7A illustrates a screenshot of a user interface of the nutrition module enabling nutrition data entry according to some embodiments. As shown in FIG. 7A, the user interface provides one or more nutrition pages 702-708 that enable the users to submit their daily food intake. Specifically, the nutrition pages 702-706 provide sliders that enable users to submit their daily intake quantities of one or more of: fruits, vegetables, dairy, refined grains, whole grains, oils/fatty acids, alcoholic drinks, dietary sodium, total caloric intake, caffeine and/or processed food intake. Similarly, the nutrition page 708 provides sliders that enable users to submit their weekly intake quantities of one or more of: seafood/plant proteins, meats/eggs, and/or empty calories (e.g. desserts/sweets). In some embodiments each of the sliders are able to include an associated button (e.g. question mark) that when selected defines the type of nutritional intake to which the slider relates. In some embodiments, sodium intake is categorized (and/or input) as high, medium or low. For example, for users with European ancestry, medium is able to be 2300 mg/day+/−20% daily value (e.g. 1840 to 2760 mg/day) with low range less the 20% of DV (e.g. less than 1840 mg/day) and high range above 20% above DV (e.g. greater than 2760 mg/day); and for users with African ancestries (African-American or African Caribbean from central Africa), medium is able to be 1500 mg/day+/−20% daily value (e.g. 1200 to 1800 mg/day) with low range less the 20% of DV (e.g. less than 1200 mg/day) and high range above 20% above DV (e.g. greater than 1500 mg/day). Alternatively, other ranges are able to be used for all users or an ancestry-based subset of the users.

Figure 7B:
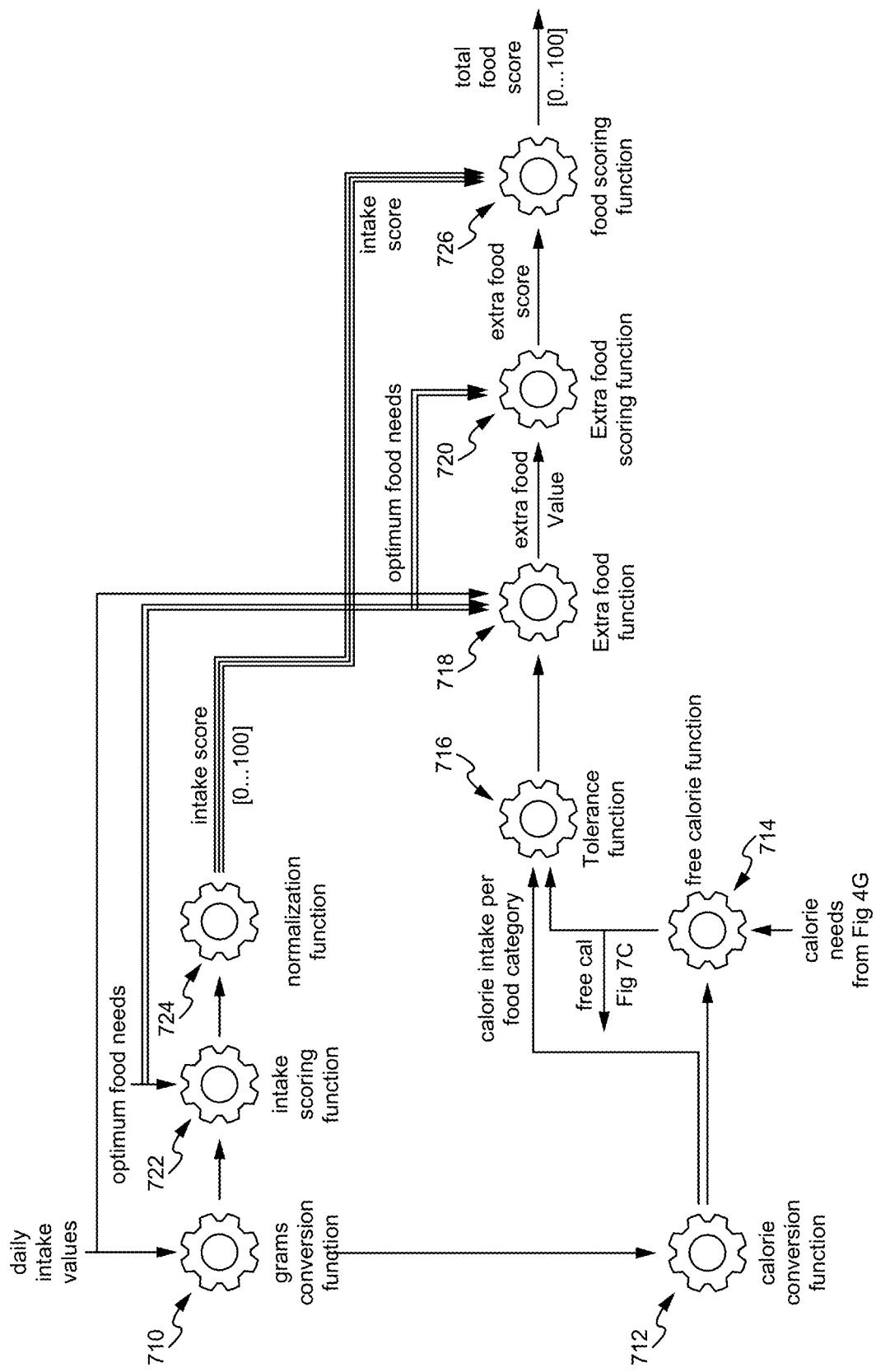
FIG. 7B illustrates a flow diagram showing an input, scoring and recommendation process of the nutrition module according to some embodiments.

FIG. 7B illustrates a flow diagram showing an input, scoring and recommendation process of the nutrition module according to some embodiments. As shown in FIG. 7B, after inputting a user's weekly/daily nutritional intake via the input page(s) 702-708, a gram conversion function 710 converts each of the intake quantity units of each food category or type (e.g. one or more of vegetable, fruit, dairy, whole grain, refined grain, seafood/plant protein, meat/egg, oil) to grams. Additionally, the conversion function 710 is able to convert to grams one or more of the other intake values such as alcohol, empty calories, sodium, processed food or other intake values for their use in subsequent functions. Alternatively, one or more of the intake values are able to remain unconverted. In some embodiments, the gram conversion function 710 uses different conversion factors depending on the food, wherein the conversion factors for each food category are computed by averaging the grams corresponding to the unit under conversion of at least 50 different foods representative of the category. Indeed, this use of food type specific conversions enables the nutrition module to make more accurate calorie intake calculations and recommendations than when using generic conversion rates. For example, each of the units are able to be converted to grams according to Table 1 below:

TABLE 1

Food Measures to Grams

| To Grams | grams |
| --- | --- |
| vegetable cup | 116.0 |
| fruit cup | 175.0 |
| dairy cup | 232.0 |
| whole/refined grain cup | 170.0 |
| seafood cup | 170.0 |
| meat cup | 225.0 |
| alcohol drink | 14.0 |
| oil tablespoon | 13.63 |
| empty calorie single serving size | 88.53 |

In other words, for example, each cup of seafood eaten a week by a user is converted to 170.0 grams of seafood eaten by the user.

After the quantities of each food category have been converted to grams by the conversion function, a calorie conversion function 712 of the nutrition module converts the grams of each food type input by the user to a total number of calories for each food type consumed by the user.

Specifically, using the values in Table 2 below, the calorie conversion function is able to determine the number of calories for each food type by multiplying the number of grams for that food type by the average calories per gram as indicated in Table 2. Both the data of Table 1 and Table 2 are able to be stored on the platform 99 and dynamically updated as needed.

TABLE 2

Average Calorie Content of Food Groups

| Food or Food Component | Avg. Calories/Gram |
|---|---|
| vegetables | 0.63 |
| fruits | 0.86 |
| dairy (milk, yogurt, low fat cheese) | 2.16 |
| meat/egg | 2.1 |
| seafood/plant | 2.73 |
| whole grain | 2.8 |
| refined grain | 2.8 |
| oils | 6.23 |
| alcohol | 7.0 |
| empty calories | 3.41 |

As a result, as shown in FIG. 7B, the calorie conversion function 712 is able to output a total number of calories for each food type for the user to the free calories function 714 and the tolerance function 716 of the nutrition module.

The free calories function 714 is able to determine a quantity of remaining calories (e.g. free calories) that the user can intake while remaining in the range of his or her optimal caloric needs. In some embodiments, this quantity is able to be determined by summing together the total calories of each food type (as received from the calorie conversion function) to determine a total calorie intake value, inputting the recommended calorie needs value (as determined by the personal characteristics module in reference to FIG. 4G), and subtracting the total calorie intake value from the calorie needs value to determine the quantity of remaining calories (with any negative numbers adjusted to 0). This remaining calories quantity is able to be transmitted to the tolerance function 716 and the nutrition scoring function 738 (see FIG. 7C).

The tolerance function 716 is able to determine how many of the remaining calories should be allocated to each of the food types for the user. These quantities are able to be the tolerance values of each of the food types. In other words, the tolerance function 716 is able to determine how many more grams of each of the food types (above what they are currently intaking) that a user is able to consume while still being within their optimal caloric needs. In particular, the tolerance function 716 is able to receive the remaining calories quantity and the current intake amount in grams of each food type, and assign the remaining calories (if any) to one or more of the food types based on a default or user input set of food type distribution percentages. This quantity of assigned calories (as converted to grams) is the tolerance value for that food type.

For example, if the remaining calories value is 1000 calories, the tolerance function 716 is able to use distribution percentages of 25% to vegetables, 20% to fruit, 20% to dairy, 10% to whole grains, 0% to refined grains, 0% to meat/eggs, 10% to seafood, and 5% to oil, and thus distribute 250 calories to vegetables, 200 to fruit, 200 to dairy, 100 to whole grains, 0 to refined grains, 0 to meat/eggs, 100 to seafood, and 50 to oil (wherein the assigned quantity of calories is able to be converted to grams for that food type using Table 2). In some embodiments, the default distribution percentages are able to be based on the caloric needs of the user for each food type (e.g. food type caloric needs of user/total caloric needs of user=distribution percentage for that food type for user). In some embodiments, the user is able to adjust the default percentages. These tolerance values are each associated with their respective food type (and the user) and form a tolerance value list. In some embodiments, the tolerance function 716 excludes the meat/eggs and/or refined grain food types from the allocation process such that the meat/eggs and/or refined grain food types are not allocated any of the remaining calories.

Subsequently, an extra food function 718 receives the tolerance values for the user for each of the food types and, for each food type, determines an extra food value equaling the amount of food that the user is currently consuming above an optimal amount (plus the tolerance value). For example, if a user has an intake of 12 grams of seafood/plant proteins, a tolerance value of 2 grams for seafood/plant proteins and the optimum intake amount is 8 grams of seafood/plant proteins, the extra food value would be intake−(optimum+tolerance), which is 12−(8+2)=2 grams. The optimum intake amount is able to be a predetermined value for each food type. For example, the optimum intake amount for each food type is able to be based on the USDA dietary guidelines for the user's sex, BMI and/or age.

These extra food values are then adjusted by an extra food scoring function 720 that adjusts the extra food value for each food type to determine an extra food penalty score for each food type. Specifically, for each food type, if the extra food value is greater than 0 the extra food scoring function 720 is able to determine an extra food penalty score equal to: [food penalty factor*extra food value for food type A/(optimum intake value for food type A)]. Otherwise, if the extra food value is equal to or less than 0, the extra food penalty score is set to 0. In some embodiments, the food penalty factor is −100. Alternatively, larger or smaller food penalty factor values are able to be used. For example, if the penalty factor is set to −100 and the optimal intake is 50 grams, then an extra food of food type A consumed by the user equal to 50 grams would result in an extra food penalty score of −100 (i.e. −100*(50/50)). Similarly, if the penalty factor is set to −100 and the optimal intake is 50 grams, then an extra food of food type A consumed by the user equal to 10 grams would result in an extra food penalty score of −20 (i.e. −100*(10/50)). Thus, the nutrition module is able to adjust the penalty size for overeating one or more of the food types.

In addition to the remaining calories value and the extra food score, the nutrition module is able to further determine an intake score used for calculating the total food score for each food type. To do this, an intake score function 722 determines the intake score for each food type based on the optimum intake amount for that food type (as described above in reference to the extra food function 718) and the daily intake of that food type by the user. For example, in some embodiments the intake score for a food type is equal to [100.0*(daily intake of the food type in grams)/optimum intake for that food type in grams], wherein if the optimum intake value is zero the intake score is set to 0. In some embodiments, the nutritional module further comprises a normalization function 724 that normalizes the intake scores for each of the food types by setting any intake scores greater than 100 to 100, and setting any scores less than 0 to 0.

These intake scores (for each food type) are then input by the food scoring function 726 along with the extra food penalty scores determined by the extra food scoring function 720. As a result, the food scoring function 726 is able to determine a total food score for each user for each of the food types based on the extra food penalty scores and the intake scores. For example, for each food type, the food scoring function 726 is able to determine the total food score for that food type as the sum of the extra food penalty score (e.g. −20) and the intake score (with any negative total food scores being set to 0 and any total food scores exceeding 100 being set to 100).

Figure 7C:
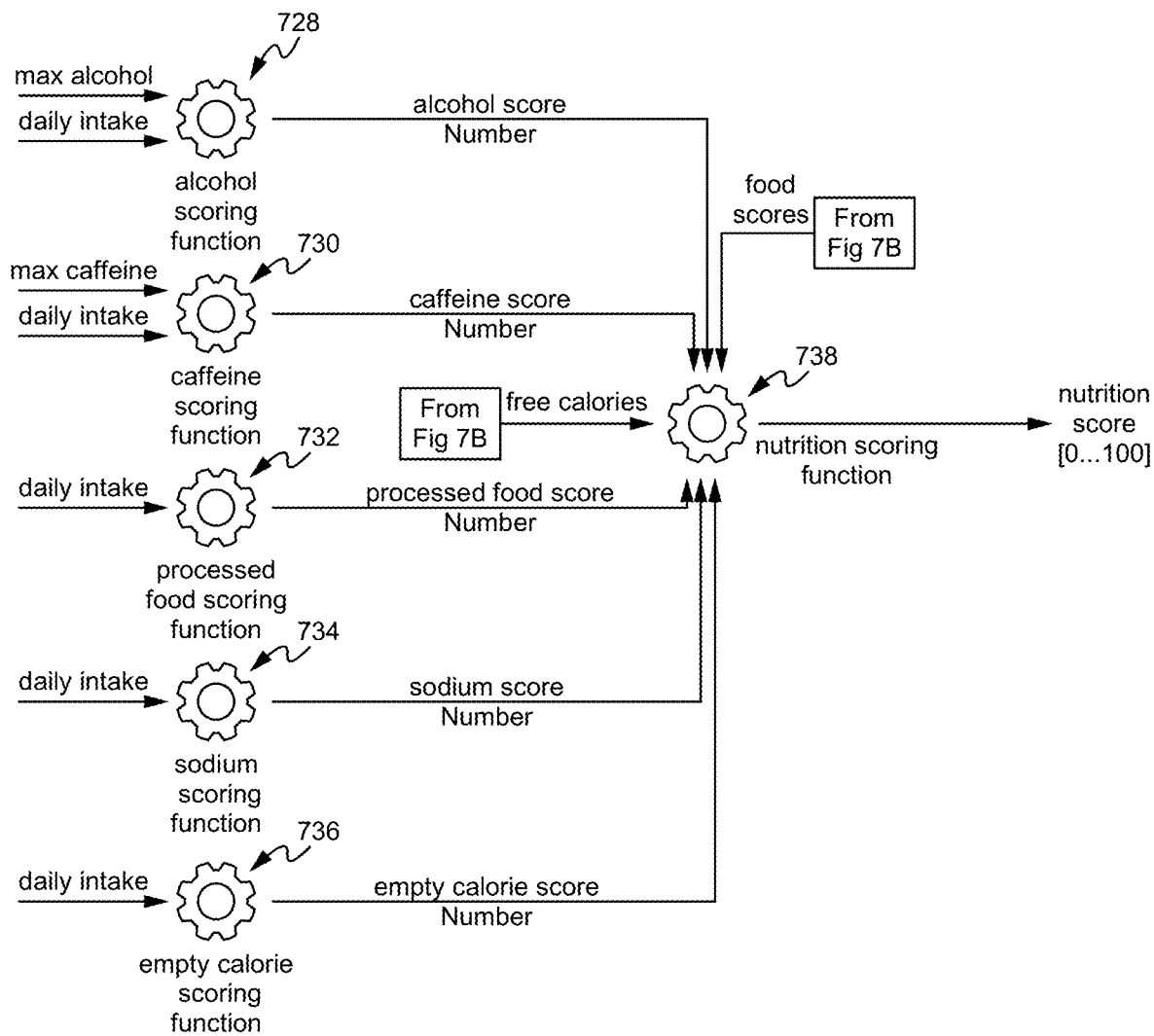
FIG. 7C illustrates another flow diagram showing an input, scoring and recommendation process of the nutrition module according to some embodiments.

Now turning to FIG. 7C, the nutrition module is able to incorporate the total food scores with an alcohol score, a caffeine score, the remaining calories value, a processed food score, a sodium score and an empty calorie score in order to provide a nutrition score to the user that they are able to use to gauge their current level of nutrition. The alcohol score is determined by the alcohol function 728 to be an alcohol penalty factor multiplied by the number of daily drinks exceeding the maximum daily alcohol value for the user (determined by the characteristics module with respect to FIG. 4G). For example, if the penalty factor is 5, the maximum daily alcohol value is 2 drinks and the daily intake is 3 drinks, the alcohol score will be 5 (i.e. 5*(3−2)). Similarly, the caffeine score is determined by the caffeine function 730 to be a caffeine penalty factor multiplied by the number of daily drinks exceeding the maximum daily caffeine value for the user (determined by the characteristics module with respect to FIG. 4G). For example, if the penalty factor is 3, the maximum daily caffeine value is 2 drinks and the daily intake is 3 drinks, the caffeine score will be 3 (i.e. 3*(3−2)).

The processed food score is determined by the processed food function 732 to be a processed food penalty factor multiplied by the number of daily processed food servings (e.g. fast food) rounded up. For example, if the penalty factor is 2.5 and the daily servings of processed food is 1, the processed food score will be 3 (e.g. (2.5*1) rounded up). The sodium score is determined by the sodium function 734 to be a penalty of a predetermined value if the intake sodium value is within a high range and a bonus of a predetermined value if the intake sodium value is within a low range. For example, the penalty value is able to be equal to 5 (which would be deducted from the nutrition score as described below) and/or the bonus value is able to be equal to 5 (which would be added to the nutrition score as described below). Alternatively, higher or lower bonus and/or penalty values are able to be used.

The empty calorie score is determined by the empty calorie function 736 to be an empty calorie penalty factor multiplied by the intake number of weekly empty calorie servings exceeding a predetermined maximum weekly empty calorie servings value for the user. For example, if the penalty factor is 5, the maximum weekly empty calorie servings value is 3 servings and the weekly intake is 5 servings, the empty calorie score will be 10 (i.e. 5*(5−3)). Additionally, in some embodiments the empty calorie function 736 dynamically adjusts the predetermined maximum weekly empty calorie servings value for the user to 0 if their total calorie intake value exceeds their recommended caloric needs value (as determined by the personal characteristics module in reference to FIG. 4G). For example, the empty calorie function 736 is able to determine this in the same manner as the free calorie function 714 determines if there are any free calories by comparing the intake value to the recommended value. As a result, if the intake does exceed the recommended and the empty calorie function 736 sets the predetermined maximum weekly empty calorie servings value for the user to 0, any weekly empty calorie servings will be penalized. Using the same values as the example above, if the penalty factor is 5, the maximum weekly empty calorie servings value is 0 servings and the weekly intake is 5 servings, the empty calorie score will be 25 (i.e. 5*(5−0)).

Finally, the nutrition scoring function 738 is able to input the total food score for each of the food types (as determined by the food scoring function 726) along with the alcohol score, the caffeine score, the processed food score, the sodium score, the empty calorie score and the free calories (determined by the free calorie function 714) in order to determine an overall nutrition score for the user. Specifically, the nutrition scoring function 738 is able to determine a main food average equal to: (vegetable total food score+fruit total food score+dairy total food score+grain total food score+protein total food score)/5, wherein the grain total food score is the average of the refined grain and whole grain total food scores and the protein total food score is the average of the meat/eggs and seafood total food scores. Then the nutrition function 738 is able to determine the nutrition score as (rounded to the nearest integer): ((0.95*main food average)+(0.05*oil total food score))−(alcohol score+caffeine score+processed food score+empty calories score) ±sodium bonus/penalty score), wherein the sodium score is added if it is bonus for low sodium and subtracted if it is a penalty for high sodium. As a result, the nutrition module provides the benefit of considering individual food types and/or other user intake in determining a more accurate nutrition value for the user.

In some embodiments, the normalizing factors 0.95 and 0.05 are able to be increased or decreased in order to adjust the ratio between oil and the other main foods. Such adjustments are able to maintain that the sum of the normalizing factors adds up to 1 (e.g. 0.05+0.95; 0.10+0.90; or other such combinations). In some embodiments, if the nutrition score is a negative number, the function 738 converts it to 0 and if the nutrition score is greater than 100, the function 738 converts it to 100 such that the all the nutrition scores are between a desired range (e.g. 0-100). Additionally, as described above, the platform 99 is able to identify ranges of nutrition scores to be associated with one or more conditions, such that having a nutrition score in the range indicates the associated condition. For example a nutrition score in a low range (e.g. 0-20) would indicate an associated condition of poor nutrition/malnutrition that is able to be used by the recommendation module as a condition of the user based on their nutrition score.

In some embodiments, as described above, analysis of the user's genetic risk scores based on input genetic data (e.g. DNA sequence or genotyping data) are able to provide additional information on a user's response to dietary components (e.g., the relative proportions of calories from carbohydrate, fat, and protein, or specific dietary supplements or specific types of dietary fats such as polyunsaturated versus monounsaturated fats). These risk scores are able to be incorporated into the individual's overall characteristics and used for adjusting the scoring modules and therefore subsequent recommendations.

Sleep Module

Figures 8A, 8B:
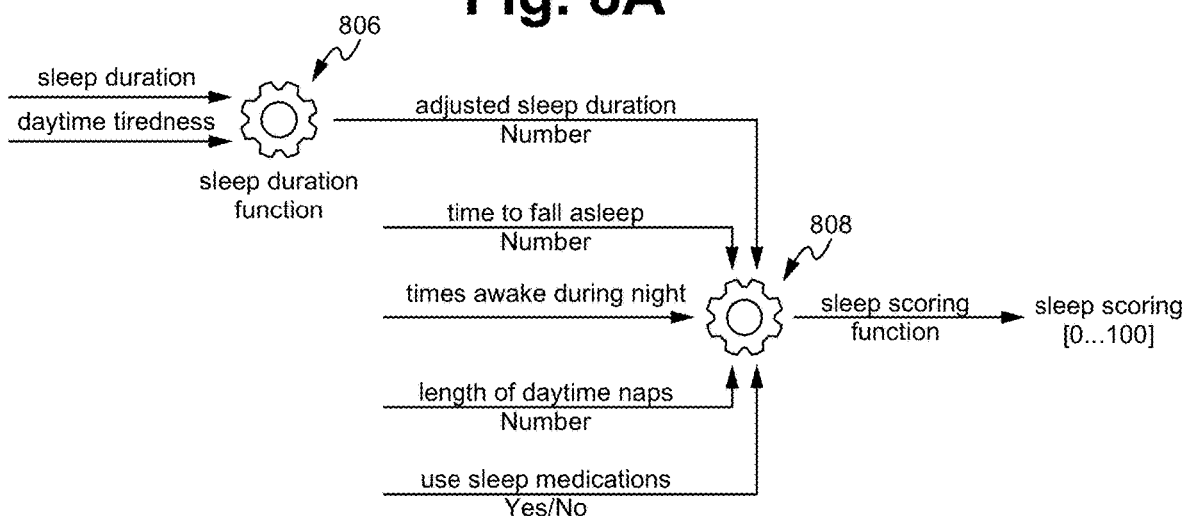
FIG. 8A illustrates a screenshot of a user interface of the sleep module enabling sleep data entry according to some embodiments.
FIG. 8B illustrates a flow diagram showing an input and scoring process of the sleep module according to some embodiments.

The sleep module provides a user interface that prompts users with and enables the users to submit responses to sleep questions such that users are to submit their sleep data to the platform 99 (see FIG. 8A). The sleep module is then able to determine and present to the user a sleep score value for the user based on the submitted responses. This sleep data and/or score is then able to be added to the user profile of the user and/or be dynamically updated by the module based on newly submitted data by the user and/or data measured/input from one or more coupled devices (e.g. smart phone, smart watches). As a result, the sleep module provides the benefit of helping users improve their sleep habits by providing a sleep score that considers multiple factors in determining their quality of sleep.

FIG. 8A illustrates a screenshot of a user interface of the sleep module enabling sleep data entry according to some embodiments. As shown in FIG. 8A, the user interface provides one or more sleep pages 802, 804 that enable the users to submit their sleep habits. Specifically, the sleep pages 802 and 804 provide sliders and other input elements that enable users to submit their average sleep duration, time to fall asleep, a self-rated assessment of tiredness during the day, a number of times one awakes each night, an amount of time for day naps, a yes or no question about using sleep medications, a time to bed and a time to get up. In some embodiments, the daytime tiredness is a self-rated score of how energetic a person feels during the daytime (e.g. rated as 0 for not tired, 1 a little tired, 2 for somewhat tired, 3 for tired, 4 for very tired, 5 for extremely tired). Indeed, this tiredness factor provides the benefit of enabling the sleep score to adjust to the personal sleep habits of the user, rather than relying on an objective amount of sleep recommended. In other words, even if an average user will need a certain amount of sleep, the sleep module is able to factor in whether a current user does not feel tired despite getting less than that amount or does feel tired despite getting that amount or more by inputting their daytime tiredness level. As a result, the sleep module provides the benefit of producing a sleep score that adjusts to the personal characteristics of the user.

In some embodiments each of the sliders are able to include an associated button (e.g. question mark) that when selected defines the type of sleep data to which the slider relates. In some embodiments, the time to bed and/or time to wake up are able to be omitted or are not used to calculate the sleep score, but rather to identify the user as having an early bird or night owl chronotype (which is able to be added to their personal characteristic data).

FIG. 8B illustrates a flow diagram showing an input and scoring process of the sleep module according to some embodiments. As shown in FIG. 8B, after inputting a user's sleep duration and daytime tiredness, a sleep duration function 806 generates an adjusted sleep duration number based on the input sleep duration and tiredness values. For example, the sleep duration function 806 is able to convert the sleep duration to a sleep duration score between a desired range (e.g. if sleep duration is less than 4 hours, the duration score is 2.5; if sleep duration is 4 to 6 hours, the duration score is 5; if sleep duration is 6 to 8 hours, the duration score is 10; and if sleep duration is greater than 8 hours, the duration score is 7.5). The sleep duration function 806 is then able to determine the adjusted sleep duration number using Table 3 below:

TABLE 3

| Daytime Tiredness Value | Adjusted Sleep Duration Number= |
|---|---|
| If = 0 or 1 | duration score × 2; maximum of 10 |
| If = 2 or 3 | duration score |
| If = 4 or 5 | duration score ÷ 2 |

Subsequently, a sleep score function 808 is able to receive the determined sleep duration number and determine a sleep score based on the sleep duration number, the time to fall asleep value, the times awake during the night value, the length of daytime naps value and/or the use or non-use of sleep medications. In particular, the sleep score function 808 is able to convert the time to fall asleep (in minutes), the nap time (in minutes) and/or the times awake at night to adjusted scores each within desired ranges (e.g. 1-5). For example, if time to fall asleep is less than 15 minutes, 16 to 30 minutes, 31-45 minutes, 46-60 minutes or greater than 60 minutes, the adjusted fall asleep score is 5, 4, 3, 2 or 1, respectively. Similarly, if the nap time is 0-14 minutes, 15 to 30 minutes, 31 to 45 minutes, 46 to 60 minutes or greater than 60 minutes, the adjusted nap score is 5, 4, 3, 2 or 1, respectively. Additionally, if the number of times awakened during the night is 0, 1, 2, 3 or greater than 3, the adjusted times awakened score is 5, 4, 3, 2, or 1, respectively. Alternatively, other ranges and/or mappings are able to be used. Finally, the sleep score function 808 is able to determine a sleep score for the user equal to: [adjusted sleep duration number* (adjusted time to fall asleep score+adjusted nap score+ adjusted times awakened score)−(10 if the user indicated that sleep medications are used)]*normalization value (e.g. 0.667 to yield a sleep score of 0 to 100). Additionally, as described above, the platform 99 is able to identify ranges of sleep scores to be associated with one or more conditions, such that having a sleep score in the range indicates the associated condition. For example a sleep score in a low range (e.g. 0-25) would indicate an associated condition of poor sleep/insomnia that is able to be used by the recommendation module as a condition of the user based on their sleep score.

In some embodiments, as described above, analysis of the user's genetic risk scores based on input genetic data (e.g. DNA sequence or genotyping data) are able to provide additional information on a user's circadian rhythm and therefore sleep habits (e.g., genetic contribution of timing of sleep such as time to bed, length of time sleeping, sleep needs). These risk scores are able to be incorporated into the individual's overall characteristics and used for adjusting the scoring modules and therefore subsequent recommendations.

Thus, the sleep module provides the benefit of producing a sleep score on an easy to understand scale and/or that incorporates how tired the user feels during the day with their current sleep habits.

Lifestyle Module

The lifestyle module determines and presents to the user a lifestyle score value for the user based on one or more of the physical activity score, the social activity score, the nutrition score and/or the sleep score. This lifestyle score is then able to be added to the user profile of the user and/or be dynamically updated by the module based on newly submitted data by the user and/or data measured/input from one or more coupled devices (e.g. smart phone, smart watches). As a result, the lifestyle module provides the benefit of helping users determine an overall ranking of their current lifestyle including each of the various factors of their life. In other words, the module provides the benefit of instead of merely focusing on individual aspects of the user's life, it provides a holistic view of the lifestyle by integrating diet habits, sleep, physical activity and/or social participation.

Figure 9:
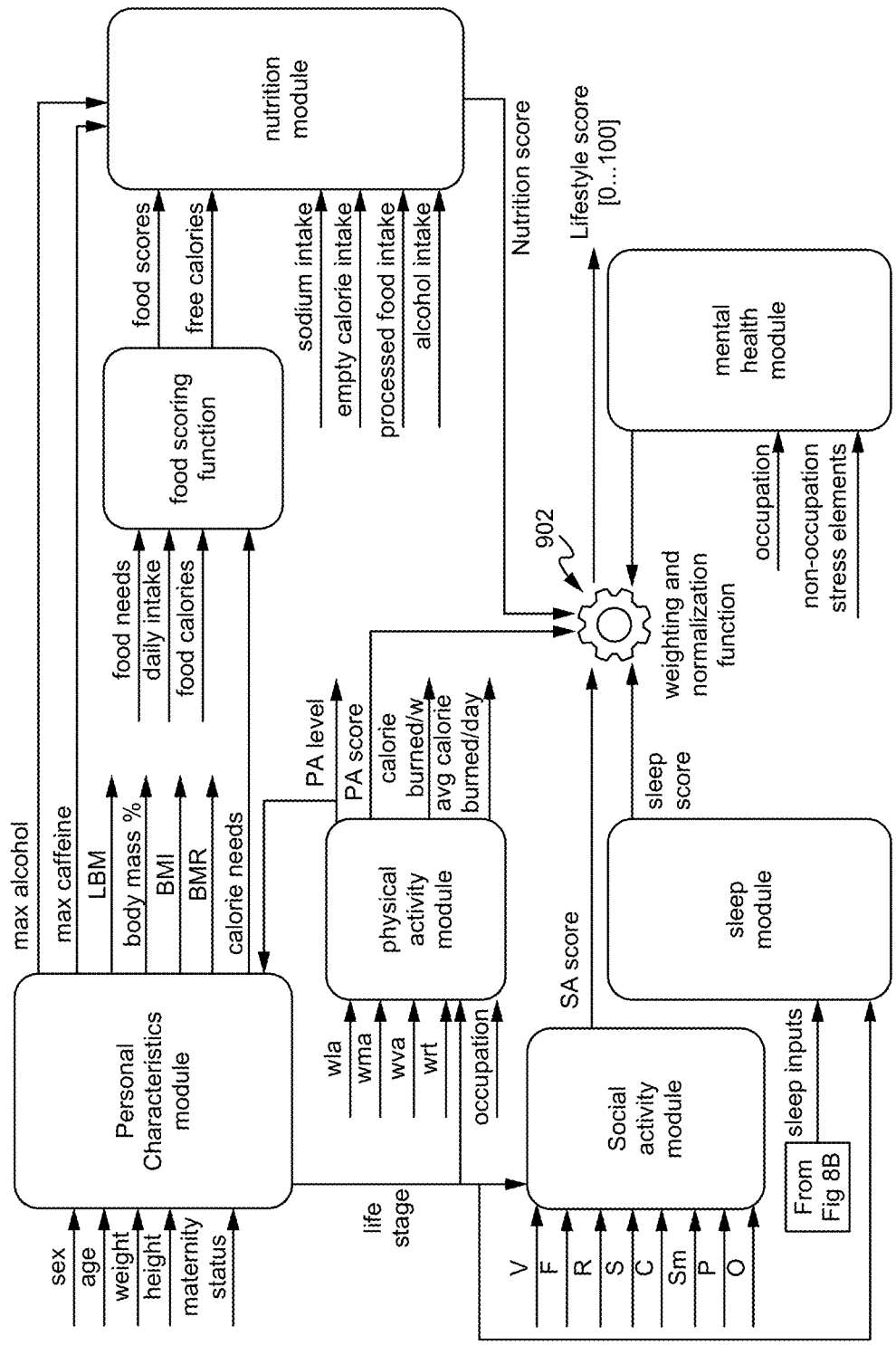
FIG. 9 illustrates a flow diagram showing an input and scoring process of the lifestyle module according to some embodiments.

FIG. 9 illustrates a flow diagram showing an input and scoring process of the lifestyle module according to some embodiments. As shown in FIG. 9, after inputting each of the sleep score, physical activity score, social activity score and/or nutrition score, the lifestyle module utilizes a lifestyle function 902 to combine the scores (e.g. including weighting and normalizing) in order to produce an overall lifestyle score. For example, the lifestyle function 902 is able to apply a weight to each of the scores and then sum the scores to produce the lifestyle score. In some embodiments, the weights are able to be percentages that together add up to 100% such that the sum of each of the scores (which were already normalized to be between 0 and 100) will be a number between 0 and 100. In such embodiments, the nutrition score is able to be weighted by 30%, the physical activity score is able to be weighted by 30%, the social activity score is able to be weighted by 20%, the stress score is able to be weighted by 10% and the sleep score is able to be weighted by 10%. Thus, if a user had nutrition, physical activity, social activity, stress and sleep scores of 80, 70, 40, 50 and 60, respectively, their lifestyle score would be 64 (i.e. 65=(80*0.30)+(70*0.30)+(40*0.20)+(50*0.1)+(60*0.1)). Alternatively, different weights are able to be used for one or more of the scores and/or one or more of the scores are able to be omitted (with the sum of the weights being equal or not equal to 100%).

Pathogen Risk Module

The pathogen risk module maintains access to and/or operates a pathogen database or knowledge base (e.g. a part of the knowledge base 106) that associates the incidence of infections (e.g. infection rate) for a plurality of pathogen types (and/or subtypes) with one or more pathogen parameters such as: the total population, one or more age groups, ethnicities, sex, occupation, locations (e.g. county, zip code or other defined area), other user profile characteristics (such as those input by the users described herein) and/or a combination thereof. For example, the pathogen database is able to indicate the incidence rate for COVID-19 (or other infectious diseases such as seasonal influenza outbreaks) for males within county A, for ages 0-15, for healthcare workers, and all other permutations of the parameters as a plurality of tuples stored in the database. Using this database, for one or more of the pathogens (and/or subtypes thereof) the pathogen risk module is able to match the personal characteristics data of the user (e.g. sex, age, weight, height, maternity status, genetic ancestry/ethnicity, occupation, vaccination status, mask wearing behavior, social distancing behavior and/or zip code) with the parameters of that pathogen to determine the associated incidence of infection for the user (which is then able to be adjusted by the user's occupation). This pathogen risk is then able to be added to the user profile data, presented to the user via the platform 99 graphical user interface and/or be dynamically updated by the module based on newly submitted data by the user and/or data measured/input from one or more coupled devices (e.g. smart phone, smart watches). As a result, the pathogen module provides the benefit of helping users reduce their risk of infection from pathogens by evaluating their current risk level. Again, in some embodiments the pathogen database is able to be a part of the knowledge base 106 and/or personal health servers 102. Alternatively, the pathogen database is able to be separate from the knowledge base and/or a part of a $3^{rd}$ party network accessible database.

Figure 11B:
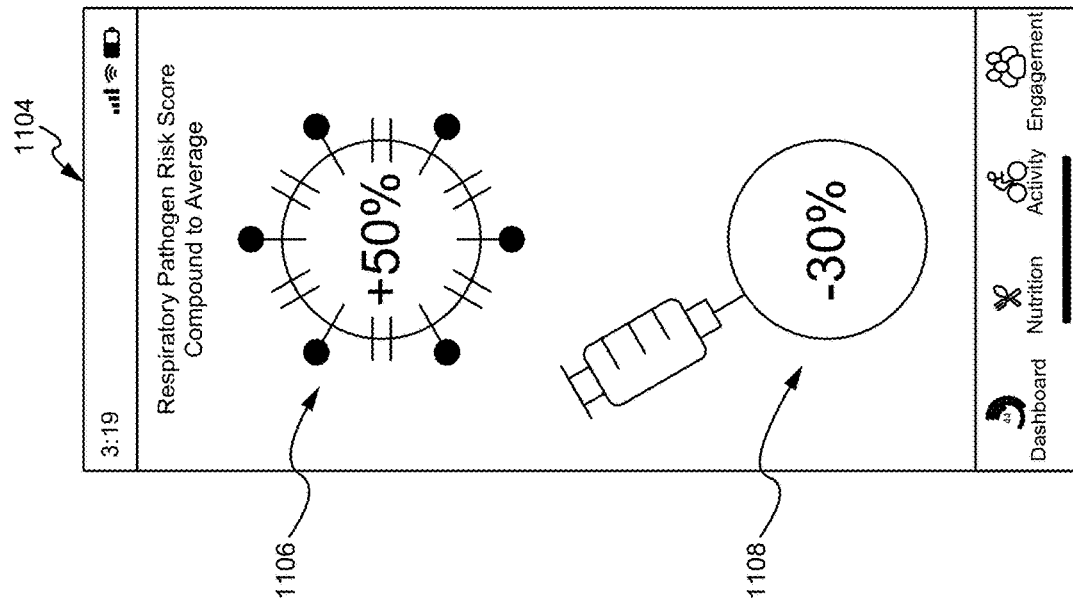
FIG. 11B illustrates a screenshot of a user interface of the pathogen risk module enabling the presentation of the pathogen risk score according to some embodiments.
Figure 11A:
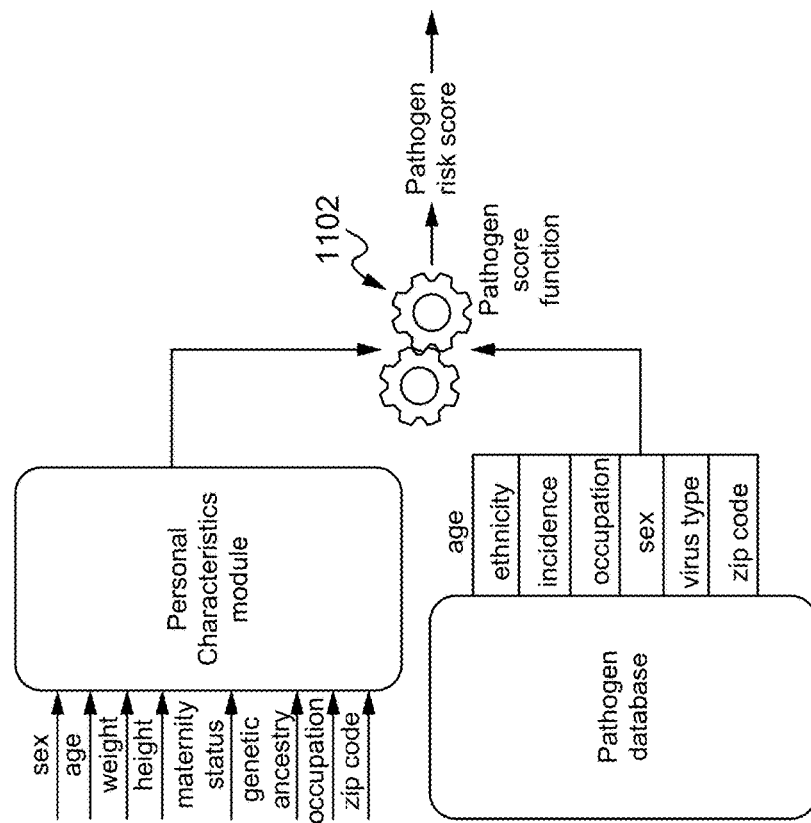
FIG. 11A illustrates a flow diagram showing an input and scoring process of the pathogen module according to some embodiments.

FIG. 11A illustrates a flow diagram showing an input and scoring process of the pathogen module according to some embodiments. As shown in FIG. 11A, after accessing a user's personal characteristics from their stored user profile and the incidence of infections and associated data from the pathogen database, a pathogen score function 1102 generates a pathogen risk score. The score is able to indicate a difference between the average population attributable risk of infection by the pathogen and the individual's risk of infection based on the individual's profile characteristic data. In some embodiments, both values are adjusted for occupation risk (e.g. with the average risk for 873 populations=60.5). For example, the pathogen risk score is able to be determined as follows:

$$\text{Pathogen risk score} = (PAR_i * \text{average occupational risk}) - ((xA + yA) * OPPS_A);$$

Where $PAR_i$=population risk of infection by the selected pathogen (or sub-pathogen) as indicated by the pathogen database (e.g. across all individuals in the database); the average occupational risk=60.5 (e.g. as indicated by the occupation physical proximity table described below); xA=the sum of incidences for age+sex+ethnicity+pathogen type+zip code matching individual A as indicated in pathogen database; yA=the sum of incidences of all pathogen subtypes in location matching individual A; and $OPPS_A$= Occupation physical proximity score for the occupation of individual A as indicated by an occupation physical proximity table. Thus, the module is able to improve on existing systems by determining not only a user's individual risk to a pathogen, but also their risk compared to the average risk of the population. Indeed, this comparison type value is beneficial because it allows users to identify if they are particularly more or less at risk than the general population and adjust their behavior accordingly.

The occupation physical proximity table is able to indicate a ranking score for each of a plurality of occupations indicating how much the occupation needs to interact closely with other people and thus its relative risk of pathogen infection with respect to other occupations. Like the pathogen database, the occupation physical proximity table is able to be a part of the knowledge base 106 and/or personal health servers 102. Alternatively, it is able to be separate from the knowledge base and/or a part of a $3^{rd}$ party network accessible database such as O-Net Online (https://www.onetonline.org/).

The determined pathogen risk score is able to be dynamically updated by the pathogen module (e.g. as the user changes location, occupation, age, and/or other characteristics) and displayed to the user by the pathogen risk module. Further, in some embodiments the pathogen risk module is able to determine an adjusted pathogen risk score by taking the determined pathogen risk score above and adjusting it based on the user's vaccination status (for the pathogen), mask wearing behavior/social distancing behavior (as input by the user) and/or other personal characteristics of the user. For example, the adjusted pathogen risk score is able to equal the pathogen risk score plus or minus a predetermined adjustment percentage based on the user's vaccination status (for the pathogen), mask wearing behavior/social distancing behavior (as input by the user) and/or other personal characteristics of the user. In some embodiments, the masking/social distancing reduction value is able to be equal to 25%. Alternatively, higher or lower values are able to be used. In some embodiments, the vaccination status reduction value is based on the efficacy of the specified vaccination for the pathogen (and/or the distribution of sub-pathogens thereof). In particular, vaccination reduces risk for a specific respiratory pathogen within the range of vaccine efficacy for the average reported value (usually between 60 and 75% but as high as 95% for certain vaccines) and 100%. However, since different pathogen subtypes (and mutations) may be occurring in a population, the vaccination status reduction value is able to be adjusted up or down from the efficacy value by an adjustment value to account for new pathogen subtypes and/or changes in the relative levels of each subtype within the location.

Finally, after determining each of the pathogen risk scores (and/or adjusted pathogen risk scores) for the user for each of the pathogens (e.g. described in the pathogen risk database and/or for which a score was determined), the pathogen risk module is able to determine an overall pathogen risk value. This overall pathogen risk value is able to indicate to the user their cumulative risk of infection from all the pathogens when taken together. In some embodiments, the module is able to determine the overall pathogen risk value to be equal to an average (or weighted average) of each of the pathogen risk values (and/or the adjusted pathogen risk values). Alternatively, other metrics for combining the multiple risk values are able to be used. In any case, this overall pathogen risk value would provide the improvement of enabling the user to not only adjust their behavior based on any single pathogen (based on that pathogen's pathogen risk value for the user), but rather to take a holistic view as to reduce their pathogen risk from all of the pathogens at once. In such embodiments, the user interface enables the user to see both the overall pathogen risk value as well as the pathogen risk values for one or more selected pathogens.

Additionally, as described above, the platform 99 is able to identify ranges of pathogen risk or adjusted risk scores to be associated with one or more conditions, such that having a pathogen risk or adjusted risk score in the range indicates the associated condition. For example a pathogen risk or adjusted risk score in a low range (e.g. 0-5) would indicate an associated condition of those vulnerable to infection that is able to be used by the recommendation module as a medical condition of the user for identifying recommendations (e.g. matching conditions of tuples) based on their pathogen risk and/or adjusted risk score. Alternatively, the vaccination status, mask wearing behavior/social distancing behavior and/or other personal characteristics are able to be a part of the pathogen database parameters such that the filtering of the tuples of the database is able to reflect those differences in the infection rates of the remaining tuples. In any case, this adjusted risk score is able to provide the benefit of illustrating to the user how much of a difference their vaccination status, behavior and/or other characteristics change their risk of infection.

FIG. 11B illustrates a screenshot of a user interface of the pathogen risk module enabling the presentation of the pathogen risk score according to some embodiments. As shown in FIG. 11B, the user interface provides a pathogen risk page 1104 that presents to the users with one or both of their pathogen risk score 1106 and their adjusted pathogen risk score 1108. Thus, the pathogen risk module is able to indicate to the user how much more or much less risk they currently have to a selected pathogen than an average person in their location. Accordingly, the pathogen risk module provides the benefit of providing a pathogen risk score that takes into consideration the user's personal traits as well as the occupation. This is particularly beneficial in providing protection to individuals who may want to be vaccinated (with a biological vaccine), but who cannot be vaccinated, for example because of unavailability of a vaccine, or inability to obtain a vaccine affordably or at all, but who are still susceptible to the particular disease in question. Specifically, people with underlying health conditions (comorbidities) that weaken their immune systems (such as, for example, diabetes, cancer or HIV) or who have severe allergies to some vaccine components may not be able to get vaccinated with certain biological vaccines. These people can still be protected by the module. In addition, because no single biological vaccine provides 100% protection, and even herd immunity does not provide full protection to those who cannot safely be vaccinated, the module provides the benefit of added assurances of protection both to individuals and to others in the community.

In some embodiments, as described above, analysis of the user's genetic risk scores based on input genetic data (e.g. DNA sequence or genotyping data) are able to provide additional information on a user's susceptibility to one or more pathogens (e.g., genetic variation in a virus receptor protein). These risk scores are able to be incorporated into the individual's overall characteristics and used for adjusting the scoring modules and therefore subsequent recommendations. In some embodiments, the pathogen risk score can be modified when a user takes a prescription or over-the-counter medication designed to block the in vivo life cycle of the pathogen (e.g., blocking entry of the pathogen into susceptible target tissues, interfering with replication of the pathogen, or reducing the negative physiological responses to the pathogen). Risk scores are able to be modified by the use of the drug or supplement.

Digital Vaccine Module

The digital vaccine module inputs one or more of the scores (e.g. nutrition score, physical activity score, social activity score, pathogen score, stress score, sleep score), some or all of the user characteristic data (e.g. location, masking/social distancing behavior, vaccination status), and event/business data, and determines one or more pathogen recommendations for the user. Specifically, based on a determined current location of the user (e.g. as indicated by the user device 106), the digital vaccine module is able to identify one or more nearby locations/entities (e.g. parks, shopping malls, businesses or other types of locations/entities) and events thereof and assign pathogen risk values (e.g. per pathogen and/or for a combination of one or more of the pathogens) to each of the locations/entities/events for presentation as pathogen recommendations to the user. Thus, the module is able to provide pathogen recommendations to the user showing the locations, entities and/or events having the lowest pathogen infection risks (e.g. as compared to other risks in the area or of that same entity/location/event type). As a result, the user is able to make an intelligent decision as to which, if any, of the entities/events/locations to visit based on the pathogen risk they pose.

In some embodiments, the pathogen risk assigned to each of the locations/entities/events is based on a locations/entities/events pathogen risk database that maintains a pathogen risk for various locations/entities/events based on past infections/infection rates in those locations, entities and/or events. In some embodiments, the user interface of the digital vaccine module provides a planning feature that enables a user to input their travel plans with intended locations, entities and/or events to visit and the module is able to determine and present the pathogen risk of those locations, entities and/or events (and/or the pathogen risk of other entities and/or events near the submitted location, entity and/or event). In some embodiments, the digital vaccine module is able to generate group-wide or personalized recommendations for avoiding deleterious contact with the pathogen or lessening the likelihood of the pathogen entering, or successfully establishing itself in, the host's body.

Figure 12:
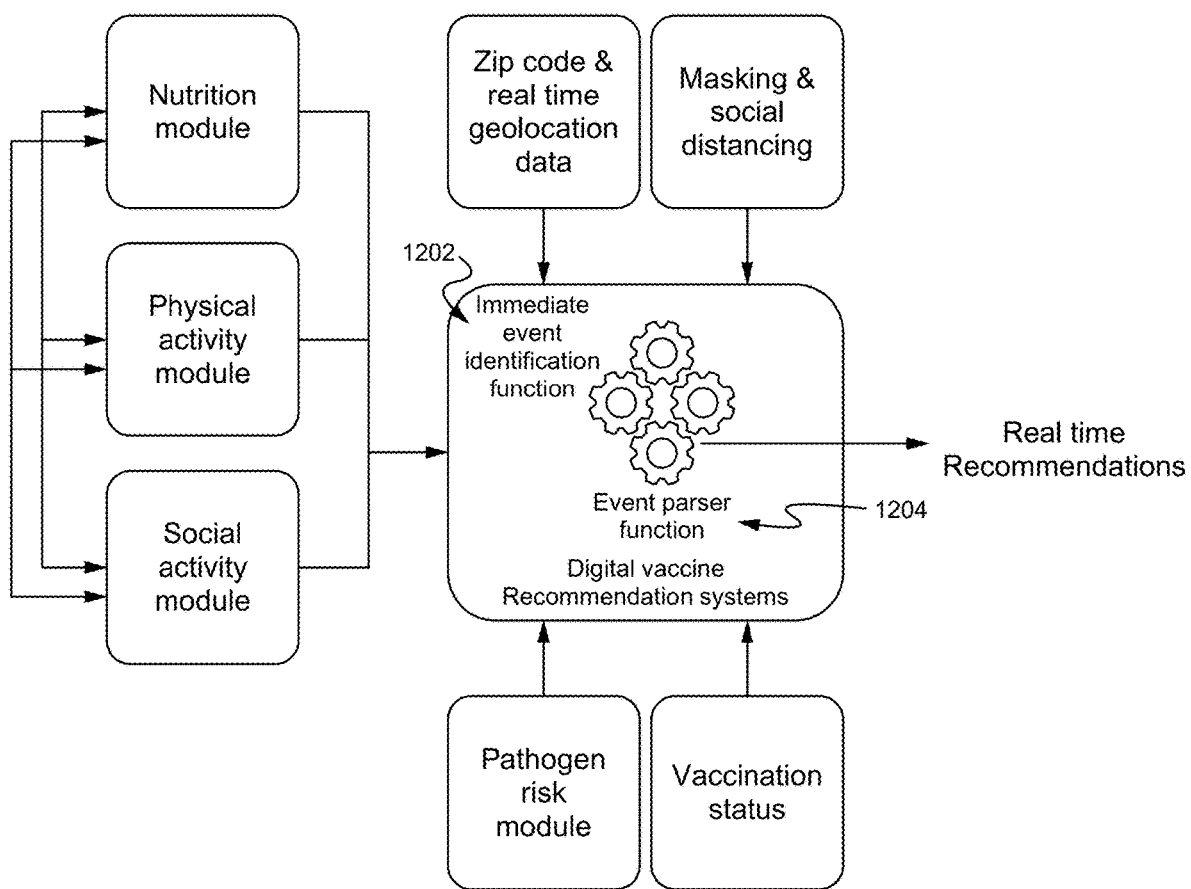
FIG. 12 illustrates a flow diagram of the digital vaccine module according to some embodiments.

FIG. 12 illustrates a flow diagram of the digital vaccine module according to some embodiments. As shown in FIG. 12, based on the location of the user as input from the user device 104 or manually input from the user directly, the module uses an immediate event function 1202 to determine one or more locations/entities/events near the location of the user (and/or near the location/entity/event input by the user as a future plan). An event parser function 1204 of the digital vaccine module then matches these nearby events/locations/entities with average event pathogen safety data and/or data of incidences and rates of infection of pathogens (e.g. flu, hepatitis, and coronavirus) from that location/entity/event to determine an actual event pathogen risk for each of the submitted and/or nearby locations/entities/events. In some embodiments, this actual event pathogen risk is able to be for all types of pathogens found in the event/location/entity pathogen database. Alternatively, the risk determined is able to be for one or more pathogens selected by the user via the user interface of the module. Within the database, the event/location/entity pathogen risk values are able to be associated with each type of pathogen as well as the type of location, type of entity, type of event, current time information (e.g. time of day, time of year, day of the week) and/or other characteristics of the locations/entities/events. In such embodiments, the event parser function 1204 is able to match the type of the event/location/entity as well as the time information in order to determine the pathogen risk value for each of the events/locations/entities as indicated in the database.

Based on this data, the vaccine module determines one or more pathogen recommendations for the user (e.g. in the form of risk values for one or more of the entities/locations/events and/or highlighting those having lower risks values) and presents them to the user. In some embodiments, the pathogen recommendations include suggestions to wear a mask, stay socially distant, limit time at location/event/entity to below time threshold value and/or get vaccinated for pathogen. For example, the module is able to suggest being socially distant for events/entities/locations having low pathogen risk values, suggest wearing a mask and staying socially distant for events/entities/locations having medium pathogen risk values and suggest limiting time and/or getting vaccinated along with masking/social distancing for events/entities/locations having high pathogen risk values.

In some embodiments, the module is able to proactively text the recommendations to the user device 104 in order to prompt them of their current pathogen risks and recommendations to lower said risks. In some embodiments, the location/zip code characteristic for the user is able to be dynamically updated (e.g. upon determination of the digital vaccine recommendations) based on the location of the user device 104 and/or prompting the user to update their current location to the platform 99. In addition, the local environment (including a location based pathogen risk thereof) of each user is able to be further determined by mapping his/her zip code to corresponding data in a location database (e.g. census data).

In some embodiments, the digital vaccine module includes a pathogen update function that is able to determine whether complying with the pathogen recommendations alters the user's pathogen risk score and/or update pathogen risk recommendations based on user feedback. For example, being infected with a pathogen might induce additional symptoms or conditions for individuals with pre-existing disease altering their pathogen risk score. This pathogen update feedback function is able to operate similarly to the update function of the recommendation module described below. In particular, the pathogen update function is able to periodically, randomly, or upon demand, query the user as to whether they have been compliant with one or more of the pathogen recommendations. If the user indicates that they have been compliant, the module is able to ask the user to update some or all of the profile data that they input using the other modules described herein. Then based on any changes to the profile data, the digital vaccine module is able to: adjust the pathogen recommendations and/or data upon which the pathogen recommendation was based; discontinue use of the pathogen recommendation; and/or create a new pathogen recommendation.

For example, if the pathogen recommendations with which the user was compliant did not result in a reduction of the pathogen risk to the user (as measured by the pathogen risk score and/or adjusted pathogen risk score), the digital vaccine module is able to delete, remove from consideration for this user, and/or lower the rank of that pathogen recommendation. Similarly, if the pathogen recommendations with which the user was compliant did result in a reduction of the pathogen risk to the user (as measured by the pathogen risk score and/or adjusted pathogen risk score), the digital vaccine module is able to increase the rank of that pathogen recommendation. Further, in some embodiments if the changes input by the user indicate one or more conditions/factors have an effect on the pathogen risk score, the digital vaccine module is able to generate a new pathogen recommendation that is able to be used in the future for future pathogen recommendations to the same user and/or other users. In some embodiments, the change input by the user is measured based on the changes to one or more of their scores, wherein increases in score indicate that the recommendation is working and decreases in score indicating that the recommendation may need to be updated, deleted and/or reevaluated. In some embodiments, the module only asks the user to update the profile data that was used to determine the recommendation. Alternatively, the module is able to ask the user to update all of their profile data.

In some embodiments, as described above, analysis of the user's genetic risk scores based on input genetic data (e.g. DNA sequence or genotyping data) are able to provide additional information on a user's susceptibility to one or more pathogens (e.g., genetic variation in a virus receptor protein). These risk scores are able to be incorporated into the individual's overall characteristics and used for adjusting the scoring modules and therefore subsequent recommendations. In some embodiments, the pathogen risk score can be modified when a user takes a prescription or over-the-counter medication designed to block the in vivo life cycle of the pathogen (e.g., blocking entry of the pathogen into susceptible target tissues, interfering with replication of the pathogen, or reducing the negative physiological responses to the pathogen). Risk scores are able to be modified by the use of the drug or supplement.

As a result, the digital vaccine module provides the advantage of not only to provide improved/personalized pathogen recommendations and updated pathogen scores for the user, but also to provide the opportunity to (i) test whether published knowledge is accurate for any or each individual, and (ii) identify new associations between the many factors that affect health and disease outcomes. Further, the module provides the advantage of discovering new correlations between these factors and resistance or susceptibility to pathogens. These new associations will provide enhanced ability to target more accurate pathogen recommendations to individuals to improve health, delay or ameliorate disease, and actions to prevent pathogen infections.

Thus, together with the pathogen risk module, the digital vaccine module provides a way to eliminate or abate the effects of infectious disease, complementary to and synergistically with biological vaccines, by improving overall and specifically immune health in advance of exposure to a pathogen and to provide guidance on behaviors or actions for avoiding or resisting pathogens. Specifically, the modules protect individuals and communities by acting on the first of the three events characteristic of infectious diseases: infectious contact. They help individuals (or broader groups of individuals) avoid actions that might cause individuals to contract the disease, or allow the disease to affect individuals' bodies in deleterious ways. Knowledge derived from scientific evidence about risks involved with behavior, events and businesses can help individuals predict what protective actions (unique to that individual, or even to a larger subpopulation) to take or avoid, or other factors or environments to engage in or avoid. By providing the user with such scientific evidence, personalized to the specific condition of the user itself, the modules contribute as well to promoting the use of biological vaccines through awareness and individual engagement. Such "digital vaccines" protect not only the individual to whom the digital vaccine is "administered," but also entire populations or subpopulations. This means that while vaccines may seem like a personal choice, digital vaccination protects the entire population by suggesting virtuous behaviors that limit the spread of the disease.

Goals Module

The goals module provides a goal creation function of the user interface that users are able to use in order to create goals that are subsequently tracked and/or updated by the goals module. In particular, upon selection of the goal creation function, the goals module provides the users with a goal creation interface that enables the users to create one or more increase, decrease or replace goals. In some embodiments, one or more of the possible goals (as determined by the current nutrition, physical activity and/or social activity data of the user's profile) are able to be automatically displayed to the user upon selection of the goal creation function button. Specifically, the goals module is able to automatically determine the possible increase, decrease and/or replace goals based on the user's current food intake, physical activity and social activity values and display one or more of them to the user upon selection of the goal creation function. Alternatively or in addition, rather than displaying possible goals automatically, the goal creation interface is able to enable users to select a type of goal (e.g. increase, decrease or replace) and/or type of activity (e.g. nutrition, physical activity, social activity, stress) they would like to create and then displays possible goals of that type of goal and/or activity. For example, the goal creation interface is able to display possible goals for increasing the user's vigorous exercise, decreasing a user's social media time, replacing surplus dairy intake with vegetable intake and/or other similar goals that correspond to the user's current profile data and/or scores.

For nutrition based goals, if the remaining calories quantity of the user (as determined by the free calories function 714) is greater than 0, the goal creation interface is able to display a separate increase intake goal for each of the food categories (e.g. diary, fruit, seafood/plant proteins, vegetables, oils, whole grain, refined grain, meat/eggs) whose intake level for the user is less than the optimal intake amount for that food category (as also used by the food function 718 above). Upon selection of one of the increase intake goals by the user, the goal creation interface enables the user to specify how much of an increase amount the goal is for (with a maximum increase amount set to the lower of: the optimum intake amount for that food category and the amount of the remaining calories quantity that has not already been allocated to another increase goal). In some embodiments, the meat/eggs and/or refined grain categories are restricted from receiving any of the remaining calories and so are not presented to the user as a possible increase goal. For any of the food categories that have a current intake value that is higher than the optimal amount (or maximum allowed amount) and/or for other intake types (e.g. alcohol, processed food, caffeine empty calories and sodium), instead of displaying an increase goal, the goal creation interface is able to display a separate decrease intake goal. Upon selection of one of the decrease intake goals by the user, the goal creation interface enables the user to specify how much of a decrease amount the goal is for (with a maximum decrease amount set to: the difference between the current intake for that food category and the optimum intake for that food category; or the difference between the current intake value and 0 for the other intake types).

Further, for a first food category that the user selects to be increased with an increase goal, but has a current intake level that is greater than the optimal amount for that first food category, the goal creation interface is able to display a replace goal. Upon selection of the replace goal by the user, the goal creation interface presents and enables the user to select a second food category (from a set of the food categories which the user currently has an intake amount that is larger than the optimum amount and/or from any intake value of the other intake types) from which they'd like to decrease their intake in order to enable them to increase their intake in the first food category. The goal creation interface then enables the user to specify how much of a decrease/increase amount the replace goal is for (with a maximum decrease/increase amount set to the difference between the current intake for the second food category and the optimum intake for that second food category). Similarly, in some embodiments for a first food category that the user selects to be decreased with a decrease goal, but has a current intake level that is less than or equal to the optimal amount for that first food category, the goal creation interface is able to also display a replace goal. Upon selection of the replace goal by the user, the goal creation interface presents and enables the user to select a second food category (from a set of the food categories which the user currently has an intake amount that is smaller than the optimum amount) from which they'd like to increase their intake in order to enable them to decrease their intake in the first food category. The goal creation interface then enables the user to specify how much of a decrease/increase amount the replace goal is for (with a maximum decrease/increase amount set to the difference between the optimum intake for the second food category and the current intake for the second food category).

For physical activity based goals, an increase goal to increase moderate activity is enabled and/or presented if: the current moderate activity level is less than or equal to 300 and age of the user is less than 65. An increase goal to increase vigorous activity is enabled and/or presented if the user is not lactating or pregnant and: the current vigorous activity level is less than or equal to 150 and age of the user is less than 65; or the current vigorous activity level is less than or equal to 75 and age of the user is greater than or equal to 65. An increase goal to increase resistance activity is enabled and/or presented if the user is not lactating or pregnant and the current resistance level is less than 2. Upon selection of one of the increase physical activity goals by the user, the goal creation interface enables the user to specify an increase amount of how much time or many resistance sessions the user would like to increase their moderate, vigorous or resistance activity. In some embodiments, the increase amount has a maximum of: 300 if the user is less than 65 for moderate activity; 150 if the user is less than 65 or 75 if the user is greater than or equal to 65 for vigorous activity; or 2 for resistance activity.

Similarly, a decrease goal to decrease moderate activity is enabled and/or presented if: the current moderate activity level is greater than 300 and age of the user is less than 65. A decrease goal to decrease vigorous activity is enabled and/or presented if the user is not lactating or pregnant and: the current vigorous activity level is greater than 150 and age of the user is less than 65; or the current vigorous activity level is greater than 75 and age of the user is greater than or equal to 65. A decrease goal to decrease resistance activity is enabled and/or presented if the user is not lactating or pregnant and the current resistance level is greater than 2. Upon selection of one of the decrease physical activity goals by the user, the goal creation interface enables the user to specify a decrease amount of how much time or many resistance sessions the user would like to decrease their moderate, vigorous or resistance activity. In some embodiments, the decrease amount has a maximum of: the user's current amount minus 300 if the user is less than 65 for moderate activity; the user's current amount minus 150 if the user is less than 65 or 75 if the user is greater than or equal to 65 for vigorous activity; or the user's current amount minus 2 for resistance activity.

A replace goal for moderate/vigorous physical activity is able to be substantially similar to a replace goal for nutrition goals, as described above. Specifically, increases/decreases to moderate and/or vigorous activity for which the user is already at the maximum/minimum for that activity type can be the basis of a replace goal with the amount of time increased from one type of activity combined with a decrease in the other type of activity. In some embodiments, for a replace goal, vigorous activity time is equated to a scaling factor X of moderate activity time. Thus, for the replace goal to be balanced, the goal module ensures that a time T increased/decreased from vigorous activity is balanced by a time T*X decreased/increased from moderate activity.

A replace goal to replace resistance activity with moderate and vigorous activity is enabled and/or presented if current resistance training sessions is greater than 2 and the user is not pregnant or lactating and: the current moderate activity level is between 0 and 300 and the current vigorous activity level is between 0 and 150 and age of the user is less than 65; or the current moderate activity level is between 0 and 150 and the current vigorous activity level is between 0 and 75 and age of the user is greater than or equal to 65. A replace goal to replace resistance activity with vigorous activity is enabled and/or presented if current resistance training sessions is greater than 2 and the user is not pregnant or lactating and: the current moderate activity level is greater than 300 and the current vigorous activity level is 0 and age of the user is less than 65; or the current moderate activity level is greater than 150 and the current vigorous activity level is 0 and age of the user is greater than or equal to 65. A replace goal to replace resistance activity with moderate activity is enabled and/or presented if: the user is pregnant or lactating and current resistance training sessions is greater than 0; or the user is not pregnant or lactating, current moderate activity is equal to 0, and the current resistance training sessions is greater than 2 and: the current vigorous activity level is greater than 150 and age of the user is less than 65; or the current vigorous activity level is greater than 75 and age of the user is greater than or equal to 65.

Upon selection of the replace goal by the user, the goal creation interface presents and enables the user to specify how many of the resistance sessions to decrease (with a maximum decrease equal to the current number of resistance sessions) and an amount of time to increase moderate activity and/or vigorous activity time. In some embodiments, for a resistance replace goal, each resistance session is equated to X minutes of moderate activity time and Y minutes of vigorous time. Thus, for the resistance replace goal to be balanced, the goal module ensures that the number of decreased resistance sessions=(moderate activity time added*X)+(vigorous activity time add*Y).

For social activity based goals, a social activity increase goal to increase social activity is enabled and/or presented for one or more of the social categories (e.g. family time, friends time, purposeful life time, religious services time, sports time, volunteering time). In some embodiments, one or more of the social categories of which the user currently spends the most time on are not presented as an increase goal option. Upon selection of one of the increase social activities goals by the user, the goal creation interface enables the user to specify an amount of time to increase the selected activity. A social activity decrease goal to decrease social activity is enabled and/or presented for the social media time if: the age of the user is less than 65 and the current social media time is greater than a first threshold (e.g. 15 hours a month); or the age of the user is greater than or equal to 65 and the current social media time is greater than a second threshold (e.g. 30 hours a month). Upon selection of the decrease social activities goal by the user, the goal creation interface enables the user to specify an amount of time to decrease the social media activity.

After input of this goal data, each of the goals are able to be generated and stored on the platform 99 (e.g. on the servers 102 and/or the user device 104) along with the user profile data until the goal has been completed or aborted. As a result, the platform 99 is able to keep track of multiple goals generated by the user as they are associated with the user's profile on the platform 99.

Figure 10:
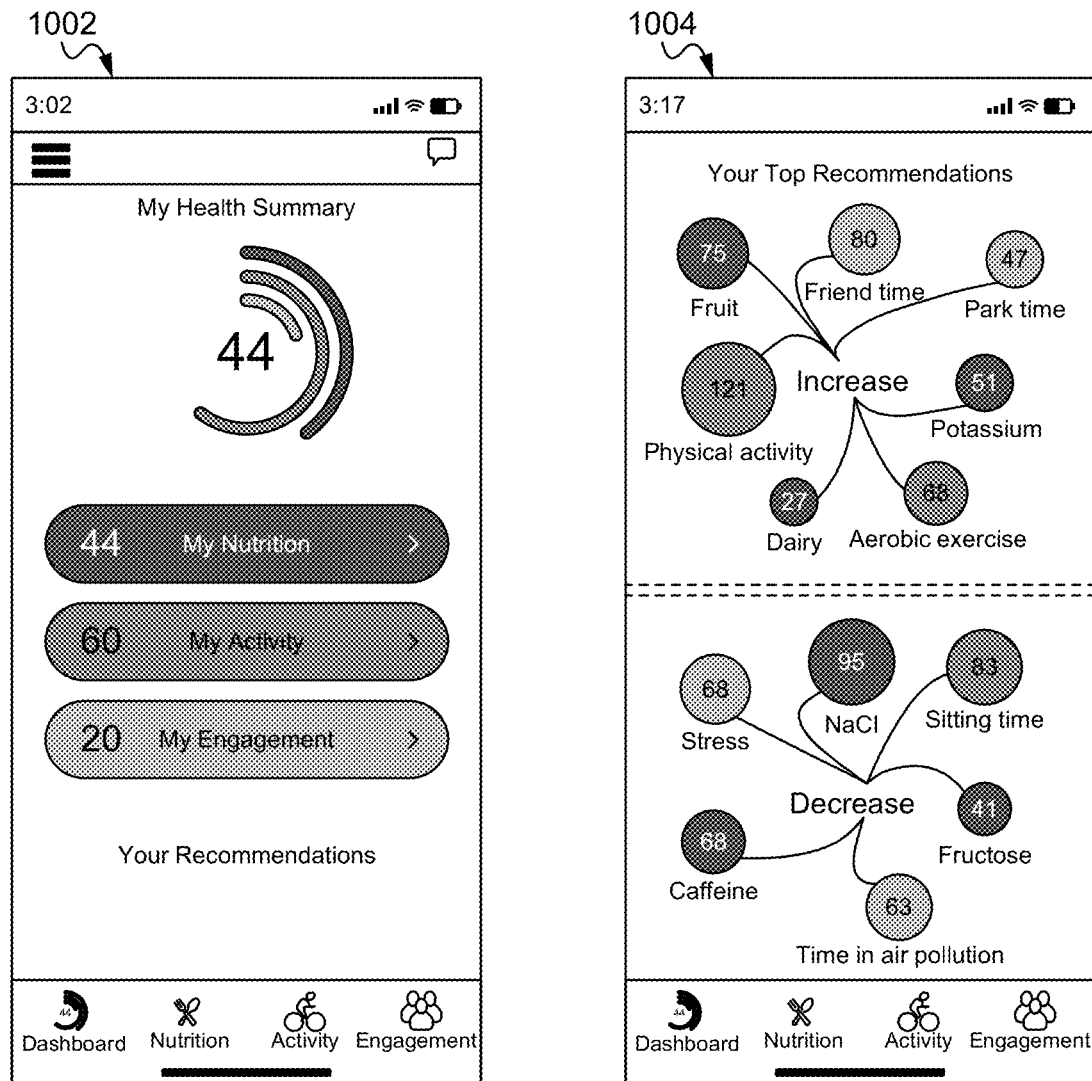
FIG. 10 illustrates a screenshot of a user interface of the recommendation module enabling the presentation of recommendations according to some embodiments.

Alternatively or in addition, the goal module is able to enable generation of a new goal based on selection of a goal creation function associated with one or more of the factors 324 (e.g. displayed as a recommendation as shown in FIG. 10, displayed within a user network 320 or factor ID list 318 as shown in FIGS. 3B and 3C; displayed as a factor 324 associated with an article as shown in FIG. 3D) of the platform 99. For example, one or more of the displays of the factors 324 are able to include a goal icon (that is always displayed or appears after selection of the factor 324), that when selected, opens the goal creation interface with a list of goal options for creating a goal directed to the selected factor (e.g. based on what goal parameters are possible given the user's current profile data and/or scores). Specifically, the module presents and enables the user to select whether they would like to increase or decrease the selected factor (wherein if the increase or decrease is not permitted as described above, the goal is converted to a replace goal).

This method of generating a goal is substantially similar to the method described above except that the goal module determines which food category, other category (e.g. alcohol), physical activity type or social activity type the selected factor belongs to and then treats the goal in the same manner as an increase, decrease or replace goal of such a food category, other category (e.g. alcohol), physical activity type or social activity type (as described above). For example, if the user selects the create a goal icon associated with a factor of kale shown on the platform 99, the goals module is able to determine that the factor kale is in the food category of vegetables and then perform the goal creation process in the same manner as a vegetable category nutrition based goal as described above (except with the goal specifying kale as being specifically increased or decreased rather than vegetables as a whole). In some embodiments, if a first factor that is a food belonging to one of the food categories is selected for a replace goal, but none of the other categories of food (or the other intake types) have a current intake value that enables them to be used to offset the increase or decrease of the factor, the goal module enables second food factor from the same food category to be selected to offset the desired increase/decrease of the first food factor. For example, if a user wants to create a goal to increase the amount of the food factor kale that they ingest, but are unable to offset the calories with those from other food categories (or other intake types), the module enables the user to choose another food factor of the vegetable category (e.g. cucumber) to be a part of the replace goal. Thus, the goal module provides the improvement of enabling users to select specific factors as the subject of goals and automatically presenting goal options that work with the selected factor.

In some embodiments, the goals module is also able to include a notification feature that reminds the user about their goal, prompts the user to submit whether they have been meeting their goal (and/or updating their profile values to reflect the changes caused by meeting their goal), determines a goal completion percentage and/or determines whether a goal has been completed. In such embodiments, during the goal generation process described above, the goal module further prompts the user to input a goal frequency and/or a goal duration for each of the goals. The goal frequency determines how often the notification feature sends a reminder to the user to comply with their goal and/or to update their user profile with characteristic changes (e.g. decreased intake of empty calories) caused by meeting their goal. The goal duration indicates how long the goal should last (e.g. a number of days, weeks, months, years) and/or an end condition of the goal (e.g. after a number of consecutive days, weeks, months, years of meeting the goal). In some embodiments, if a user does not input a goal frequency and/or goal duration, the notification feature uses a predefined default goal frequency (e.g. daily, weekly, monthly) and/or default goal duration (e.g. one week, one month, one year).

Once the frequency and/or duration have been input and the goal has been created and stored on the platform 99, the goal notification function automatically sends reminders to the user at the goal frequency asking if they complied with their goal (since the last reminder) and enabling the user to confirm compliance, confirm non-compliance or abort the goal entirely. The reminders are able to identify the subject(s) of the goal (e.g. the element(s) to be increased/decreased), the quantity of each subject to be increased/decreased and/or other details about the goal (e.g. frequency, duration, progress value). If the user selects the abort option, the goal is deleted. Otherwise, each time compliance or non-compliance is confirmed, the goal notification function updates a progress value for the goal stored with the goal on the platform 99. For example, if a goal has a goal frequency of daily and a goal duration of 10 days, the goal notification function is able to send a reminder each day at a trigger time (e.g. 8 p.m.). If the user confirms non-compliance, the progress value is not changed, but if the user confirms compliance, the progress value is incremented by the frequency divided by the duration (where both the frequency and duration are converted to days or other matching units). Thus, in the above example, after the first and second reminders, if the user confirmed compliance for both, the progress value would be 20% or 2/10. Alternatively, the progress value is able to be incremented by the total frequency value upon confirmation of compliance (e.g. if there is no duration). Thus, in the above example, after the first and second reminders, if the user confirmed compliance for both, the progress value would be 2. These reminders are continuously sent and progress values continuously updated until the goal is aborted or finishes its duration.

In some embodiments, after submitting their confirmation, for each goal, the goal notification function displays a representation of the progress value to the user (e.g. as a progress bar with a length corresponding to the progress value and/or a percentage value equal to the progress value divided by the duration). In some embodiments, upon completion of a goal due to the expiration of its duration, the goal notification function presents the representation of the progress value indicating how the user performed over the total of the goal and/or enables the user to renew the goal if desired. In such embodiments, a completion message is also able to be transmitted to the user which is based on the progress value (e.g. with high progress values resulting in a congratulatory message and lower progress values resulting in encouragement to keep trying messages). The completion message is able to be selected from a set of completion messages in a message table based on the progress value. In some embodiments, the confirmations are able to be omitted and/or the goals module is able to use direct measurements from the user device 104 to update the goal progress value. For example, for physical activity goals, the user is able to use exercise related measurement functions (e.g. heart rate) of the user device 104 to confirm compliance or non-compliance.

If the user selects the renew option, the goal notification function resets the start date of the goal to the current date such that the goal's duration begins again. In such embodiments, the progress value is able to be maintained from the original goal to the renewed goal, with the duration doubled for the purposes of the representation of the progress value and calculation of the increment to the progress value. Alternatively, the progress value is able to be reset to 0 for the renewed goal and the duration is able to remain the same for the representation of the progress value and calculation of the increment to the progress value.

In some embodiments, after the user fails to reply and/or replies with a confirmation of non-compliance to a predetermined number of reminders, the goal notification function is able to send one or more additional reminders in between frequency times and/or include encouragement messages with the additional reminders, wherein the encouragement messages are selected from a table of encouragement messages based on the progress value of the goal. In some embodiments, the goal notification function is able to stop sending the additional reminders after the user confirms compliance with the goal for a predetermined number of reminders after commencing the sending of the additional reminders. In some embodiments, for each of the goals, the goal notification function enables the user to change the trigger time from a default time of day to any other desired time. In some embodiments, the reminders are able to be sent to the user on the user device 104 even if the platform is not open on the device 104 (e.g. sent from the background of the device 104). In some embodiments, if a user has multiple goals, the goal notification function is able to send multiple goal reminders at each of their goal frequencies (at their trigger times) and/or send a group reminder for any of the goals that share a reminder day (and/or trigger time).

In some embodiments, the goals module is able to dynamically update the affected scores of the user based on changes to a user's goal progress and/or completion of their goal. Specifically, these dynamic updates to the scores are able to be calculated each time a user confirmation causes a change to the progress value of a goal (e.g. at each reminder and/or completion that changed the progress value). Alternatively, the module is able to only update the affected scores upon goal completion (not at every reminder that results in a change to the progress value). In particular, the goals module is able to determine the compliance percentage equal to a number of times the progress value has been incremented divided by the total number of reminders (or just the progress value if the calculation is based on completion of the goal). Then the goals module is able to multiply the completion percentage by the increase and/or decrease amounts of the goal and adjust the associated nutrition, physical activity and/or social activity values by the result.

For example, if the user confirmed compliance 30 times in response to 40 reminders, the completion percentage is 30/40 or 75 percent. Now, assuming that the user goal was to decrease 8 oz. a week of meat, the module updates the meat intake value of the user by decreasing it by 8 oz. multiplied by 75% (i.e. 6 oz.), and recomputes the nutrition score for the user. This is able to be the same for physical activity and social activity types and scores. In some embodiments, if the completion percentage is below a threshold value (e.g. 80 percent) the goals module refrains from recalculating the scores. In some embodiments, for personal characteristics having nominal values (e.g. sodium intake=high), there is no increase/decrease value so the completion percentage cannot be multiplied by the decrease/increase value and instead the nominal value is changed from its current value to the goal value if the completion percentage is above the threshold value. For example, for a goal by a user to reduce sodium intake from high to low, if the completion percentage is above the threshold value, the goals module changes the sodium intake value to low and recalculates the nutrition score. If instead the completion percentage is below the threshold value, the goals module leaves the current sodium intake value at high (and no recalculation is necessary).

Finally, the goals module is able to also comprise a current goals function. In particular, once a goal has been created, upon selection of the current goals feature, the goals module is able to present each of the pending goals along with information about those goals including, but not limited to: type of goal, amount of goal, subject(s) of goal, amount of time goal has been active, goal start date/time, goal end date/time, goal notification frequency and/or other goal data. Further, the current goals feature enables the user to delete or modify any currently pending goals (e.g. modify their duration, increase/decrease amount, end data/time, notification frequency and/or other goal data described herein).

Thus, the goals module provides the improvement of enabling users to not only set goals for increasing or decreasing certain activities/foods, but also to create replacement goals that balance out any inequities in their life that would be caused by a desired increase or decrease of their nutrition, social and/or physical activities. Additionally, it should be noted that although the above description defines one or more maximum or minimum increase/decrease values and/or optimum food intake or physical activity values, other values are able to be used as the maximum or minimum thresholds.

Mental Health Module

The mental health module determines a stress score for the user based on stress data derived from or found within their personal characteristics. Specifically, the mental health module is able to holistically evaluate sources of stress of the user (as input by the user and/or detected by use devices 104) and combine the stress or anti-stress effects of those sources in order to determine the stress score of the user. This stress score is then able to be used by the platform 99 to assign one or more stress-related conditions to the user. For example, if the user has a poor stress score (e.g. less than 13 on a scale of 100) the mental health module is able to assign the condition of overstressed and/or hypertension that will stay associated with the user until their stress score changes enough to no longer qualify for the condition. Further, as described in the recommendation module below, these assigned conditions of the user are able to be used for determining one or more matching tuples of the knowledge base 106 from which recommendations for the user are derived. This stress data and/or score is then able to be added to the user profile of the user and/or be dynamically updated by the module based on newly submitted data by the user and/or data measured/input from one or more coupled devices (e.g. smart phone, smart watches). As a result, the mental health module provides the advantage of enabling a user to not only determine their overall stress levels, but also to receive recommendations of how to lower their stress level.

In particular, the mental health module is able to determine an average occupational stress level for the user based on the occupation of the user profile and an occupation stress table that associates a plurality of occupations with an average stress level for that occupation. The occupation stress table is able to be stored on the platform 99 and/or accessed via the network 110 from a third party data source 108. For example, the occupation stress table is able to be similar to the occupation physical proximity table (e.g. via o-net online) described herein, except that each of the occupations is associated with an average occupational stress level instead of a physical proximity value. In some embodiments, once the mental health module has determined the average occupational stress level of the user, the module is able to adjust the occupational stress level based on the user's work commute distance and/or transportation method (e.g. as input by occupation page 424 of the personal characteristics module and/or as input by the mental health module directly). Specifically, the occupational stress level is able to be reduced by non-motorized transportation methods (e.g. walking, biking, skating, roller blading, roller skating) and/or increased by motorized transportation methods (e.g. cars, buses, trains, subways, motorcycles, etc.).

For example, in some embodiments the adjusted occupational stress level is equal to: average occupational stress level÷5 if transportation method is non-motorized; (average occupational stress level÷5)*(distance weight A+(commute distance in miles÷10)) if transportation is non-enclosed vehicle (e.g. motorcycle, motorized bike); (average occupational stress level÷5)*(distance weight B+(commute distance in miles÷10)) if transportation method is enclosed vehicle (e.g. car, bus, train, subway); and (average occupational stress level÷5)*(distance weight C+(commute distance in miles÷10)) for all other transportation methods or if no method specified. In particular, distance weight A is able to be 1, distance weight B is able to be 1.4 and distance weight C is able to be 1.8. Alternatively, other distance weights are able to be used and/or the mental health module is able to not adjust the original average occupational stress level.

Additionally, in some embodiments the mental health module is able to determine a non-occupational stress level that is able to be combined with the occupational stress level (adjusted or non-adjusted) in order to determine an overall stress score for the user. Alternatively, overall stress score is able to be equal to just the occupational stress score or just the non-occupational stress level.

The non-occupational stress level is able to be based on user profile characteristic data and/or questionnaire-based stress elements. The stress elements are able to include, but not limited to, one or more of wellness, thought control, active stress coping, social ease, tension reduction, spiritual practice and/or other stress elements. In particular, these elements are able to be determined by the mental health module based on the user profile data (as entered via the other modules and/or directly by the mental health module) and user-submitted answers to questions of a questionnaire. Specifically, the mental health module is able to present and receive answers to each of the questions of the questionnaire from the user, wherein subsets of the questions relate to the one or more of wellness, thought control, active stress coping, social ease, tension reduction, spiritual practice and/or other stress elements. For example, in some embodiments of 26 questions, three questions are able to relate to wellness, six questions are able to relate to thought control, seven questions are able to relate to active stress coping, six questions are able to relate to social ease, two questions are able to relate to tension reduction, and two questions are able to relate to spiritual practice. The questions are able to be multiple choice and the answers to each of the questions are each able to have an assigned value (e.g. a=4; b=3; c=2; and d=1). As a result, the health module is able to determine an initial score for each of the stress elements based on the sum of the values of the answers the user provided for the questions directed to that stress element. Thus, if a user selected answer A for all four questions related to social ease they would have an initial social ease score of 16 (e.g. 4+4+4+4).

The profile characteristic data is able to include one or more of a weight score, a purposeful time score, a religious time score, an exercise score, a smoking score, a nutrition stress score and/or other characteristic data. The weight score is able to be based on how close the user's weight is to their target weight as indicated by their ideal body weight (IBW) or their body mass index (BMI) weight (which is able to be determined by the module based on their input height, weight, age, sex and other characteristics input by the personal characteristics module). For example, in some embodiments if they are within a first percentage (e.g. 1 percent) of their target weight their weight score is 4; if they are within a second percentage (e.g. 10 percent) of their target weight their weight score is 3; if they are within a first percentage (e.g. 20 percent) of their target weight their weight score is 2; if they not within the third percentage of their target weight their weight score is 1. In such embodiments, if a user had a weight of 165 pounds and a target weight of 150 pounds, they would have weight score of 2 (because 165 is within 10 percent of 150, but not within 1 percent).

The nutrition stress score is able to be directly based on the user's nutrition score as described herein. For example, the nutrition stress score is able to be equal to: 4 if their nutrition score is greater than 90; 3 if their nutrition score is greater than 70, but less than or equal to 90; 2 if their nutrition score is greater than 50, but less than or equal to 70; and 1 if their nutrition score is less than or equal to 50. Alternatively, other ranges are able to be used. Similarly, the exercise score is able to be directly based on the user's PA score and/or PA level (e.g. professional athlete, physical job, vigorously active, moderately active, lightly active, sedentary) as determined by the classification function 520. For example, the exercise score is able to be equal to: 3 if their PA level is moderately active; 2 if their PA is lightly active; 1 if their PA level is sedentary; and 4 for all other PA levels (e.g. professional athlete, physical job and vigorously active).

The smoking score is able to be based on whether they currently smoke, previously smoked or have never smoked (as indicated by the personal characteristics module and/or input by the mental health module directly). For example, the smoking score is able to be equal to: 4 if they have never smoked; 2 if they previously smoked; and 1 if they are currently a smoker. The purposeful time score is able to be based on the amount of purposeful and religious time the user spends a month (as indicated by the personal characteristics module and/or input by the mental health module directly). For example, the purposeful time score is able to be equal to: 4 if their monthly purposeful time+religious time is greater than 15 hours; 3 if their monthly purposeful time+religious time is greater than 4 hours; 2 if their monthly purposeful time+religious time is greater than 1 hour; and 1 if their monthly purposeful time+religious time is equal to or less than 1 hour. Similarly, the religious time score is able to be based on the amount of religious time the user spends a month (as indicated by the personal characteristics module and/or input by the mental health module directly). For example, the religious time score is able to be equal to: 4 if their monthly religious time is greater than 20 hours; 3 if their monthly religious time is greater than 10 hours; 2 if their monthly religious time is greater than 4 hours; and 1 if their monthly religious time is equal to or less than 4 hours.

Further, the module is able to adjust one or more of the initial scores of the stress elements based on normalizing weights and/or the weight score, the purposeful time score, the religious time score, the exercise score, the smoking score, the nutrition stress score. Specifically, the module is able to determine an adjusted wellness score equal to: ((initial wellness score+weight score+nutrition stress score+exercise score+smoking score)/7)*25, wherein dividing by the number of wellness questions plus the number of other scores and multiplying by 25 normalizes the score to be between 0 and 100. The module is able to determine adjusted thought control, adjusted active stress coping, adjusted social ease and adjusted tension reduction scores as each being equal to: ((initial X score)/the number of questions used to determine initial score)*25, wherein dividing by the number of questions and multiplying by 25 normalizes the adjusted X score to be between 0 and 100. Lastly, the module is able to determine an adjusted spiritual practice score equal to: ((initial spiritual practice score+purposeful time score+religious time score)/4)*25, wherein dividing by the number of spiritual practice questions plus the number of other scores and multiplying by 25 normalizes the score to be between 0 and 100.

The mental health module is able to combine one or more of these non-occupational stress elements to determine a total non-occupational stress level of the user. For example, in some embodiments the non-occupational stress level is able to be equal to: (adjusted wellness score+adjusted thought control score+adjusted active stress coping score+adjusted social ease score+adjusted tension reduction score+adjusted spiritual practice score)/6. Alternatively, one or more of the initial values are able to be used instead of the adjusted values when determining the total non-occupational stress level of the user.

Finally, the mental health module is able to determine an overall stress score for the user based on the occupational stress level (adjusted or unadjusted) and/or the non-occupational stress level. For example, in some embodiments the stress score is equal to: adjusted occupational stress level*occupational stress weight)+(the non-occupational stress level*non-occupational stress weight), wherein the occupational stress weight and the non-occupational stress weight add up to 1. Thus, if occupational stress is determined to be more of a factor than non-occupational stress, the occupational stress weight is able to be 0.8 and the non-occupational stress weight is able to be 0.2. Alternatively, other stress weights are able to be used. Also, in some embodiments the mental health module is able to make a household adjustment to the overall stress score, wherein if a user lives alone (e.g. household of one) the module subtracts a predetermined penalty (e.g. 5) from the overall stress score. Accordingly, the mental health module provides an improvement by including both occupational and non-occupational stress elements as well as the effects that specific characteristics of the user have on those elements.

In some embodiments, as described above, analysis of the user's genetic risk scores based on input genetic data (e.g. DNA sequence or genotyping data) are able to provide additional information on a user's susceptibility to mental health conditions (e.g., depressive personality disorders, dementia, addictions). These risk scores are able to be incorporated into the individual's overall characteristics and used for adjusting the scoring modules and therefore subsequent recommendations. In other embodiments, the mental health risk score can be modified when a user takes a prescription or over-the-counter medication for treating or managing the condition (e.g., lithium for bipolar disorders). Risk scores are able to be modified by the use of the drug or supplement.

Recommendation Module

The recommendation module inputs the user profile data as input by one or more of the other modules described herein, compares that data to the tuples of the knowledge base, determines one or more recommendations based on the user profile data (and/or the scores/status derived therefrom) and the tuples, and presents one or more of those recommendations to the user. For example, the recommendations module is able to search the knowledge base 106 for conditions and/or factors that match one or more of the user profile data (e.g. user demographic data, user treatment data, user outcome data, health conditions, user diet, current medications, sleep score range, stress score range, physical activity score range, social activity score range, pathogen score range, nutrition score range, user conditions derived from one or more of the scores/score ranges and/or other characteristics input by the characteristics module), and if there is a match, provide a recommendation based on one or more of the tuples that include the matching conditions and/or factors. For example, if a user has a condition of hypertension (as input by the personal characteristics module), or a condition of sedentary (as calculated by the physical activity module), or a social activity score in a predefined low range (as calculated by the social activity module), the recommendation module is able to search for tuples of the knowledge base 106 having that condition (and/or having metadata that matches that of the user) and provide one or more factors of those tuples as recommendations to address that condition.

Specifically, if the matching factor is associated with many undesirable conditions, the module is able to recommend avoiding/reducing the matching factor, increasing or introducing factors that offset/decrease the effects of the matching factor, or both (as indicated by the tuples of the knowledge base 106). Similarly, if the matching condition is undesirable, the module is able to recommend introducing or increasing factors that decrease the matching condition and/or recommend stopping, decreasing factors that increase the undesirable condition or both (again as indicated by the tuples of the knowledge base 106). In some embodiments, the recommendation module is able to filter the tuples based on their associated metadata and the demographic data of the user profile (e.g. sex, zip code, medications, age, current conditions/statuses or other characteristics of the user within their user profile) such that only the tuples whose metadata indicate that they apply to the demographics of the user are used to determine recommendations for the user as described above. Similarly, in some embodiments, one or more of the tuples are able to be filtered based on the input allergies of the user such that the module will not recommend increasing or introducing a factor that the user is allergic to.

In some embodiments, if the quantity of recommendations matching a user's profile exceeds a predetermined amount, the recommendation module is able to select a subset of the matching recommendations equal to or less than the predetermined amount to provide to the user. For example, the recommendation module is able to rank the recommendations based on the relationship strength of the tuples (and/or the ranking of the documents from which the tuple is derived) and select the recommendations based on the tuples having the highest relationship strength (and/or document ranking). Alternatively or in addition, the recommendation module is able to rank the recommendations based on the severity of the positive or negative matching condition/factor and select recommendations based on the tuples having the most severe effects (e.g. the condition of cancer would be ranked higher than the condition of acne). Alternatively or in addition, the recommendation module is able to adjust the ranking of the recommendations based on whether they have been previously presented to the user and/or how long they have been presented to the user. Specifically, the ranking of a recommendation that has been presented more times and/or for a longer period of time is able to be lowered with respect to recommendations that have been presented less and/or for a shorter period of time. Alternatively or in addition, a factor of randomization is able to be introduced to the recommendation selection process in order to ensure that the same recommendations are not always repeated and/or the same recommendations are not always overlooked.

In any case, because the user profile has been expanded in order to take into account environmental and genetic susceptibility parameters as well as other parameters, the recommendation module is able to improve on prior art by determining more customized and accurate recommendations for the user that are more likely to produce the desired results.

FIG. 10 illustrates a screenshot of a user interface of the recommendation module enabling the presentation of recommendations according to some embodiments. As shown in FIG. 10, the user interface provides a summary page 1002 and/or a top recommendations page 1004 that present the users with one or more of their current scores (e.g. physical activity, sleep, nutrition, social activity, pathogen risk, stress) as well as recommendations of factors and/or conditions to increase and/or decrease. For example, as shown in FIG. 10, recommendations for each individual are in the form of filled circles with the size representing the strength of the relationship for the individual's age, sex, physiological status (e.g., pregnancy), genetic susceptibility and condition. The number within the circle is the numerical strength of the relationship (as described above). In some embodiments, selecting any circle opens a new page with a summary of the number of documents supporting the recommendation and/or the tuples upon which it is based (e.g. as shown in FIG. 3D).

In some embodiments, the recommendation module includes an update function that is able to determine whether complying with the recommendations alters the user's scores and/or update recommendations and/or tuples based on user feedback. For example, complying with a social distancing recommendation is able to reduce an individual's social activity score and therefore individual lifestyle score. In particular, the update function is able to periodically, randomly, or upon demand, query the user as to whether they have been compliant with one or more of the recommendations. If the user indicates that they have been compliant, the module is able to ask the user to update some or all of the profile data that they input using the other modules described herein. Then based on any changes to the profile data, the recommendation module is able to adjust the recommendations and/or tuples upon which the recommendation was based, discontinue use of the recommendation/ tuples and/or create a new recommendation/tuple.

For example, if the recommendations with which the user was compliant did not result in the change indicated by the tuple(s) in the condition/factors upon which they were based, the module is able to delete, remove from consideration for this user, and/or lower the rank and/or relationship score of the recommendation/tuple. Similarly, if the recommendations with which the user was compliant did result in the change indicated by the tuple(s) in the condition/factors upon which they were based, the module is able to increase the rank and/or relationship score of the recommendation/ tuple. Further, in some embodiments if the input changes indicate new conditions/factors, the module is able to generate a new recommendation and/or tuple that is able to be added to the knowledge base 106. In some embodiments, the change input by the user is measured based on the changes to one or more of their scores, wherein increases in score indicate that the recommendation is working and decreases in score indicating that the recommendation may need to be updated, deleted and/or reevaluated.

In some embodiments, even if the user has not updated their profile data and/or has not indicated whether they have been complying with one or more of the recommendations, the recommendation module is able to generate new recommendations for the user based on new tuples that have been created and added to the knowledge base 106 since the last time recommendations were generated for the user. In some embodiments, each time the user updates their profile data, the recommendation module determines one or more recommendations to provide to the user based on the new profile data. Indeed, these changes in recommendation can be initiated by the user acquiring a new condition (e.g. going from sedentary to active as determined by the platform 99) such that factors associated with the previous condition (e.g. sedentary) are no longer used as recommendations and/or factors associated with the new condition are able to be used as recommendations. Similarly, if a user's update to their profile data causes their scores to change (e.g. sleep, physical activity, social activity, nutrition, pathogen, stress) any recommendations based on the condition of having the previous score are able to be removed and/or new recommendations based on the condition of having the current score are able to be added. For example, a user having a low sleep score (e.g. within a predefined low range) would be recommended factors that help the condition of poor sleep, wherein if their sleep score increases out of the low range, those recommendations are able to be removed and/or new ones based on the new range added. Similarly, if changes to the user's profile data cause the user to no longer correspond to the metadata of one or more tuples from which recommendations where derived, those recommendations are able to be removed and/or new recommendations determined based on the tuples having metadata that corresponds to that of the user's updated profile. Further, in some embodiments if a user creates a goal based on a factor of a recommendation using the goals module described above, the recommendation module is able to remove that recommendation (and the tuple upon which it is based) from consideration until the goal is completed and/or deleted so as to not recommend something that the user has already indicated as a goal and is working toward. In some embodiments, the module only asks the user to update the profile data that was used to determine the recommendation (e.g. was used to match the condition and/or factors, was used to derive the scores). Alternatively, the module is able to ask the user to update all of their profile data.

As a result, the recommendation module provides the advantage of analyzing real-world user data in the context of a user's specific environment and identifying known factors that ultimately lead to the discovery of previously undetected associations, to better understand health and disease processes.

Methods of Operation

Figure 14:
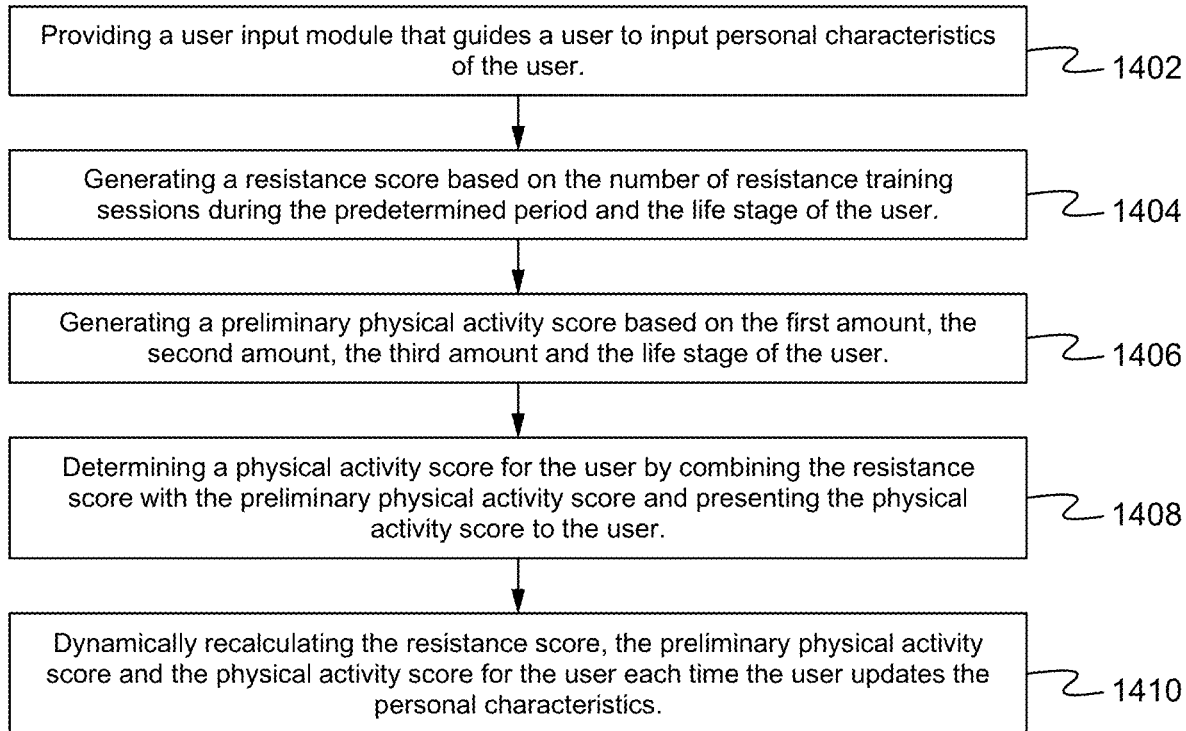
FIG. 14 illustrates a method of implementing a personal health platform for providing physical activity scores and promoting healthy choices to one or more users according to some embodiments.

FIG. 14 illustrates a method of implementing a personal health platform 99 for providing physical activity scores and promoting healthy choices to one or more users according to some embodiments. As shown in FIG. 14, the platform 99 provides a user input module that guides a user to input personal characteristics of the user at the step 1402. In some embodiments, the personal characteristics comprise at least a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity. The platform 99 generates a resistance score based on the number of resistance training session during the predetermined period and the life stage of the user at the step 1404. The platform 99 generates a preliminary physical activity score based on the first amount, the second amount, the third amount and the life stage of the user at the step 1406. The platform 99 determines a physical activity score for the user by combining the resistance score with the preliminary physical activity score and present the physical activity score to the user at the step 1408. The platform 99 dynamically recalculates the resistance score, the preliminary physical activity score and the physical activity score for the user each time the user updates the personal characteristics at the step 1410.

In some embodiments, the life stage is one of a group consisting of child, pregnant, lactating, adolescent, adult and elderly. In some embodiments, the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs. In some embodiments, the method further comprises assigning a physical condition to the user based on the third amount, the second amount, the number of resistance training sessions and the occupation of the user. In some embodiments, the method further comprises determining a set of the tuples whose tuple condition matches the physical condition assigned to the user, and generating a recommendation for the user based on at least one of the set, wherein the recommendation identifies the factors of the at least one of the set and whether to increase or decrease each of the factors. In some embodiments, the method further comprises decreasing the preliminary physical activity score of the user if one or both of the third amount and the second amount equal zero and the life stage of the user is adult, elderly, child or adolescent. In some embodiments, the method further comprises increasing the preliminary physical activity score of the user if the preliminary physical activity score is greater than a first threshold value and the life stage of the user is adult, elderly, child or adolescent. In some embodiments, the method further comprises increasing the preliminary physical activity score of the user if the preliminary physical activity score is greater than a second threshold value and the life stage of the user is pregnant or lactating. In some embodiments, the method further comprises determining a number of calories burned by the user within the predetermined period based on the first amount, the second amount, the third amount, the number of resistance training sessions and the weight of the user.

Figure 15:
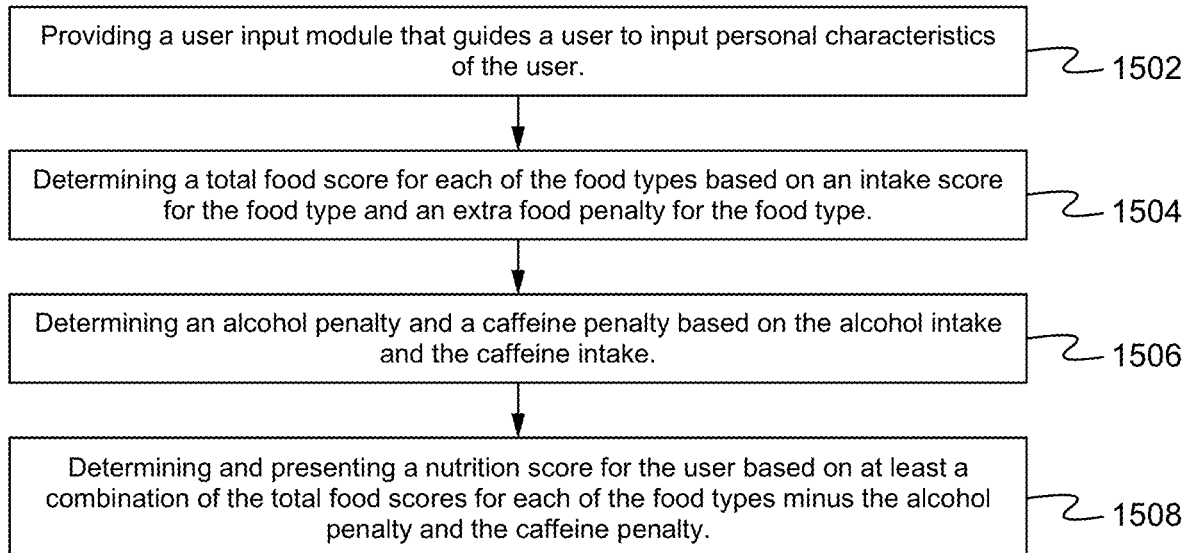
FIG. 15 illustrates a method of implementing a personal health platform for providing nutrition scores and promoting healthy choices to one or more users according to some embodiments.

FIG. 15 illustrates a method of implementing a personal health platform 99 for providing nutrition scores and promoting healthy choices to one or more users according to some embodiments. As shown in FIG. 15, the platform 99 provides a user input module that guides a user to input personal characteristics of the user at the step 1502. In some embodiments, the personal characteristics comprise intake values for a plurality of food types (e.g. vegetables, fruit, dairy, whole grain, refined grain, meat/eggs, seafood and oil) over a predetermined period including a vegetable intake value, a fruit intake value, a dairy intake value, a whole grain intake value, a refined grain intake value, a meat/egg intake value, a seafood intake value and an oil intake value. In some embodiments, the personal characteristics of the user also include other intake types (e.g. alcohol, caffeine, processed foods, sodium, empty calories) such as an alcohol intake and a caffeine intake for the user. The platform 99 determines a total food score for each of the food types based on an intake score for the food type and an extra food penalty for the food type at the step 1504. As described in detail above in the nutrition module section, the intake score is based on the intake value of the food type input by the user divided by a predetermined optimal intake value for the food type. The platform 99 determines an alcohol penalty and a caffeine penalty based on the alcohol intake and the caffeine intake at the step 1506. The platform 99 determines and presents a nutrition score for the user based on at least a combination of the total food scores for each of the food types minus the alcohol penalty and the caffeine penalty at the Step 1508.

In some embodiments, the method further comprises determining a quantity of free calories of the user based on a difference between a total intake value of the user and intakes needs value of the user, wherein the total intake value is a sum of the vegetable intake value, the fruit intake value, the dairy intake value, the whole grain intake value, the refined grain intake value, the meat/egg intake value, the seafood intake value and the oil intake value. In some embodiments, the method further comprises allocating portions of the quantity of free calories to one or more of the food types, wherein the size of the portion allocated to the food type is identified as a tolerance value of the food type. In some embodiments, the quantity of free calories are allocated to the one or more of the food types based on a set of distribution percentages that indicate a percentage of the quantity of free calories to allocate to each of the food types. In some embodiments, the method further comprises determining an extra food value for each of the food types based on a difference between the intake value of that food type and a sum of the predetermined optimum intake value of the food type and the tolerance value of the food type.

In some embodiments, the method further comprises determining the extra food penalty value for each of the food types based on a penalty factor multiplied by the extra food value for the food type divided by the predetermined optimum intake value for the food type. In some embodiments, the intake needs value is a based on a physical activity level of the user. In some embodiments, the personal characteristics include a life stage of the user selected from a group consisting of: child, adolescent, adult, elderly, pregnant and lactating. In some embodiments, the method further comprises determining the caffeine penalty based on whether the caffeine intake exceeds a caffeine threshold associated with the life stage of the user. In some embodiments, the method further comprises determining the alcohol penalty based on whether the alcohol intake exceeds an alcohol threshold associated with the life stage of the user.

Figure 16:
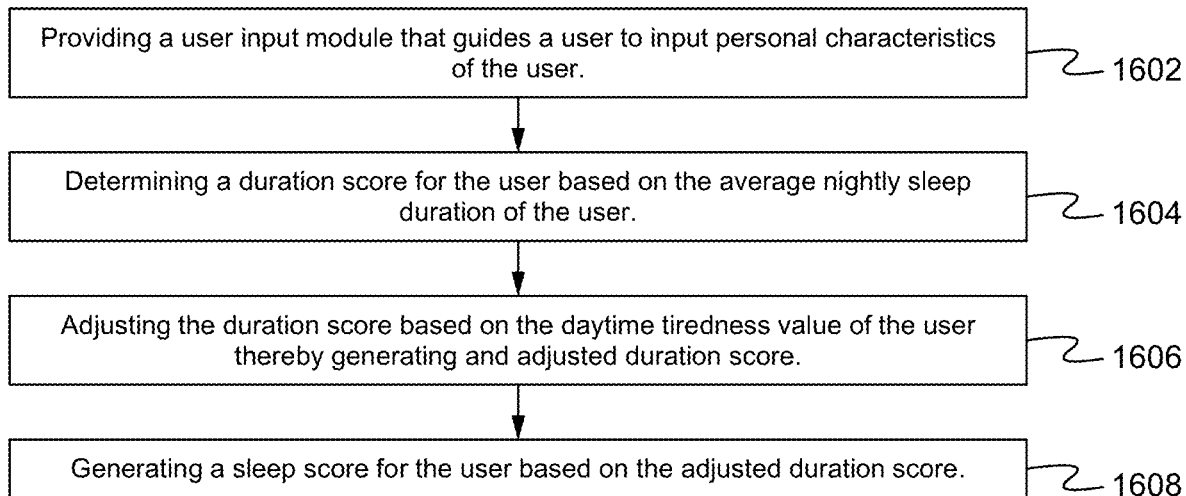
FIG. 16 illustrates a method of implementing a personal health platform for providing sleep scores and promoting healthy choices to one or more users according to some embodiments.

FIG. 16 illustrates a method of implementing a personal health platform 99 for providing sleep scores and promoting healthy choices to one or more users according to some embodiments. As shown in FIG. 16, the platform 99 provides a user input module that guides a user to input personal characteristics of the user at the step 1602. In some embodiments, the personal characteristics comprise an average nightly sleep duration and a daytime tiredness value, wherein the daytime tiredness value indicates how tired the user feels during daytime as evaluated by the user. The platform 99 determines a duration score for the user based on the average nightly sleep duration of the user at the step 1604. The platform 99 adjusts the duration score based on the daytime tiredness value of the user thereby generating and adjusted duration score at the step 1606. The platform 99 generates a sleep score for the user based on the adjusted duration score at the step 1608. In some embodiments, the adjusting of the duration score comprises doubling the duration score if the tiredness value is within a first range indicating that the user is not very tired during the daytime. In some embodiments, the adjusting of the duration score comprises halving the duration score if the tiredness value is within a second range indicating that the user is at least very tired during the daytime. In some embodiments, the personal characteristics include a time to fall asleep, a number of times the user wakes up a night, a daytime nap duration and a sleep medication status.

In some embodiments, the time to fall asleep indicates how long the user takes to fall asleep and the sleep medication status indicates whether the user currently uses medication for falling asleep. In some embodiments, the method further comprises converting: the time to fall asleep to an adjusted time to fall asleep value, the number of times the user wakes up a night to an adjusted number of times the user wakes value, and the daytime nap duration to an adjusted daytime nap value. In some embodiments, the sleep score is further based on a combination of the adjusted time to fall asleep value, the adjusted daytime nap value and the adjusted number of times the user wakes value. In some embodiments, the method further comprises lowering the sleep score based on the sleep medication status indicating that the user currently uses medication for falling asleep. In some embodiments, the method further comprises assigning a sleep condition to the user based on the sleep score of the user. In some embodiments, the personal health platform is coupled with a health knowledge base coupled with the device, stored on a non-transitory computer-readable medium and including a plurality of tuples that each include a tuple condition a user is able to have, a factor that affects the condition, and relationship that defines how the factor affects the condition. In some embodiments, the method further comprises determining a set of the tuples whose tuple condition matches the sleep condition assigned to the user, and generating a recommendation for the user based on at least one of the set, wherein the recommendation identifies the factors of the at least one of the set and whether to increase or decrease each of the factors.

Figure 17:
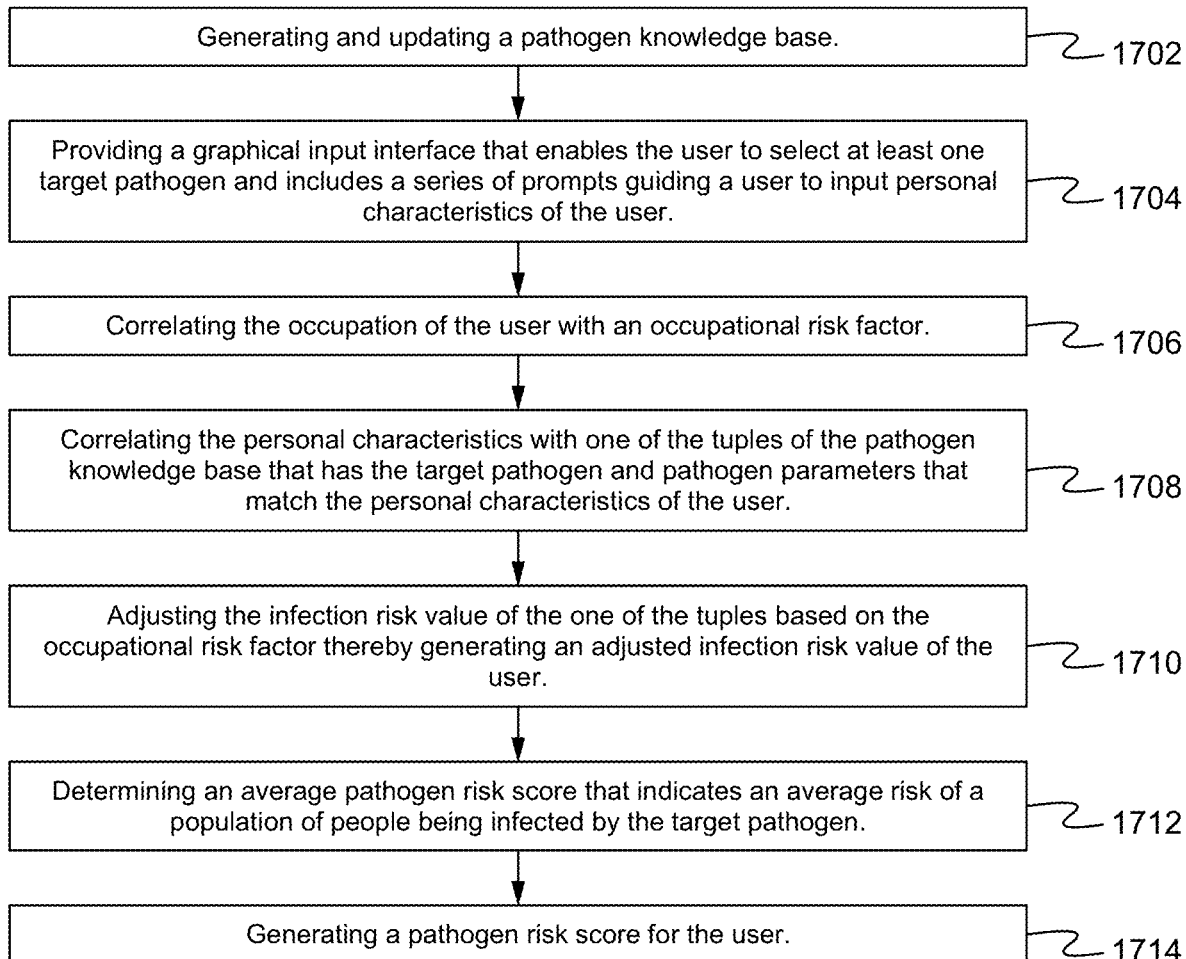
FIG. 17 illustrates a method of determining a pathogen risk and providing pathogen risk recommendations one or more users according to some embodiments.

FIG. 17 illustrates a method of determining a pathogen risk and providing pathogen risk recommendations one or more users according to some embodiments. As shown in FIG. 17, the platform 99 generates and updates a pathogen knowledge base at the step 1702. The pathogen knowledge base is able to be a part of the knowledge base 106 and/or separate from the knowledge base as an independent knowledge base or database. The pathogen knowledge base is able to include a plurality of tuples that each include a pathogen, one or more pathogen parameters that affect an infection risk to the pathogen, and an infection risk value that defines a likelihood of a user having the pathogen parameters to be infected by the pathogen of the tuple. The platform 99 provides a graphical input interface that enables the user to select a target pathogen and includes a series of prompts guiding a user to input personal characteristics of the user including at least an age, sex, location and occupation of the user at the step 1704. The platform correlates the occupation of the user with an occupational risk factor based on an occupational risk table at the step 1706. The platform correlates the personal characteristics with one of the tuples of the pathogen knowledge base that has the target pathogen and pathogen parameters that match the personal characteristics of the user at the step 1708. The platform adjusts the infection risk value of the one of the tuples based on the occupational risk factor thereby generating an adjusted infection risk value of the user at the step 1710. The platform 99 determines an average pathogen risk score that indicates an average risk of a population of people being infected by the target pathogen based on the pathogen database at the step 1712. The platform generates a pathogen risk score for the user that reflects a difference between the average pathogen risk score and adjusted infection risk value of the user at the step 1714. In some embodiments, the pathogen risk score is calculated using the metric: Pathogen risk score=(average pathogen infection risk over all human populations*average occupational risk over all occupations)−(pathogen infection risk of a user A (having personal characteristics a, b, c . . . )*(occupational risk of occupation of user A).

In some embodiments, the method further comprises dynamically measuring and inputting one or more of the parameters of the user with the user device 104. For example, the user device 104 is able to measure one or more of heart rate, blood oxygen level and respiratory rate of the user (e.g. as directed by the platform 99). In some embodiments, the method further comprises determining a current location of the user device 104 and determining one or more businesses and events near the current location. In some embodiments, the method further comprises, using an event/business pathogen risk database, determining an event pathogen risk value for each of the one or more businesses and events based on at least one of a type of the business or the event and a location of the business or the event. In some embodiments, the method further comprises providing one or more pathogen recommendations to the user, wherein the pathogen recommendations indicate the event pathogen risk value for each of the one or more businesses and events based on a type of the business or the event. In some embodiments, the method further comprises generating an overall pathogen risk score for the user by averaging the pathogen risk score for each of the pathogens for the user. Thus, the method provides the advantage of not only illustrating how much more at risk the user is compared to an average person (which is more useful than a risk value without any comparison), but also provides the risks posed by locations and events near the user in order to let them make informed pathogen risk decisions on places they go and events they attend.

Figure 18:
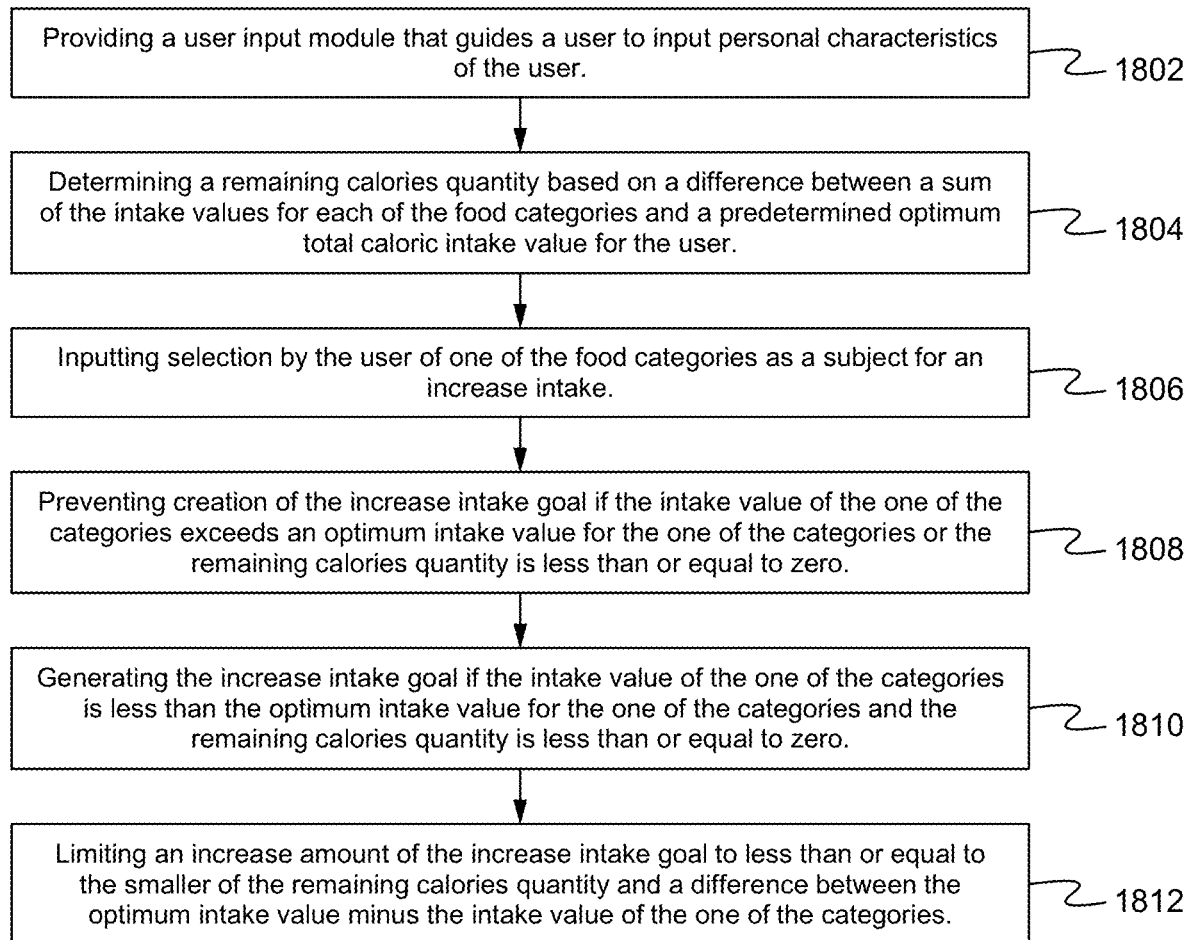
FIG. 18 illustrates a method of implementing a personal health platform for promoting healthy choices to one or more users according to some embodiments.

FIG. 18 illustrates a method of implementing a personal health platform 99 for promoting healthy choices to one or more users according to some embodiments. As shown in FIG. 18, the platform 99 provides a user input module that guides a user to input personal characteristics of the user at the step 1802. In some embodiments, the personal characteristics comprise at least an intake value for a plurality of food categories. The platform 99 determines a remaining calories quantity based on a difference between a sum of the intake values for each of the food categories and a predetermined optimum total caloric intake value for the user at the step 1804. The platform 99 inputs selection by the user of one of the food categories as a subject for an increase intake goal at the step 1806. The platform 99 prevents creation of the increase intake goal if the intake value of the one of the categories exceeds an optimum intake value for the one of the categories or the remaining calories quantity is less than or equal to zero at the Step 1808. The platform 99 generates the increase intake goal if the intake value of the one of the categories is less than the optimum intake value for the one of the categories and the remaining calories quantity is less than or equal to zero at the step 1810. The platform 99 limits an increase amount of the increase intake goal to less than or equal to the smaller of the remaining calories quantity and a difference between the optimum intake value minus the intake value of the one of the categories at the step 1812.

In some embodiments, wherein the personal characteristics include a current performance value for one or more types of physical activity and one or more types of social activity, the method further comprises generating the increase performance goal indicating a quantity of more time the user would like to spend performing the one of the types than the current performance value for the one of the types upon selection by the user of one of the types of physical activity or social activity as a subject for an increase performance goal. In some embodiments, the method further comprises calculating a nutrition score based on the intake values of each of the food categories and automatically recalculating the nutrition score upon completion of the increase intake goal based on a completion percentage of the increase intake goal. In some embodiments, the automatic recalculating comprises determining a result of the completion percentage multiplied by the increase amount of the increase intake goal, increasing the intake value of the one of the food categories by the result, and recalculating the nutrition score using the increased intake value. In some embodiments, the increase intake goal includes a duration that defines when the increase intake goal ends and a frequency that defines how many times compliance with the increase intake goal is checked during the duration, and further wherein the completion percentage is equal to a number of times the user indicated compliance with the increase intake goal divided by an amount of times compliance with the increase intake goal was checked during the duration.

In some embodiments, the method further comprises, in response to preventing creation of the increase intake goal, presenting a replace intake goal that combines an intake increase in the one of the food categories with a matching intake decrease in a second of the food categories whose intake value is greater than an optimum intake value for the second of the food categories. In some embodiments, the method further comprises, after selection of a goal creation function by the user, determining if the remaining calories quantity is greater than zero, and if so, automatically presenting an increase intake goal for each of the food categories whose intake value is less than an optimum intake value for that food category. In some embodiments, the method further comprises, after selection of a goal creation function by the user, automatically presenting a decrease goal for each of the food categories whose intake value is greater than an optimum intake value for that food category. In some embodiments, the method further comprises, after selection of an increase goal creation function and a first of the food categories by the user, determining if the remaining calories quantity is greater than zero, and if not, automatically presenting a replace goal that combines an intake increase in the first of the food categories with a matching intake decrease in a second of the food categories whose intake value is greater than an optimum intake value for the second of the food categories. In some embodiments, the second of the food categories is selected by the user from a list of all of the food categories whose intake value is greater than the optimum intake value for that food category and/or the selection by the user of the one of the food categories as the subject for the increase intake goal comprises selection from the user interface of a food that belongs to the one of the food categories.

Figure 19:
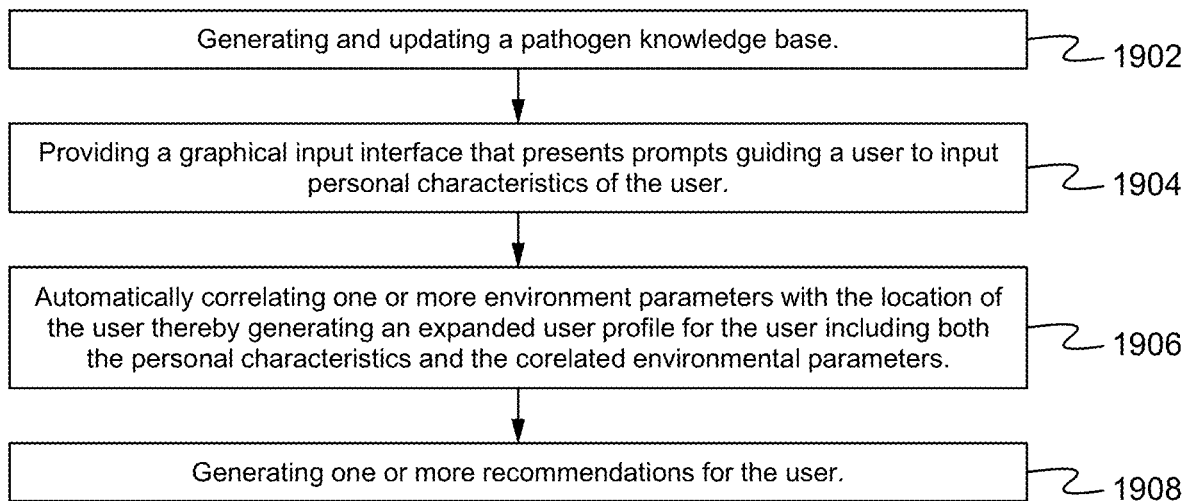
FIG. 19 illustrates a method of implementing a personal health system for providing customized health recommendations to one or more users according to some embodiments.

FIG. 19 illustrates a method of implementing a personal health system for providing customized health recommendations to one or more users according to some embodiments. As shown in FIG. 19, the platform 99 generates and updates a health knowledge base 106 at the step 1902. The platform 99 provides a graphical input interface that presents prompts guiding a user to input personal characteristics of the user at the step 1904. In some embodiments, the personal characteristics including at least a location of the user. The platform 99 automatically correlates one or more environment parameters with the location of the user based on one or more environmental parameter databases thereby generating an expanded user profile for the user including both the personal characteristics and the correlated environmental parameters at the step 1906. The platform 99 generates one or more recommendations for the user at the step 1908. In some embodiments, the recommendations are generated by determining and selecting one or more of the tuples whose condition matches at least one of the personal characteristics and the environmental parameters of the user, and displays an image associating the factor and the condition of the one or more of the tuples and instructing to increase or decrease the factor.

In some embodiments, the personal characteristics include one or more of a group consisting of: age, sex, genetics of the user, allergies, eating habits, smoking habits, current medications, current medical conditions, occupation, physical activity habits, sleep habits, stress, genetic susceptibilities, behaviors and social habits. In some embodiments, the environment parameters include one or more of a group consisting of: air quality, quantity of blue space, quantity of green space, weather, socioeconomic status, food accessibility, and healthcare accessibility. In some embodiments, the method further comprises preventing selection of recommendations whose factor matches one of the allergies of the personal characteristics of the user. In some embodiments, each of the tuples include metadata indicating demographic data of a population to which the factor, condition and relationship of the tuple applies. In some embodiments, the method further comprises determining a subset of the tuples whose demographic data corresponds to the personal characteristics of the user, and when selecting the recommendations, only compare the at least one of the personal characteristics and the environmental parameters with subset of the tuples.

In some embodiments, the method further comprises determining a physical activity score, a social activity score, a sleep score, a pathogen risk score, a stress score and a nutrition score for the user based on the personal characteristics of the user. In some embodiments, the method further comprises selecting and displaying one or more recommendations for the user based on at least one of the physical activity score, the social activity score, the sleep score, the pathogen risk score, the stress score and the nutrition score. In some embodiments, the method further comprises adjusting at least one of the physical activity score, the social activity score, the sleep score, the pathogen risk score, the stress score and the nutrition score based on the genetics of the user. In some embodiments, the method further comprises after at least a predetermined period has elapsed since one of the recommendations was displayed to the user, inputting from the user whether the user has followed the one of the recommendations, inputting from the user updates to one or more of the personal characteristics of the user, adjusting the tuple upon which the one of the recommendations was based when the user followed the one of the recommendations and the user updates indicate a change to one or more of the personal characteristics of the user that were matched with the condition of the tuple. In some embodiments, the method further comprises adjusting the tuple upon which the one of the recommendations was based by performing one or more of a group consisting of: changing a relationship strength value of the tuple, removing the tuple from the knowledge base, and creating a new tuple having the same condition, but with a different factor, relationship, or both as the tuple upon which the one of the recommendations was based.

Figure 20:
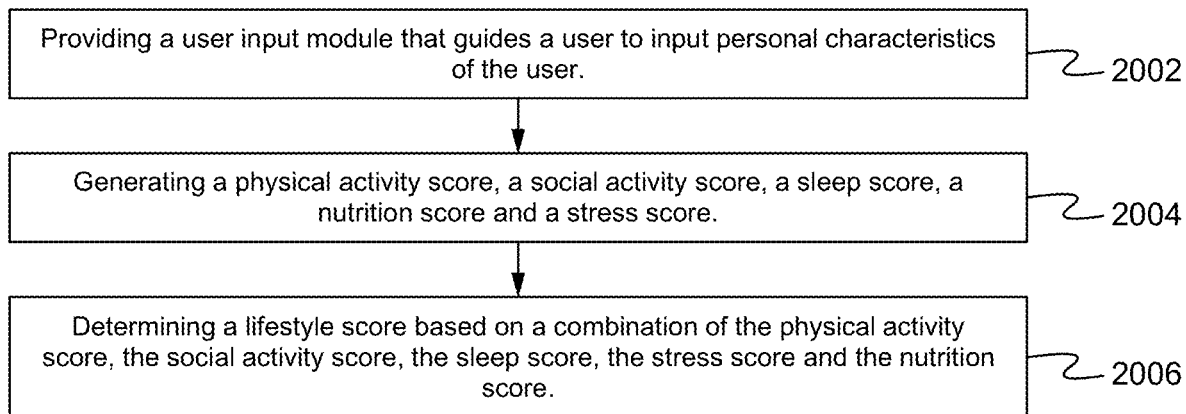
FIG. 20 illustrates a method of implementing a personal health platform for promoting healthy choices to one or more users according to some embodiments.

FIG. 20 illustrates a method of implementing a personal health platform 99 for promoting healthy choices to one or more users according to some embodiments. As shown in FIG. 20, the platform 99 provides a user input module that guides a user to input personal characteristics of the user at the step 2002. In some embodiments, the personal characteristics comprise at least physical activity characteristics, social activity characteristics, sleep characteristics, nutrition characteristics and stress characteristics. The platform 99 generates a physical activity score based on the physical activity characteristics, a social activity score based on the social activity characteristics, a sleep score based on the sleep characteristics, a nutrition score based on the nutrition characteristics and a stress score based on the stress characteristics at the step 2004. The platform 99 determines a lifestyle score based on a combination of the physical activity score, the social activity score, the sleep score, the stress score and the nutrition score at the step 2006.

In some embodiments, the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity. In some embodiments, the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs. In some embodiments, the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value.

In some embodiments, the sleep characteristics comprise an average nightly sleep duration and a daytime tiredness value, wherein the daytime tiredness value indicates how tired the user feels during daytime as evaluated by the user. In some embodiments, the stress characteristics comprise an occupation of the user, a method of transport to the occupation, and a work commute distance of the user. In some embodiments, the social activity characteristics comprise an amount of time spent participating in sports, an amount of time participating in religious services, an amount of time spent with friends, an amount of time spent with family, and an amount of time spent volunteering. In some embodiments, determining the lifestyle score includes multiplying the physical activity score, the social activity score, the sleep score, the stress score and the nutrition score by separate weighting percentages, wherein the separate weighting percentages add up to 100 percent. In some embodiments, the method further comprises assigning an identified condition to the user based on at least one of the physical activity score, the social activity score, the sleep score, the nutrition score and the stress score. In some embodiments, the personal health platform is coupled with a health knowledge base coupled with the device, stored on a non-transitory computer-readable medium and including a plurality of tuples that each include a tuple condition a user is able to have, a factor that affects the condition, and relationship that defines how the factor affects the condition. In some embodiments, the method further comprises determining a set of the tuples whose tuple condition matches the identified condition assigned to the user, and generating a recommendation for the user based on at least one of the set, wherein the recommendation identifies the factors of the at least one of the set and whether to increase or decrease each of the factors.

Advantages

Thus, the personal health system 100 described herein has numerous advantages. Specifically, the system provides the advantage of analyzing real-world user data in the context of a person's specific environment and identifies factors that ultimately lead to the discovery of previously undetected associations, to better understand health and disease processes and improves on prior art systems that did not include such expanded personal and location-specific characteristics of the user. To develop the right recommendations at the right time and for the right place embodiments of the system are able to implement a ranking module of the relations that are extracted from the public sources. The ranking system is able to disambiguate contradictory relations by relying on the quality of the source obtained from scientifically accepted indexes of impact factor and the type of study. The ranking system is also used to prioritize the relations according to specific disease outcomes. Thus, the system also provides the benefit of improving the health status and the quality of life of the users of the system, thereby reducing the burden on the national healthcare system.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiments chosen for illustration without departing from the spirit and scope of the invention as defined by the claims. For example, it is understood that although the platform is described as comprising various modules, the names of these modules are arbitrary and are an artificial construct to assist those skilled in the art to gain a full and transparent understanding of the systems, methods and devices. It is understood that those skilled in the art have the ability to mix and match the functions embodied within the modules, or to abandon one or more of the modules. Further, as described herein, the term "page" is able to refer to a webpage, a website, an application screen/page, a user interface and/or any other type of digital page. Additionally, although some examples in the description herein focus on a user interface incorporating sliders and text boxes as a manner of enabling user input, it is understood that other graphical user interface input elements are able to be used.

What is claimed is:

1. A personal health system for promoting healthy choices to one or more users, the personal health system comprising:
    a non-transitory computer readable memory storing a knowledge base including a plurality of tuples, wherein each tuple includes a condition, one or more factors that affect the condition, and a relationship that describes how the one or more factors affect the condition, wherein one or more of the factors are occupations; and
    at least one computing device including a processor and a non-transitory computer-readable medium coupled with the processor and storing a personal health platform having a user interface, wherein when executed by the processor the personal health platform is operable to:
        generate an input graphical user interface on the device having one or more input features configured to input personal characteristics of the user, the personal characteristics including physical activity characteristics, social activity characteristics, sleep characteristics, nutrition characteristics and stress characteristics, wherein the stress characteristics comprise an occupation of the user, a method of transport to the occupation, and a work commute distance of the user, and further wherein the factors and the conditions of the tuples are one or more of the personal characteristics, the non-transitory computer-readable medium storing a user profile and a lifestyle score digital image, the user profile including a physical activity score that is based on the physical activity characteristics, a social activity score that is based on the social activity characteristics, a sleep score that is based on the sleep characteristics, a nutrition score that is based on the nutrition characteristics and a stress score that is based on the stress characteristics and the lifestyle score digital image indicating a lifestyle score that is based on a combination of the physical activity score, the social activity score, the sleep score, the stress score and the nutrition score; and provide a navigation graphical user interface that:

enables the user to select one or more of the conditions as desired conditions;

generates a navigation digital image that concurrently displays one or more relationship strength features adjacent to a network web, wherein the network web graphically illustrates nodes representing the desired conditions and visible connections between each of the nodes and one or more related factors of the factors that have an identified relationship with the desired conditions according to the tuples that include the desired conditions;

enables the user to selectively input changes to one or more relationship strength threshold values associated with the desired conditions using the relationship strength features; and dynamically alters the network web as concurrently displayed based on the input changes to the relationship strength threshold values, wherein the altering of the network web is such that the one or more related factors included in the network web is modified to only be a set of the related factors whose identified relationship to the desired conditions, according to the tuples that include the desired conditions, falls within one or more relationship strength ranges defined by the relationship strength threshold values for the desired conditions.

2. The personal health system of claim 1, wherein the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity.

3. The personal health system of claim 2, wherein the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs.

4. The personal health system of claim 3, wherein the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value.

5. The personal health system of claim 4, wherein the sleep characteristics comprise an average nightly sleep duration and a daytime tiredness value, wherein the daytime tiredness value indicates how tired the user feels during daytime as evaluated by the user.

6. The personal health system of claim 1, wherein the social activity characteristics comprise an amount of time spent participating in sports, an amount of time participating in religious services, an amount of time spent with friends, an amount of time spent with family, and an amount of time spent volunteering.

7. The personal health system of claim 6, wherein determining the lifestyle score includes multiplying the physical activity score, the social activity score, the sleep score, the stress score and the nutrition score by separate weighting percentages, wherein the separate weighting percentages add up to 100 percent.

8. The personal health system of claim 7, wherein the personal health platform is operable to assign an identified condition to the user based on at least one of the physical activity score, the social activity score, the sleep score, the nutrition score and the stress score.

9. The personal health system of claim 8, further comprising a health knowledge base coupled with the device, stored on a non-transitory computer-readable medium and including the plurality of tuples.

10. The personal health system of claim 9, wherein the personal health platform is operable to determine a set of the tuples whose tuple condition matches the identified condition assigned to the user, and generate a recommendation for the user based on at least one of the set, wherein the recommendation identifies the factors of the at least one of the set and whether to increase or decrease each of the factors.

11. A non-transitory computer-readable medium storing a personal health platform for promoting healthy choices to one or more users and a knowledge base including a plurality of tuples, wherein each tuple includes a condition, one or more factors that affect the condition, and a relationship that describes how the one or more factors affect the condition, wherein one or more of the factors are occupations, wherein when executed by a processor the personal health platform is operable to:

generate an input graphical user interface having one or more input features configured to input personal characteristics of the user, the personal characteristics including physical activity characteristics, social activity characteristics, sleep characteristics, nutrition characteristics and stress characteristics, wherein the stress characteristics comprise an occupation of the user, a method of transport to the occupation, and a work commute distance of the user, and further wherein the factors and the conditions of the tuples are one or more of the personal characteristics, the non-transitory computer-readable medium storing a user profile and a lifestyle score digital image, the user profile including a physical activity score that is based on the physical activity characteristics, a social activity score that is based on the social activity characteristics, a sleep score that is based on the sleep characteristics, a nutrition score that is based on the nutrition characteristics and a stress score that is based on the stress characteristics and the lifestyle score digital image indicating a lifestyle score that is based on a combination of the physical activity score, the social activity score, the sleep score, the stress score and the nutrition score; and provide a navigation graphical user interface that:

enables the user to select one or more of the conditions as desired conditions;

generates a navigation digital image that concurrently displays one or more relationship strength features adjacent to a network web, wherein the network web graphically illustrates nodes representing the desired conditions and visible connections between each of the nodes and one or more related factors of the factors that have an identified relationship with the desired conditions according to the tuples that include the desired conditions;

enables the user to selectively input changes to one or more relationship strength threshold values associated with the desired conditions using the relationship strength features; and dynamically alters the network web as concurrently displayed based on the input changes to the relationship strength threshold values, wherein the altering of the network web is such that the one or more related factors included in the network web is modified to only be a set of the related factors whose identified relationship to the desired conditions, according to the tuples that include the desired conditions, falls within one or more relationship strength ranges defined by the relationship strength threshold values for the desired conditions.

12. The medium of claim 11, wherein the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity.

13. The medium of claim 12, wherein the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs.

14. The medium of claim 13, wherein the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value.

15. The medium of claim 14, wherein the sleep characteristics comprise an average nightly sleep duration and a daytime tiredness value, wherein the daytime tiredness value indicates how tired the user feels during daytime as evaluated by the user.

16. The medium of claim 11, wherein the social activity characteristics comprise an amount of time spent participating in sports, an amount of time participating in religious services, an amount of time spent with friends, an amount of time spent with family, and an amount of time spent volunteering.

17. The medium of claim 16, wherein determining the lifestyle score includes multiplying the physical activity score, the social activity score, the sleep score, the stress score and the nutrition score by separate weighting percentages, wherein the separate weighting percentages add up to 100 percent.

18. The medium of claim 17, wherein the personal health platform is operable to assign an identified condition to the user based on at least one of the physical activity score, the social activity score, the sleep score, the nutrition score and the stress score.

19. The medium of claim 18, further comprising a health knowledge base stored on the non-transitory computer-readable medium and including the plurality of tuples.

20. The medium of claim 19, wherein the personal health platform is operable to determine a set of the tuples whose tuple condition matches the identified condition assigned to the user, and generate a recommendation for the user based on at least one of the set, wherein the recommendation identifies the factors of the at least one of the set and whether to increase or decrease each of the factors.

21. A method of implementing a personal health system for promoting healthy choices to one or more users, the method comprising:

with at least one computing device having a non-transitory computer-readable medium:

maintaining a knowledge base including a plurality of tuples, wherein each tuple includes a condition, one or more factors that affect the condition, and a relationship that describes how the one or more factors affect the condition, wherein one or more of the factors are occupations;

generating an input graphical user interface on the device having one or more input features configured to input personal characteristics of the user, the personal characteristics including physical activity characteristics, social activity characteristics, sleep characteristics, nutrition characteristics and stress characteristics, wherein the stress characteristics comprise an occupation of the user, a method of transport to the occupation, and a work commute distance of the user, and further wherein the factors and the conditions of the tuples are one or more of the personal characteristics; the non-transitory computer-readable medium storing a user profile and a lifestyle score digital image, the user profile including a physical activity score that is based on the physical activity characteristics, a social activity score that is based on the social activity characteristics, a sleep score that is based on the sleep characteristics, a nutrition score that is based on the nutrition characteristics and a stress score that is based on the stress characteristics and the lifestyle score digital image indicating a lifestyle score based on a combination of the physical activity score, the social activity score, the sleep score, the stress score and the nutrition score; and providing a navigation graphical user interface that:
enables the user to select one or more of the conditions as desired conditions;
generates a navigation digital image that concurrently displays one or more relationship strength features adjacent to a network web, wherein the network web graphically illustrates nodes representing the desired conditions and visible connections between each of the nodes and one or more related factors of the factors that have an identified relationship with the desired conditions according to the tuples that include the desired conditions;
enables the user to selectively input changes to one or more relationship strength threshold values associated with the desired conditions using the relationship strength features; and
dynamically alters the network web as concurrently displayed based on the input changes to the relationship strength threshold values, wherein the altering of the network web is such that the one or more related factors included in the network web is modified to only be a set of the related factors whose identified relationship to the desired conditions, according to the tuples that include the desired conditions, falls within one or more relationship strength ranges defined by the relationship strength threshold values for the desired conditions.

22. The method of claim 21, wherein the physical activity characteristics comprise a life stage of the user, a first amount of time spent by the user doing a first level of physical activity within a predetermined period, a second amount of time spent by the user doing a second level of physical activity within the predetermined period, a third amount of time spent by the user doing a third level of physical activity within the predetermined period and a number of resistance training sessions during the predetermined period, wherein the third level of physical activity is more strenuous than the second level of physical activity which is more strenuous than the first level of physical activity.

23. The method of claim 22, wherein the first level of physical activity is non-sedentary waking behavior that requires less than 3.0 metabolic equivalent of tasks (MET), the second level of physical activity is behavior that requires 3.0-6.0 METs, and the third level of physical activity is behavior that requires greater than 6.0 METs.

24. The method of claim 23, wherein the nutrition characteristics comprise intake values for a plurality of food types over a predetermined period, the intake values including a vegetable intake value, a fruit intake value, a dairy intake value, a whole grain intake value, a refined grain intake value, a meat/egg intake value, a seafood intake value and an oil intake value, and the food types including vegetables, fruit, dairy, whole grain, refined grain, meat/eggs, seafood and oil, the personal characteristics of the user further including an alcohol intake value and a caffeine intake value.

25. The method of claim 24, wherein the sleep characteristics comprise an average nightly sleep duration and a daytime tiredness value, wherein the daytime tiredness value indicates how tired the user feels during daytime as evaluated by the user.

26. The method of claim 21, wherein the social activity characteristics comprise an amount of time spent participating in sports, an amount of time participating in religious services, an amount of time spent with friends, an amount of time spent with family, and an amount of time spent volunteering.

27. The method of claim 26, wherein determining the lifestyle score includes multiplying the physical activity score, the social activity score, the sleep score, the stress score and the nutrition score by separate weighting percentages, wherein the separate weighting percentages add up to 100 percent.

28. The method of claim 27, further comprising assigning an identified condition to the user based on at least one of the physical activity score, the social activity score, the sleep score, the nutrition score and the stress score.

29. The method of claim 28, wherein the personal health platform is coupled with a health knowledge base coupled with the device, stored on a non-transitory computer-readable medium and including the plurality of tuples.

30. The method of claim 29, further comprising determining a set of the tuples whose tuple condition matches the identified condition assigned to the user, and generating a recommendation for the user based on at least one of the set, wherein the recommendation identifies the factors of the at least one of the set and whether to increase or decrease each of the factors.

* * * * *